US012686874B2

(12) United States Patent
Fuller et al.

(10) Patent No.: US 12,686,874 B2

(45) Date of Patent: Jul. 21, 2026

(54) GENE THERAPY FOR TREATING PROPIONIC ACIDEMIA

(71) Applicant: Ultragenyx Pharmaceutical Inc., Novato, CA (US)

(72) Inventors: Matthew Scott Fuller, Millis, MA (US); Samuel Wadsworth, Monterey, MA (US); Kelly Reed Clark, Westerville, OH (US); Sean Christopher Daugherty, Petaluma, CA (US); Stewart Craig, Cambridge, MA (US)

(73) Assignee: Ultragenyx Pharmaceutical Inc., Novato, CA (US)

( * ) Notice: Subject to any disclaimer, the term of this patent is extended or adjusted under 35 U.S.C. 154(b) by 866 days.

(21) Appl. No.: 17/906,902

(22) PCT Filed: Mar. 30, 2021

(86) PCT No.: PCT/US2021/024892

§ 371 (c)(1),
(2) Date: Sep. 21, 2022

(87) PCT Pub. No.: WO2021/202532

PCT Pub. Date: Oct. 7, 2021

(65) Prior Publication Data

US 2023/0129893 A1 Apr. 27, 2023

Related U.S. Application Data

(60) Provisional application No. 63/002,541, filed on Mar. 31, 2020.

(51) Int. Cl.

*C12N 15/86* (2006.01)
*A61K 48/00* (2006.01)
*A61P 3/00* (2006.01)
*C12N 9/00* (2006.01)

(52) U.S. Cl.

CPC ................ *C12N 15/86* (2013.01); *A61P 3/00* (2018.01); *C12N 9/93* (2013.01); *C12Y 604/01003* (2013.01); *A61K 48/00* (2013.01); *C12N 2750/14143* (2013.01); *C12N 2800/22* (2013.01); *C12N 2830/50* (2013.01)

(58) Field of Classification Search

None

See application file for complete search history.

(56) References Cited

U.S. PATENT DOCUMENTS 6,569,662 B1 * 5/2003 Tang ...................... C07K 14/47 435/219
7,018,628 B1 3/2006 Sarkis et al.
7,282,199 B2 10/2007 Gao et al.
7,790,449 B2 9/2010 Gao et al.
8,734,809 B2 5/2014 Gao et al.
8,927,514 B2 1/2015 Chatterjee et al.
9,506,083 B2 11/2016 Arbetman et al.
9,585,971 B2 3/2017 Deverman et al.
9,587,282 B2 3/2017 Schaffer et al.
9,611,302 B2 4/2017 Srivastava et al.
9,725,485 B2 8/2017 Srivastava et al.
9,856,539 B2 1/2018 Schaffer et al.
9,909,142 B2 3/2018 Yazicioglu et al.
9,920,097 B2 3/2018 Zhong et al.
10,011,640 B2 7/2018 Srivastava et al.
10,081,659 B2 9/2018 Chiorini et al.
10,179,176 B2 1/2019 Kay et al.
10,202,657 B2 2/2019 Schaffer et al.
10,214,566 B2 2/2019 Schaffer et al.
10,214,785 B2 2/2019 Schaffer et al.
10,266,845 B2 4/2019 Cronin et al.
10,294,281 B2 5/2019 Srivastava et al.
10,301,648 B2 5/2019 Vandenberghe et al.
10,385,320 B2 8/2019 Kay et al.
10,392,632 B2 8/2019 Wright et al.
10,406,214 B2 * 9/2019 Kraus .................... G01N 33/53
11,191,847 B2 * 12/2021 Wang ................. A61K 48/0075
12,472,268 B2 11/2025 Fuller et al.

(Continued)

FOREIGN PATENT DOCUMENTS

EP 1310571 A2 5/2003
WO WO-2003/042397 A2 5/2003

(Continued)

OTHER PUBLICATIONS

Lusby et al., "Nucleotide Sequence of the Inverted Terminal Repetiion in Adeno-Associated Virus DNA" 34(2) Proceedings of the National Academy of Sciences USA 402-409 (Year: 1990).*

Powell et al. (2015), "Viral Expression Cassette Elements to Enhance Transgene Target Specificity and Expression in Gene Therapy," Discov Med. 19(102):49-57.

Propionyl-CoA carboxylase alpha chain, mitochondrial isoform a precurs—Protein—NCBI, and accession No. NP_000273.2, NCBI, 2005.

Propionyl-CoA carboxylase beta chain, mitochondrial isoform 1 precurso—Protein—NCBI, and accession No. NP_000523.2, NCBI, 2006.

(Continued)

*Primary Examiner* — Nancy J Leith

(74) *Attorney, Agent, or Firm* — Antheros Legal Advisors LLP

(57) ABSTRACT

This present disclosure provides recombinant adeno-associated virus (rAAV) and methods of their use in gene therapy for treating propionic acidemia (PA). Also provided are pharmaceutical compositions comprising a rAAV of the invention and a pharmaceutically acceptable carrier or excipient. These pharmaceutical compositions may be useful in gene therapy for the treatment of PA caused by a mutation in propionyl-CoA carboxylase α-subunit (PCCA) or a mutation in propionyl-CoA carboxylase β-subunit (PCCB).

3 Claims, 13 Drawing Sheets

Specification includes a Sequence Listing.

(56) References Cited

U.S. PATENT DOCUMENTS

2007/0036760 A1 2/2007 Wilson et al.
2009/0197338 A1 8/2009 Vandenberghe et al.
2014/0303901 A1 10/2014 Sadeh
2015/0139953 A1 5/2015 Gao et al.
2015/0344911 A1 12/2015 Chatterjee et al.
2017/0119906 A1 5/2017 Riley
2017/0313990 A1* 11/2017 Champion ............... C12N 7/00
2018/0140688 A1 5/2018 Kraus
2019/0076550 A1 3/2019 Wang et al.
2021/0283272 A1 9/2021 Fuller et al.
2023/0129893 A1 4/2023 Fuller et al.
2026/0041788 A1 2/2026 Fuller et al.

FOREIGN PATENT DOCUMENTS

WO WO 2015/059303 A1 * 4/2015 ........... A61K 35/761
WO WO-2016/049230 A1 3/2016
WO WO-2016/186772 A2 11/2016
WO WO-2017/165859 A1 9/2017
WO WO-2017/173043 A1 10/2017
WO WO-2017/180854 A1 10/2017
WO WO-2017/192761 A1 11/2017
WO WO-2018/022905 A2 2/2018
WO WO-2018/126112 A1 7/2018
WO WO-2018/126116 A1 7/2018
WO WO-2018/144709 A2 8/2018
WO WO-2018/156654 A1 8/2018
WO WO-2018/222503 A1 12/2018
WO WO-2018/226602 A1 12/2018
WO WO-2019/168961 A1 9/2019
WO WO-2020/072451 A1 4/2020
WO WO 2021/163322 A1 * 8/2021 ............. C12N 15/86

OTHER PUBLICATIONS

Browner et al., (1989) "Sequence Analysis, Biogenesis, and Mitochondrial Import of the α-subunit of Rat Liver Propionyl-CoA Carboxylase," J Biol Chem 264(21):12680-12685.
Chandler et al. (2011) "Adeno-Associated Virus Serotype 8 Gene Transfer Rescues a Neonatal Lethal Murine Model of Propionic Acidemia," Human Gene Therapy 22(4):477-481 (7 pages).
Colella et al. (2018) "Emerging Issues in AAV-Mediated In Vivo Gene Therapy," Molecular Therapy: Methods & Clinical Development 8:87-104.
Gray et al. (2011) "Optimizing promoters for recombinant adeno-associated virus-mediated gene expression in the peripheral and central nervous system using self-complementary vectors," Human Gene Therapy 22(9):1143-1153.
Guenzel et al. (2013) "Generation of a Hypomorphic Model of Propionic Acidemia Amenable to Gene Therapy Testing," Molecular Therapy 21(7):1316-1323.
Guenzel et al. (2014) "Effects of adeno-associated virus serotype and tissue-specific expression on circulating biomarkers of propionic acidemia," Human Gene Therapy 25(9): 837-843.
Guenzel et al. (2015) "Long-Term Sex-Biased Correction of Circulating Propionic Acidemia Disease Markers by Adeno-Associated Virus Vectors," Human Gene Therapy 26(3):153-160.
Hsia et al. (1973) "Propionic acidemia: Diagnosis by enzyme assay in frozen leukocytes," J Pediatr. 83(4):625-628.
Huang et al: (1990) "Intervening sequences increase efficiency of RNA 3' processing and accumulation of cytoplasmic RNA," Nucleic Acids Research 18(4):937-947.
International Search Report and Written Opinion for corresponding International Application No. PCT/US2019/054003, dated Feb. 6, 2020, 14 pages.
International Search Report and Written Opinion for International Application No. PCT/US2021/024892 mailed Jul. 12, 2021, 15 pages.
Kalousek et al. (1980) "Isolation and Characterization of Propionyl-CoA Carboxylase from Normal Human Liver," J Biol Chem. 255(1):60-65.
Ugarte et al. (1999) "Overview of mutations in the PCCA and PCCB genes causing propionic acidemia," Human Mutation 14(4):275-282.
Vaessen et al. (2009) "AAV gene therapy as a means to increase apolipoprotein (Apo) A-I and high-density lipoprotein-cholesterol levels: correction of murine ApoA-I deficiencAAV gene therapy as a means to increase apolipoprotein (Apo) A-I and high-density lipoprotein-cholesterol levels: correction of murine ApoA-I deficiency," J. Gene Med. 11:697-707.
Van der Meer et al. (1996) "Clinical outcome and long-term management of 17 patients with propionic acidaemia," Eur J Pediatr. 155(3):205-210.
Yang et al. (2004) "Mutation spectrum of the PCCA and PCCB genes in Japanese patients with propionic acidemia," Molecular Genetics and Metabolism 81(4):335-342.

* cited by examiner

| # | ID | DESCRIPTION |
|---|---|---|
| 1 | NA | MOCK |
| 2 | DTC346 | pCis[CMVenh.**CBA** prom.SV40Tintron.PCCAnative.SV40pA] |
| 3 | DTC482 | pCis[**hUBC**.SV40Tintron.PCCAnative.SV40pA] |
| 4 | DTC483 | pCis[**mPGK**.SV40Tintron.PCCAnative.SV40pA] |
| 5 | DTC484 | pCis[**hEF1a**.SV40Tintron.PCCAnative.SV40pA] |
| 6 | DTC485 | pCis[**hPCNA**.SV40Tintron.PCCAnative.SV40pA] |
| 7 | DTC430 | pCis[CMVenh.CBA prom.IVS2intron.PCCAnative.SV40pA] |

| # | ID | DESCRIPTION |
|---|---|---|
| 1 | NA | MOCK |
| 2 | DTC346 | pCis[CMVenh.**CBA** prom.SV40Tintron.PCCAnative.SV40pA] |
| 3 | DTC482 | pCis[**hUBC**.SV40Tintron.PCCAnative.SV40pA] |
| 4 | DTC483 | pCis[**mPGK**.SV40Tintron.PCCAnative.SV40pA] |
| 5 | DTC484 | pCis[**hEF1a**.SV40Tintron.PCCAnative.SV40pA] |
| 6 | DTC485 | pCis[**hPCNA**.SV40Tintron.PCCAnative.SV40pA] |
| 7 | DTC430 | pCis[CMVenh.CBA prom.IVS2intron.PCCAnative.SV40pA] |

SEQUENCE LISTING

```
<160> NUMBER OF SEQ ID NOS: 31

<210> SEQ ID NO 1
<211> LENGTH: 572
<212> TYPE: DNA
<213> ORGANISM: Homo sapiens
<220> FEATURE:
<221> NAME/KEY: misc_feature
<222> LOCATION: (1)..(572)
<223> OTHER INFORMATION: IVS2 INTRON

<400> SEQUENCE: 1

agcttacttg tggtaccgag ctcggatcct gagaacttca gggtgagtct atgggaccct      60

tgatgttttc tttccccttc ttttctatgg ttaagttcat gtcataggaa ggggagaagt     120

aacagggtac acatattgac caaatcaggg taattttgca tttgtaattt taaaaaatgc     180

tttcttcttt taatatactt ttttgtttat cttatttcta atactttccc taatctcttt     240

ctttcagggc aataatgata caatgtatca tgcctctttg caccattcta aagaataaca     300

gtgataattt ctgggttaag gcaatagcaa tatttctgca tataaatatt tctgcatata     360

aattgtaact gatgtaagag gtttcatatt gctaatagca gctacaatcc agctaccatt     420

ctgcttttat tttatggttg ggataaggct ggattattct gagtccaagc taggcccttt     480
```

tgctaatcat gttcatacct cttatcttcc tcccacagct cctgggcaac gtgctggtct 540
gtgtgctggc ccatcacttt ggcaaagaat tg 572

<210> SEQ ID NO 2
<211> LENGTH: 2184
<212> TYPE: DNA
<213> ORGANISM: Homo sapiens
<220> FEATURE:
<221> NAME/KEY: misc_feature
<222> LOCATION: (1)..(2184)
<223> OTHER INFORMATION: PCCA Coding Sequence - Wild-Type

<400> SEQUENCE: 2
atggcggggt tctgggtcgg gacagcaccg ctggtcgctg ccggacggcg tgggcggtgg 60
ccgccgcagc agctgatgct gagcgcggcg ctgcggaccc tgaagcatgt tctgtactat 120
tcaagacagt gcttaatggt gtcccgtaat cttggttcag tgggatatga tcctaatgaa 180
aaaacttttg ataaaattct tgttgctaat agaggagaaa ttgcatgtcg ggttattaga 240
acttgcaaga agatgggcat taagacagtt gccatccaca gtgatgttga tgctagttct 300
gttcatgtga aaatggcgga tgaggctgtc tgtgttggcc cagctcccac cagtaaaagc 360
tacctcaaca tggatgccat catggaagcc attaagaaaa ccagggccca agctgtacat 420
ccaggttatg gattcctttc agaaaacaaa gaatttgcca gatgtttggc agcagaagat 480
gtcgttttca ttggacctga cacacatgct attcaagcca tgggcgacaa gattgaaagc 540
aaattattag ctaagaaagc agaggttaat acaatccctg gctttgatgg agtagtcaag 600
gatgcagaag aagctgtcag aattgcaagg gaaattggct accctgtcat gatcaaggcc 660
tcagcaggtg gtggtgggaa aggcatgcgc attgcttggg atgatgaaga gaccagggat 720
ggttttagat tgtcatctca agaagctgct tctagttttg gcgatgatag actactaata 780
gaaaaattta ttgataatcc tcgtcatata gaaatccagg ttctaggtga taaacatggg 840
aatgctttat ggcttaatga aagagagtgc tcaattcaga gaagaaatca gaaggtggtg 900
gaggaagcac caagcatttt tttggatgcg gagactcgaa gagcgatggg agaacaagct 960
gtagctcttg ccagagcagt aaaatattcc tctgctggga ccgtggagtt ccttgtggac 1020
tctaagaaga atttttattt cttggaaatg aatacaagac tccaggttga gcatcctgtc 1080
acagaatgca ttactggcct ggacctagtc caggaaatga tccgtgttgc taagggctac 1140
cctctcaggc acaaacaagc tgatattcgc atcaacggct gggcagttga atgtcgggtt 1200
tatgctgagg accccctacaa gtcttttggt ttaccatcta ttgggagatt gtctcagtac 1260
caagaaccgt tacatctacc tggtgtccga gtggacagtg gcatccaacc aggaagtgat 1320
attagcattt attatgatcc tatgatttca aaactaatca catatggctc tgatagaact 1380
gaggcactga agagaatggc agatgcactg gataactatg ttattcgagg tgttacacat 1440
aatattgcat tacttcgaga ggtgataatc aactcacgct ttgtaaaagg agacatcagc 1500
actaaatttc tctccgatgt gtatcctgat ggcttcaaag gacacatgct aaccaagagt 1560
gagaagaacc agttattggc aatagcatca tcattgtttg tggcattcca gttaagagca 1620
caacattttc aagaaaattc aagaatgcct gttattaaac cagacatagc caactgggag 1680
ctctcagtaa aattgcatga taaagttcat accgtagtag catcaaacaa tgggtcagtg 1740
ttctcggtgg aagttgatgg gtcgaaacta aatgtgacca gcacgtggaa cctggcttcg 1800
cccttattgt ctgtcagcgt tgatggcact cagaggactg tccagtgtct ttctcgagaa 1860
gcaggtggaa acatgagcat tcagtttctt ggtacagtgt acaaggtgaa tatcttaacc 1920
agacttgccg cagaattgaa caaatttatg ctggaaaaag tgactgagga cacaagcagt 1980
gttctgcgtt ccccgatgcc cggagtggtg gtggccgtct ctgtcaagcc tggagacgcg 2040
gtagcagaag gtcaagaaat ttgtgtgatt gaagccatga aaatgcagaa tagtatgaca 2100
gctgggaaaa ctggcacggt gaaatctgtg cactgtcaag ctggagacac agttggagaa 2160
ggggatctgc tcgtggagct ggaa 2184

<210> SEQ ID NO 3
<211> LENGTH: 2184
<212> TYPE: DNA
<213> ORGANISM: Artificial Sequence
<220> FEATURE:
<223> OTHER INFORMATION: Description of Artificial Sequence: PCCA Coding Sequence - Codon-Optimized

<400> SEQUENCE: 3
atggctggat tttgggtcgg aacggcccct ctcgtggccg ccggccgccg gggtcggtgg 60
ccgccgcaac agctgatgtt gtcggccgcg ctgcgcaccc ttaagcatgt gctgtactac 120
tcccggcaat gccttatggt gtccagaaac ctgggtagcg tgggctatga cccgaacgag 180
aaaaccttcg acaagattct ggtggccaac cgggggggaaa ttgcctgccg ggtcatcagg 240
acttgcaaga agatgggcat caagaccgtc gccattcact ccgacgtgga cgcctcctcc 300
gtgcacgtga agatggcaga tgaagccgtc tgcgtgggcc ccgcccccgac ctccaagtcc 360 taccttaaca tggacgcgat catggaagcc atcaaaaaga ccagagccca ggcagtgcac 420
ccgggatacg gctttctctc cgaaaacaag gagttcgcgc ggtgcctggc cgctgaagat 480
gtcgtgttca tcggccctga tacccacgcg atccaggcta tgggagacaa gatcgaatcc 540
aagctgctcg ccaagaaagc cgaagtcaac accatacctg ggtttgacgg cgtggtcaag 600
gacgcagaag aagccgtcag gattgcccgc gagatcggat accccgtgat gatcaaggca 660
tccgccgggg ggggaggaaa gggaatgcgc atcgcctggg atgacgaaga aacccgggac 720
ggcttcagac tctcgtcaca agaggccgcg tcctcattcg gggatgaccg gctcctgatt 780
gagaagttca ttgacaatcc tcggcacatc gagattcagg tcctgggcga taagcatgga 840
aacgccctgt ggctgaacga acgcgaatgc agcatccaga ggcggaacca gaaagtggtg 900
gaagaggccc catccatctt tctcgacgcc gagactcgga gagcgatggg tgaacaggcc 960
gtggccctgg cccgagccgt gaagtactcc agcgcgggga ctgtcgagtt cctggtggac 1020
agcaagaaga atttctactt cctggagatg aatactcggc tccaagtgga acaccccgtg 1080
accgaatgca ttaccggtct ggacctcgtc caagaaatga tccgcgtcgc caagggctac 1140
ccattgagac acaaacaggc cgacattcgg atcaacggat gggccgtcga gtgtcgcgtg 1200
tacgcggaag atccgtataa gtcgttcgga ctgccgtcca ttggtagact ctcgcagtac 1260
caagagccac tgcacctccc cggagtgcgc gtggactcag gcatccagcc cggaagcgac 1320
atctctatct actacgaccc catgatttcc aagttgatca cctacgggtc cgataggacc 1380
gaggcactga agcgcatggc tgacgcactt gacaactacg tgatccgcgg ggtcactcac 1440
aacattgccc tgctccgcga agtgatcatc aactcgcgct tcgtgaaggg cgacatctcc 1500
actaagttcc tgtccgacgt gtaccctgac ggtttcaagg gccatatgct gaccaagtcc 1560
gagaagaacc agctcctggc tatcgcctcc tccctgtttg tggcgttcca gctgagggcg 1620
cagcacttcc aggagaacag ccggatgccc gtgatcaagc ctgacatcgc caattgggag 1680

```
ctgtccgtga agctgcacga taaggtccat accgtggtgg catccaacaa cggatcggtg   1740

ttcagcgtgg aagtggacgg gtccaagctg aacgtgacca gcacatggaa cctggcgtcc   1800

cccctgttgt ctgtgtcggt cgatggcacg cagcgcactg tgcagtgcct ctcccgggaa   1860

gctggcggaa acatgagcat ccagttcctg ggtactgtgt acaaggtcaa cattctgact   1920

cggctggccg ccgagctgaa caagttcatg ttggaaaaag tcaccgaaga tacatcgtca   1980

gtcctgcgga gcccaatgcc tggagtcgtg gtggcggtgt cagtgaagcc cggcgatgct   2040

gtggccgaag gccaagagat ctgcgtgatc gaggccatga agatgcagaa ctcgatgacc   2100

gccggaaaga ccggtaccgt gaagtccgtg cattgtcaag cgggcgacac tgtgggagag   2160

ggagatctgc tcgtggagct ggag                                          2184
```

<210> SEQ ID NO 4
<211> LENGTH: 2184
<212> TYPE: DNA
<213> ORGANISM: Artificial Sequence
<220> FEATURE:
<223> OTHER INFORMATION: Description of Artificial Sequence: PCCA Coding Sequence - Codon-Optimized

<400> SEQUENCE: 4

```
atggccggct tctgggtcgg caccgcccct ctggtcgcgg ccggacgacg cggacgctgg     60

ccaccccagc aactgatgct gagcgcggcc ttgaggactc tgaagcacgt gctctactac    120

tcgcggcagt gcctgatggt gtcccggaat ctggggtccg tgggatacga ccctaacgaa    180

aagaccttcg ataagatcct cgtggcaaat cggggagaga tcgcgtgtcg cgtgatccgc    240

acgtgcaaga agatggggat caagactgtg gcaatccata gcgatgtgga tgcatcctcg    300

gtccacgtga agatggccga cgaagctgtg tgcgtgggac cggcgccgac ttcgaaatcg    360

tacctgaaca tggacgctat tatggaggcg atcaagaaaa cgcgcgccca agcggtccat    420

cccggttacg gattcctgag cgagaacaag gaatttgcac ggtgcctcgc tgccgaggac    480

gtggtgttta tcggtcccga cacccacgcc atccaagcta tgggggacaa gattgagtcc    540

aagctcctgg cgaaaaaggc agaggtcaac acaattcctg gtttcgacgg cgtcgtgaag    600

gacgccgaag aagccgtgcg catcgcgagg gaaatcggtt accctgtgat gattaaggcc    660

tccgccggcg gcggtggaaa gggaatgaga attgcctggg acgatgaaga aacccgcgac    720

ggattccgcc tgtcgagcca ggaagccgcc tcttccttcg gcgatgacag actgctgatc    780

gaaaagttca tcgataaccc cagacacatt gagatccaag tgctcgggga taagcacggc    840

aacgcccttt ggctgaacga gagagagtgc tccattcaac gccgcaatca gaaggtcgtg    900

gaggaagccc cgtcgatatt cctggatgcc gaaacccggc gggccatggg agagcaggct    960

gtcgcgttgg cgcgggccgt caagtacagc tcggccggga ccgtggaatt tctggtcgat   1020

tccaagaaga acttctattt cctggagatg aacaccagac tccaggtcga gcacccggtc   1080

actgagtgta tcaccgggct cgatctggtg caagagatga ttcgggtggc gaagggatat   1140

ccccttcggc ataaacaagc cgacatcagg atcaacggtt gggccgtgga atgcagggtc   1200

tacgccgagg acccctacaa gagcttcggc ctgcccagca tcggccgcct gtcacagtat   1260

caggaaccgc tgcatcttcc gggcgtgcgg gtcgacagcg gaattcagcc tggctcagat   1320

atctccatct actacgatcc aatgatctca aagctgatta cttatggatc cgaccggacc   1380

gaagccctta agcgaatggc cgacgccctg gacaactacg tgatccgggg agtgacccac   1440

aacatcgcct tgctgcggga agtgatcatt aacagcagat tcgtgaaggg agacatcagc   1500
```

-continued

```
accaagttcc tgtcggatgt ctacccggac gggttcaaag ggcacatgct tactaagtcc   1560

gagaagaatc agctgctcgc cattgcgtca agcttgttcg tggcctttca actccgggcc   1620

cagcacttcc aggaaaactc ccgcatgcca gtcattaagc cggacatcgc caactgggaa   1680

ctcagcgtga agctccatga caaagtgcat accgtggtgg ccagcaacaa cggtagcgtg   1740

ttctcagtcg aggtcgatgg ctcgaagctc aacgtcactt ccacttggaa cttggccagc   1800

ccgctgctgt ccgtgtccgt ggacggaacc cagaggaccg tgcagtgtct gtcgagagaa   1860

gccggcggca acatgtcaat ccagttcctg ggaaccgtgt acaaggtcaa catcctgacc   1920

agactggccg ccgaactgaa caagtttatg ctcgagaaag tgaccgagga cactagctcc   1980

gtgctgcgct cccctatgcc cggagtggtc gtggcagtgt ccgtgaagcc gggcgacgcc   2040

gtggccgagg gacaggaaat ctgtgtgatc gaagcgatga agatgcagaa ttcaatgacc   2100

gcgggaaaga ctgggaccgt gaagtctgtg cactgccagg ctggcgatac cgtgggggag   2160

ggcgaccttc tggtggaact cgag                                          2184
```

<210> SEQ ID NO 5
<211> LENGTH: 2184
<212> TYPE: DNA
<213> ORGANISM: Artificial Sequence
<220> FEATURE:
<223> OTHER INFORMATION: Description of Artificial Sequence: PCCA Coding Sequence - Codon-Optimized

<400> SEQUENCE: 5

```
atggctgggt tttgggtggg gacagctcct ctggtggctg ctgggaggag ggggaggtgg     60

cctcctcagc agctgatgct gtctgctgct ctgaggacac tgaagcatgt gctgtattat    120

tctaggcagt gtctgatggt gtctaggaat ctggggtctg tggggtatga tcctaatgag    180

aagacatttg ataagattct ggtggctaat agggggggaga ttgcttgtag ggtgattagg    240

acatgtaaga agatggggat taagacagtg gctattcatt ctgatgtgga tgcttcttct    300

gtgcatgtga agatggctga tgaggctgtg tgtgtggggc ctgctcctac atctaagtct    360

tatctgaata tggatgctat tatggaggct attaagaaga caagggctca ggctgtgcat    420

cctgggtatg ggtttctgtc tgagaataag gagtttgcta ggtgtctggc tgctgaggat    480

gtggtgttta ttgggcctga tacacatgct attcaggcta tgggggataa gattgagtct    540

aagctgctgg ctaagaaggc tgaggtgaat acaattcctg ggtttgatgg ggtggtgaag    600

gatgctgagg aggctgtgag gattgctagg gagattgggt atcctgtgat gattaaggct    660

tctgctgggg gggggggaa ggggatgagg attgcttggg atgatgagga gacaagggat    720

gggtttaggc tgtcttctca ggaggctgct tcttcttttg ggatgatag gctgctgatt    780

gagaagttta ttgataatcc taggcatatt gagattcagg tgctgggga taagcatggg    840

aatgctctgt ggctgaatga gagggagtgt tctattcaga ggaggaatca gaaggtggtg    900

gaggaggctc cttctatttt tctggatgct gagacaagga gggctatggg ggagcaggct    960

gtggctctgg ctagggctgt gaagtattct tctgctggga cagtggagtt tctggtggat   1020

tctaagaaga atttttattt tctggagatg aatacaaggc tgcaggtgga gcatcctgtg   1080

acagagtgta ttacagggct ggatctggtg caggagatga ttagggtggc taaggggtat   1140

cctctgaggc ataagcaggc tgatattagg attaatgggt gggctgtgga gtgtagggtg   1200

tatgctgagg atccttataa gtcttttggg ctgccttcta ttgggaggct gtctcagtat   1260

caggagcctc tgcatctgcc tggggtgagg gtggattctg ggattcagcc tgggtctgat   1320
```

```
atttctattt attatgatcc tatgatttct aagctgatta catatgggtc tgataggaca   1380

gaggctctga agaggatggc tgatgctctg gataattatg tgattagggg ggtgacacat   1440

aatattgctc tgctgaggga ggtgattatt aattctaggt ttgtgaaggg ggatatttct   1500

acaaagtttc tgtctgatgt gtatcctgat gggtttaagg ggcatatgct gacaaagtct   1560

gagaagaatc agctgctggc tattgcttct tctctgtttg tggcttttca gctgagggct   1620

cagcattttc aggagaattc taggatgcct gtgattaagc ctgatattgc taattgggag   1680

ctgtctgtga agctgcatga taaggtgcat acagtggtgg cttctaataa tgggtctgtg   1740

ttttctgtgg aggtggatgg gtctaagctg aatgtgacat ctacatggaa tctggcttct   1800

cctctgctgt ctgtgtctgt ggatgggaca cagaggacag tgcagtgtct gtctagggag   1860

gctgggggga atatgtctat tcagtttctg gggacagtgt ataaggtgaa tattctgaca   1920

aggctggctg ctgagctgaa taagtttatg ctggagaagg tgacagagga tacatcttct   1980

gtgctgaggt ctcctatgcc tggggtggtg gtggctgtgt ctgtgaagcc tggggatgct   2040

gtggctgagg ggcaggagat ttgtgtgatt gaggctatga agatgcagaa ttctatgaca   2100

gctgggaaga cagggacagt gaagtctgtg cattgtcagg ctggggatac agtgggggag   2160

ggggatctgc tggtggagct ggag                                          2184
```

```
<210> SEQ ID NO 6
<211> LENGTH: 2184
<212> TYPE: DNA
<213> ORGANISM: Artificial Sequence
<220> FEATURE:
<223> OTHER INFORMATION: Description of Artificial Sequence: PCCA Coding
      Sequence - Codon-Optimized

<400> SEQUENCE: 6
```

```
atggcagggt tttgggtggg gacagcacca ctggtggcag cagggaggag ggggaggtgg     60

ccaccacagc agctgatgct gtcagcagca ctgaggacac tgaagcatgt gctgtattat    120

tcaaggcagt gtctgatggt gtcaaggaat ctggggtcag tggggtatga tccaaatgag    180

aagacatttg ataagattct ggtggcaaat aggggggaga ttgcatgtag ggtgattagg    240

acatgtaaga agatggggat taagacagtg gcaattcatt cagatgtgga tgcatcatca    300

gtgcatgtga agatggcaga tgaggcagtg tgtgtggggc cagcaccaac atcaaagtca    360

tatctgaata tggatgcaat tatggaggca attaagaaga caagggcaca ggcagtgcat    420

ccagggtatg ggtttctgtc agagaataag gagtttgcaa ggtgtctggc agcagaggat    480

gtggtgttta ttgggccaga tacacatgca attcaggcaa tgggggataa gattgagtca    540

aagctgctgg caaagaaggc agaggtgaat acaattccag ggtttgatgg ggtggtgaag    600

gatgcagagg aggcagtgag gattgcaagg gagattgggt atccagtgat gattaaggca    660

tcagcagggg gggggggaa ggggatgagg attgcatggg atgatgagga gacaagggat    720

gggtttaggc tgtcatcaca ggaggcagca tcatcatttg ggatgatag gctgctgatt    780

gagaagttta ttgataatcc aaggcatatt gagattcagg tgctggggga taagcatggg    840

aatgcactgt ggctgaatga gagggagtgt tcaattcaga ggaggaatca gaaggtggtg    900

gaggaggcac catcaatttt tctggatgca gagacaagga gggcaatggg ggagcaggca    960

gtggcactgg caagggcagt gaagtattca tcagcaggga cagtggagtt tctggtggat   1020

tcaaagaaga atttttattt tctggagatg aatacaaggc tgcaggtgga gcatccagtg   1080

acagagtgta ttacagggct ggatctggtg caggagatga ttagggtggc aaaggggtat   1140
```

-continued

```
ccactgaggc ataagcaggc agatattagg attaatgggt gggcagtgga gtgtagggtg   1200

tatgcagagg atccatataa gtcatttggg ctgccatcaa ttgggaggct gtcacagtat   1260

caggagccac tgcatctgcc aggggtgagg gtggattcag ggattcagcc agggtcagat   1320

atttcaattt attatgatcc aatgatttca aagctgatta catatgggtc agataggaca   1380

gaggcactga agaggatggc agatgcactg gataattatg tgattagggg ggtgacacat   1440

aatattgcac tgctgaggga ggtgattatt aattcaaggt ttgtgaaggg ggatatttca   1500

acaaagtttc tgtcagatgt gtatccagat gggtttaagg ggcatatgct gacaaagtca   1560

gagaagaatc agctgctggc aattgcatca tcactgtttg tggcatttca gctgagggca   1620

cagcattttc aggagaattc aaggatgcca gtgattaagc cagatattgc aaattgggag   1680

ctgtcagtga agctgcatga taaggtgcat acagtggtgg catcaaataa tgggtcagtg   1740

ttttcagtgg aggtggatgg gtcaaagctg aatgtgacat caacatggaa tctggcatca   1800

ccactgctgt cagtgtcagt ggatgggaca cagaggacag tgcagtgtct gtcaagggag   1860

gcaggggga atatgtcaat tcagtttctg ggacagtgt ataaggtgaa tattctgaca   1920

aggctggcag cagagctgaa taagtttatg ctggagaagg tgacagagga tacatcatca   1980

gtgctgaggt caccaatgcc aggggtggtg gtggcagtgt cagtgaagcc aggggatgca   2040

gtggcagagg ggcaggagat ttgtgtgatt gaggcaatga agatgcagaa ttcaatgaca   2100

gcagggaaga cagggacagt gaagtcagtg cattgtcagg caggggatac agtgggggag   2160

ggggatctgc tggtggagct ggag                                          2184
```

<210> SEQ ID NO 7
<211> LENGTH: 2184
<212> TYPE: DNA
<213> ORGANISM: Artificial Sequence
<220> FEATURE:
<223> OTHER INFORMATION: Description of Artificial Sequence: PCCA Coding Sequence - Codon-Optimized

<400> SEQUENCE: 7

```
atggctggtt tttgggtagg tacagcacca ctagtagcag caggtaggag ggtaggtgg      60

ccaccacaac aactaatgct atcagcagca ctaaggacac taaagcatgt actatattat    120

tcaaggcaat gtctaatggt atcaaggaat ctggggtctg tggggtatga tcctaatgag    180

aagacatttg ataagattct ggtggctaat agggggggaga ttgcttgtag ggtgattagg    240

acatgtaaga agatggggat taagacagtg gctattcatt ctgatgtgga tgcttcttct    300

gtgcatgtga agatggctga tgaggctgtg tgtgtggggc ctgctcctac atctaagtct    360

tatctgaata tggatgctat tatggaggct attaagaaga caagggctca ggctgtgcat    420

cctgggtatg ggtttctgtc tgagaataag gagtttgcta ggtgtctggc tgctgaggat    480

gtggtgttta ttgggcctga tacacatgct attcaggcta tgggggataa gattgagtct    540

aagctgctgg ctaagaaggc tgaggtgaat acaattcctg ggtttgatgg ggtggtgaag    600

gatgctgagg aggctgtgag gattgctagg gagattgggt atcctgtgat gattaaggct    660

tctgctgggg ggggggggaa ggggatgagg attgcttggg atgatgagga gacaagggat    720

gggtttaggc tgtcttctca ggaggctgct tcttcttttg gggatgatag gctgctgatt    780

gagaagttta ttgataatcc taggcatatt gagattcagg tgctggggga taagcatggg    840

aatgctctgt ggctgaatga gagggagtgt tctattcaga ggaggaatca gaaggtggtg    900

gaggaggctc cttctatttt tctggatgct gagacaagga gggctatggg ggagcaggct    960
```

```
gtggctctgg ctagggctgt gaagtattct tctgctggga cagtggagtt tctggtggat   1020

tctaagaaga atttttattt tctggagatg aatacaaggc tgcaggtgga gcatcctgtg   1080

acagagtgta ttacagggct ggatctggtg caggagatga ttagggtggc taaggggtat   1140

cctctgaggc ataagcaggc tgatattagg attaatgggt gggctgtgga gtgtagggtg   1200

tatgctgagg atccttataa gtcttttggg ctgccttcta ttgggaggct gtctcagtat   1260

caggagcctc tgcatctgcc tggggtgagg gtggattctg ggattcagcc tgggtctgat   1320

atttctattt attatgatcc tatgatttct aagctgatta catatgggtc tgataggaca   1380

gaggctctga agaggatggc tgatgctctg gataattatg tgattagggg ggtgacacat   1440

aatattgctc tgctgaggga ggtgattatt aattctaggt ttgtgaaggg ggatatttct   1500

acaaagtttc tgtctgatgt gtatcctgat gggtttaagg ggcatatgct gacaaagtct   1560

gagaagaatc agctgctggc tattgcttct tctctgtttg tggcttttca gctgagggct   1620

cagcattttc aggagaattc taggatgcct gtgattaagc ctgatattgc taattgggag   1680

ctgtctgtga agctgcatga taaggtgcat acagtggtgg cttctaataa tgggtctgtg   1740

ttttctgtgg aggtggatgg gtctaagctg aatgtgacat ctacatggaa tctggcttct   1800

cctctgctgt ctgtgtctgt ggatgggaca cagaggacag tgcagtgtct gtctagggag   1860

gctgggggga atatgtctat tcagtttctg ggacagtgt ataaggtgaa tattctgaca   1920

aggctggctg ctgagctgaa taagtttatg ctggagaagg tgacagagga tacatcttct   1980

gtgctgaggt ctcctatgcc tggggtggtg gtggctgtgt ctgtgaagcc tggggatgct   2040

gtggctgagg ggcaggagat ttgtgtgatt gaggctatga agatgcagaa ttctatgaca   2100

gctgggaaga cagggacagt gaagtctgtg cattgtcagg ctggggatac agtgggggag   2160

ggggatctgc tggtggagct ggag                                          2184
```

<210> SEQ ID NO 8
<211> LENGTH: 1617
<212> TYPE: DNA
<213> ORGANISM: Homo sapiens
<220> FEATURE:
<221> NAME/KEY: misc_feature
<222> LOCATION: (1)..(1617)
<223> OTHER INFORMATION: PCCB Coding Sequence - Wild-Type

<400> SEQUENCE: 8

```
atggcggcgg cattacgggt ggcggcggtc ggggcaaggc tcagcgttct ggcgagcggt     60

ctccgcgccg cggtccgcag cctttgcagc caggccacct ctgttaacga acgcatcgaa    120

aacaagcgcc ggaccgcgct gctgggaggg ggccaacgcc gtattgacgc gcagcacaag    180

cgaggaaagc taacagccag ggagaggatc agtctcttgc tggaccctgg cagctttgtt    240

gagagcgaca tgtttgtgga acacagatgt gcagattttg gaatggctgc tgataagaat    300

aagtttcctg gagacagcgt ggtcactgga cgaggccgaa tcaatggaag attggtttat    360

gtcttcagtc aggattttac agtttttgga ggcagtctgt caggagcaca tgcccaaaag    420

atctgcaaaa tcatggacca ggccataacg gtgggggctc cagtgattgg gctgaatgac    480

tctgggggag cacggatcca agaaggagtg gagtctttgg ctggctatgc agacatcttt    540

ctgaggaatg ttacggcatc cggagtcatc cctcagattt ctctgatcat gggcccatgt    600

gctggtgggg ccgtctactc cccagcccta acagacttca cgttcatggt aaaggacacc    660

tcctacctgt tcatcactgg ccctgatgtt gtgaagtctg tcaccaatga ggatgttacc    720

caggaggagc tcggtggtgc caagacccac accaccatgt caggtgtggc ccacagagct    780
```

```
tttgaaaatg atgttgatgc cttgtgtaat ctccgggatt tcttcaacta cctgcccctg    840
agcagtcagg acccggctcc cgtccgtgag tgccacgatc ccagtgaccg tctggttcct    900
gagcttgaca caattgtccc tttggaatca accaaagcct acaacatggt ggacatcata    960
cactctgttg ttgatgagcg tgaatttttt gagatcatgc ccaattatgc caagaacatc   1020
attgttggtt ttgcaagaat gaatgggagg actgttggaa ttgttggcaa ccaacctaag   1080
gtggcctcag gatgcttgga tattaattca tctgtgaaag gggctcgttt tgtcagattc   1140
tgtgatgcat tcaatattcc actcatcact tttgttgatg tccctggctt tctacctggc   1200
acagcacagg aatacggggg catcatccgg catggtgcca agcttctcta cgcatttgct   1260
gaggcaactg tacccaaagt cacagtcatc accaggaagg cctatggagg tgcctatgat   1320
gtcatgagct ctaagcacct ttgtggtgat accaactatg cctggcccac cgcagagatt   1380
gcagtcatgg gagcaaaggg cgctgtggag atcatcttca aagggcatga gaatgtggaa   1440
gctgctcagg cagagtacat cgagaagttt gccaaccctt tccctgcagc agtgcgaggg   1500
tttgtggatg acatcatcca accttcttcc acacgtgccc gaatctgctg tgacctggat   1560
gtcttggcca gcaagaaggt acaacgtcct tggagaaaac atgcaaatat tccattg      1617
```

<210> SEQ ID NO 9
<211> LENGTH: 1617
<212> TYPE: DNA
<213> ORGANISM: Artificial Sequence
<220> FEATURE:
<223> OTHER INFORMATION: Description of Artificial Sequence: PCCB Coding Sequence - Codon-Optimized

<400> SEQUENCE: 9

```
atggctgccg ccctgcgcgt ggcggccgtg ggagcaagac tgtccgtgct ggcgtcgggc     60
ttgagagcgg ccgtgcggag cctgtgctca caagcaacct cggtgaacga acgcatcgag    120
aacaagcgca ggactgcgct gctgggcggg ggccagcgca ggatcgacgc acagcataag    180
cgcggaaagc tgaccgcccg cgagcggatt tccctgctcc tggatcctgg aagcttcgtg    240
gagtccgaca tgttcgtgga gcaccgctgc gccgacttcg ggatggctgc cgacaagaac    300
aagttccccg gggactcagt ggtcactggt cgcggaagaa tcaatggccg gctcgtctac    360
gtgttctcac aagactttac tgtgttcggc ggctccctgt cgggagccca cgcgcaaaag    420
atctgcaaga ttatggatca ggccatcact gtgggagcgc ctgtgattgg actcaacgac    480
tccgggggag caagaatcca ggaaggagtg gaaagccttg ccggctacgc tgacatcttc    540
ctccggaacg tgaccgcctc tggagtgatt ccgcaaatct ccctgatcat gggaccatgt    600
gccgggggcg ccgtgtactc ccggcgctg actgacttca ctttcatggt caaggacaca    660
tcctacctgt tcatcaccgg tcccgacgtc gtgaagtccg tgaccaacga ggatgtgacc    720
caggaagaac tgggggggc caagacgcat accaccatgt cgggagtggc ccaccgggcc    780
ttcgagaacg atgtggacgc cttgtgcaac cttcgggact tcttcaatta tctcccgctg    840
agcagccagg atccggcccc agtgcgggaa tgccacgacc cttcggatcg gttggtgcct    900
gagctggata ccatcgtgcc cctcgaatcc accaaggctt acaacatggt cgacatcatt    960
cactccgtgg tggacgagag ggaattcttc gagattatgc cgaactacgc caagaacatc   1020
attgtcggat tcgcccgcat gaacggtcga actgtgggca ttgtcggaaa ccagcctaaa   1080
gtggcctccg gttgcctgga catcaactca agcgtgaagg gtgccagatt tgtgcggttt   1140
tgtgacgcgt tcaatattcc gctgatcacc ttcgtcgacg tcccgggctt cctgcctggg   1200
```

```
accgcccagg aatacggcgg catcatcaga cacggcgcga agctcctcta cgcgttcgcg   1260

gaagccaccg tgcccaaggt caccgtgatc actcgcaagg catacggcgg cgcatacgat   1320

gtgatgtcct ccaagcacct gtgtggcgac accaactacg cctggcccac cgccgagatc   1380

gccgtgatgg gtgccaaggg tgctgtcgag atcatcttca agggacatga aaacgtggaa   1440

gctgcccagg ccgagtacat tgaaaagttc gctaacccct tccctgccgc cgtgcgggga   1500

tttgtggatg acattatcca gccgagctcg accagggcca gaatctgctg cgatcttgat   1560

gtgttggcca gcaaaaaggt ccagcggccc tggcggaaac acgccaacat tccactg      1617
```

```
<210> SEQ ID NO 10
<211> LENGTH: 1617
<212> TYPE: DNA
<213> ORGANISM: Artificial Sequence
<220> FEATURE:
<223> OTHER INFORMATION: Description of Artificial Sequence: PCCB Coding
      Sequence - Codon-Optimized

<400> SEQUENCE: 10
```

```
atggccgcgg cgcttagagt ggccgctgtg ggagccaggc tgagcgtgct ggccagcggt     60

ctgcgcgccg cagtgcgctc gctgtgtagc caggctacct ccgtgaatga gcggatcgaa    120

aacaagcggc gcaccgccct gttgggcggc ggacagcggc gaattgacgc ccaacacaag    180

cggggaaagc tcactgcgag ggaaagaatc tcactgctgc tcgaccccgg gtcgttcgtg    240

gaatcggata tgtttgtcga acatagatgc gcagatttcg gaatggccgc tgacaagaac    300

aagttcccgg gagattccgt cgtgaccgga agggggcgca ttaacgggag acttgtgtac    360

gtgttcagcc aggatttcac ggtgttcggc ggatcactga gcggtgcaca tgcacagaag    420

atctgcaaga tcatggacca ggccattacc gtcggggcac ctgtgatcgg cctgaatgat    480

tcgggcggag cccggattca agagggcgtg gagtcactcg cgggttacgc cgacattttc    540

ctgcggaacg tcaccgcctc cggcgtgatc cctcaaatca gcctcattat gggcccctgc    600

gcgggcggtg ccgtctactc acccgctctg accgatttta ccttcatggt caaggacacc    660

tcctatctgt ttatcactgg accagatgtg gtcaagtccg tgaccaacga ggacgtcact    720

caggaagaac tcggtggagc aaagacccac actactatgt ccggggtcgc gcatagagct    780

ttcgaaaacg acgtcgatgc tctctgtaac ctgagggatt tcttcaacta ccttccactg    840

tcgtcgcaag acccagcccc cgtgcgcgag tgccacgatc cctccgaccg cctggtgccg    900

gaactcgaca ctattgtccc tctggagtca accaaggcct acaacatggt ggacatcatc    960

catagcgtcg tggatgaacg ggagttcttc gaaatcatgc ccaactatgc gaaaaatatc   1020

atcgtgggct ttgcgcggat gaacggccgc accgtgggca tagtgggcaa ccagccgaag   1080

gtcgcgtcgg gatgcctcga tatcaacagc tctgtgaagg gagcgcggtt cgtgcgcttc   1140

tgcgacgcct tcaacatccc cttgatcacc ttcgtggatg tgcctgggtt cttgcctgga   1200

accgcccagg aatacggggg gatcattcgg cacggagcaa aactgctgta cgccttcgcc   1260

gaggccactg tgccgaaagt gacagtgatt acccggaagg cctacggggg tgcctacgac   1320

gtgatgagct ccaagcacct gtgcggagac accaattacg cgtggcctac tgctgaaatt   1380

gctgtcatgg gagccaaggg cgccgtggaa atcattttca agggccacga aaacgtcgag   1440

gccgcccaag ctgagtacat cgagaagttt gccaacccgt ttcctgcggc tgtgcgcggc   1500

ttcgtcgacg atatcattca gccctcgtcc actcgcgccc gcatttgttg tgacctcgac   1560

gtgctggcgt ccaagaaagt gcaaagaccg tggagaaagc atgcaaacat cccgctc      1617
```

```
<210> SEQ ID NO 11
<211> LENGTH: 1617
<212> TYPE: DNA
<213> ORGANISM: Artificial Sequence
<220> FEATURE:
<223> OTHER INFORMATION: Description of Artificial Sequence: PCCB Coding
      Sequence - Codon-Optimized

<400> SEQUENCE: 11

atggctgctg ctctgagggt ggctgctgtg gggctaggc tgtctgtgct ggcttctggg     60

ctgagggctg ctgtgaggtc tctgtgttct caggctacat ctgtgaatga gaggattgag    120

aataagagga ggacagctct gctgggggg gggcagagga ggattgatgc tcagcataag    180

agggggaagc tgacagctag ggagaggatt tctctgctgc tggatcctgg gtcttttgtg    240

gagtctgata tgtttgtgga gcataggtgt gctgattttg ggatggctgc tgataagaat    300

aagtttcctg ggattctgt ggtgacaggg agggggagga ttaatgggag gctggtgtat    360

gtgttttctc aggattttac agtgtttggg ggtctctgt ctggggctca tgctcagaag    420

atttgtaaga ttatggatca ggctattaca gtgggggctc ctgtgattgg gctgaatgat    480

tctgggggg ctaggattca ggagggggtg gagtctctgg ctgggtatgc tgatattttt    540

ctgaggaatg tgacagcttc tggggtgatt cctcagattt ctctgattat ggggccttgt    600

gctgggggg ctgtgtattc tcctgctctg acagatttta catttatggt gaaggataca    660

tcttatctgt ttattacagg gcctgatgtg gtgaagtctg tgacaaatga ggatgtgaca    720

caggaggagc tgggggggc taagacacat acaacaatgt ctggggtggc tcatagggct    780

tttgagaatg atgtggatgc tctgtgtaat ctgagggatt tttttaatta tctgcctctg    840

tcttctcagg atcctgctcc tgtgagggag tgtcatgatc cttctgatag gctggtgcct    900

gagctggata caattgtgcc tctggagtct acaaaggctt ataatatggt ggatattatt    960

cattctgtgg tggatgagag ggagtttttt gagattatgc ctaattatgc taagaatatt   1020

attgtggggt ttgctaggat gaatgggagg acagtgggga ttgtggggaa tcagcctaag   1080

gtggcttctg ggtgtctgga tattaattct tctgtgaagg gggctaggtt tgtgaggttt   1140

tgtgatgctt ttaatattcc tctgattaca tttgtggatg tgcctgggtt tctgcctggg   1200

acagctcagg agtatgggg gattattagg catggggcta agctgctgta tgcttttgct   1260

gaggctacag tgcctaaggt gacagtgatt acaaggaagg cttatggggg ggcttatgat   1320

gtgatgtctt ctaagcatct gtgtggggat acaaattatg cttggcctac agctgagatt   1380

gctgtgatgg gggctaaggg ggctgtggag attattttta aggggcatga gaatgtggag   1440

gctgctcagg ctgagtatat tgagaagttt gctaatcctt ttcctgctgc tgtgaggggg   1500

tttgtggatg atattattca gccttcttct acaagggcta ggatttgttg tgatctggat   1560

gtgctggctt ctaagaaggt gcagaggcct tggaggaagc atgctaatat tcctctg      1617


<210> SEQ ID NO 12
<211> LENGTH: 1617
<212> TYPE: DNA
<213> ORGANISM: Artificial Sequence
<220> FEATURE:
<223> OTHER INFORMATION: Description of Artificial Sequence: PCCB Coding
      Sequence - Codon-Optimized

<400> SEQUENCE: 12

atggcagcag cactgagggt ggcagcagtg gggcaaggc tgtcagtgct ggcatcaggg     60
```

-continued

```
ctgagggcag cagtgaggtc actgtgttca caggcaacat cagtgaatga gaggattgag    120

aataagagga ggacagcact gctggggggg gggcagagga ggattgatgc acagcataag    180

agggggaagc tgacagcaag ggagaggatt tcactgctgc tggatccagg gtcatttgtg    240

gagtcagata tgtttgtgga gcataggtgt gcagattttg ggatggcagc agataagaat    300

aagtttccag gggattcagt ggtgacaggg agggggagga ttaatgggag gctggtgtat    360

gtgttttcac aggattttac agtgtttggg gggtcactgt caggggcaca tgcacagaag    420

atttgtaaga ttatggatca ggcaattaca gtgggggcac cagtgattgg gctgaatgat    480

tcaggggggg caaggattca ggagggggtg gagtcactgg cagggtatgc agatattttt    540

ctgaggaatg tgacagcatc aggggtgatt ccacagattt cactgattat ggggccatgt    600

gcaggggggg cagtgtattc accagcactg acagatttta catttatggt gaaggataca    660

tcatatctgt ttattacagg gccagatgtg gtgaagtcag tgacaaatga ggatgtgaca    720

caggaggagc tgggggggc aaagacacat acaacaatgt caggggtggc acatagggca    780

tttgagaatg atgtggatgc actgtgtaat ctgagggatt tttttaatta tctgccactg    840

tcatcacagg atccagcacc agtgagggag tgtcatgatc catcagatag gctggtgcca    900

gagctggata caattgtgcc actggagtca acaaaggcat ataatatggt ggatattatt    960

cattcagtgg tggatgagag ggagtttttt gagattatgc caaattatgc aaagaatatt   1020

attgtggggt ttgcaaggat gaatgggagg acagtgggga ttgtggggaa tcagccaaag   1080

gtggcatcag ggtgtctgga tattaattca tcagtgaagg gggcaaggtt tgtgaggttt   1140

tgtgatgcat ttaatattcc actgattaca tttgtggatg tgccagggtt tctgccaggg   1200

acagcacagg agtatggggg gattattagg catggggcaa agctgctgta tgcatttgca   1260

gaggcaacag tgccaaaggt gacagtgatt acaaggaagg catatggggg ggcatatgat   1320

gtgatgtcat caaagcatct gtgtggggat acaaattatg catggccaac agcagagatt   1380

gcagtgatgg gggcaaaggg ggcagtggag attatttta aggggcatga gaatgtggag   1440

gcagcacagg cagagtatat tgagaagttt gcaaatccat ttccagcagc agtgaggggg   1500

tttgtggatg atattattca gccatcatca acaagggcaa ggatttgttg tgatctggat   1560

gtgctggcat caaagaaggt gcagaggcca tggaggaagc atgcaaatat tccactg      1617
```

<210> SEQ ID NO 13
<211> LENGTH: 1617
<212> TYPE: DNA
<213> ORGANISM: Artificial Sequence
<220> FEATURE:
<223> OTHER INFORMATION: Description of Artificial Sequence: PCCB Coding Sequence - Codon-Optimized

<400> SEQUENCE: 13

```
atggctgcag cactaagggt agcagcagta ggtgcaaggc tatcagtact agcatcaggt     60

ctaagggcag cagtaaggtc actatgttca caagcaacat cagtaaatga aaggatagaa    120

aataagagga ggacagcact actaggtggt gggcagagga ggattgatgc tcagcataag    180

agggggaagc tgacagctag ggagaggatt tctctgctgc tggatcctgg gtcttttgtg    240

gagtctgata tgtttgtgga gcataggtgt gctgattttg ggatggctgc tgataagaat    300

aagtttcctg gggattctgt ggtgacaggg agggggagga ttaatgggag gctggtgtat    360

gtgttttctc aggattttac agtgtttggg gggtctctgt ctggggctca tgctcagaag    420

atttgtaaga ttatggatca ggctattaca gtgggggctc ctgtgattgg gctgaatgat    480
```

```
tctggggggg ctaggattca ggagggggtg gagtctctgg ctgggtatgc tgatattttt    540

ctgaggaatg tgacagcttc tggggtgatt cctcagattt ctctgattat ggggccttgt    600

gctggggggg ctgtgtattc tcctgctctg acagatttta catttatggt gaaggataca    660

tcttatctgt ttattacagg gcctgatgtg gtgaagtctg tgacaaatga ggatgtgaca    720

caggaggagc tgggggggc taagacacat acaacaatgt ctggggtggc tcatagggct    780

tttgagaatg atgtggatgc tctgtgtaat ctgagggatt tttttaatta tctgcctctg    840

tcttctcagg atcctgctcc tgtgagggag tgtcatgatc cttctgatag gctggtgcct    900

gagctggata caattgtgcc tctggagtct acaaaggctt ataatatggt ggatattatt    960

cattctgtgg tggatgagag ggagtttttt gagattatgc ctaattatgc taagaatatt   1020

attgtggggt ttgctaggat gaatgggagg acagtgggga ttgtggggaa tcagcctaag   1080

gtggcttctg ggtgtctgga tattaattct tctgtgaagg gggctaggtt tgtgaggttt   1140

tgtgatgctt ttaatattcc tctgattaca tttgtggatg tgcctgggtt tctgcctggg   1200

acagctcagg agtatggggg gattattagg catggggcta agctgctgta tgcttttgct   1260

gaggctacag tgcctaaggt gacagtgatt acaaggaagg cttatggggg ggcttatgat   1320

gtgatgtctt ctaagcatct gtgtggggat acaaattatg cttggcctac agctgagatt   1380

gctgtgatgg gggctaaggg ggctgtggag attatttta aggggcatga gaatgtggag   1440

gctgctcagg ctgagtatat tgagaagttt gctaatcctt ttcctgctgc tgtgaggggg   1500

tttgtggatg atattattca gccttcttct acaagggcta ggatttgttg tgatctggat   1560

gtgctggctt ctaagaaggt gcagaggcct tggaggaagc atgctaatat tcctctg      1617
```

<210> SEQ ID NO 14
<211> LENGTH: 2217
<212> TYPE: DNA
<213> ORGANISM: Artificial Sequence
<220> FEATURE:
<223> OTHER INFORMATION: Description of Artificial Sequence: AAV8 VP1 Nucleic Acid Sequence

<400> SEQUENCE: 14

```
atggctgccg atggttatct tccagattgg ctcgaggaca acctctctga gggcattcgc     60

gagtggtggg cgctgaaacc tggagccccg aagcccaaag ccaaccagca aaagcaggac    120

gacggccggg gtctggtgct tcctggctac aagtacctcg gacccttcaa cggactcgac    180

aagggggagc ccgtcaacgc ggcggacgca gcggccctcg agcacgacaa ggcctacgac    240

cagcagctgc aggcgggtga caatccgtac ctgcggtata accacgccga cgccgagttt    300

caggagcgtc tgcaagaaga tacgtctttt gggggcaacc tcgggcgagc agtcttccag    360

gccaagaagc gggttctcga acctctcggt ctggttgagg aaggcgctaa gacggctcct    420

ggaaagaaga gaccggtaga gccatcaccc cagcgttctc cagactcctc tacgggcatc    480

ggcaagaaag gccaacagcc cgccagaaaa agactcaatt ttggtcagac tggcgactca    540

gagtcagttc cagaccctca acctctcgga gaacctccag cagcgccctc tggtgtggga    600

cctaatacaa tggctgcagg cggtggcgca ccaatggcag acaataacga aggcgccgac    660

ggagtgggta gttcctcggg aaattggcat tgcgattcca catggctggg cgacagagtc    720

atcaccacca gcacccgaac ctgggccctg cccacctaca acaaccacct ctacaagcaa    780

atctccaacg ggacatcggg aggagccacc aacgacaaca cctacttcgg ctacagcacc    840

ccctgggggt attttgactt taacagattc cactgccact tttcaccacg tgactggcag    900
```

```
cgactcatca acaacaactg ggattccgg cccaagagac tcagcttcaa gctcttcaac    960

atccaggtca aggaggtcac gcagaatgaa ggcaccaaga ccatcgccaa taacctcacc   1020

agcaccatcc aggtgtttac ggactcggag taccagctgc cgtacgttct cggctctgcc   1080

caccagggct gcctgcctcc gttcccggcg gacgtgttca tgattcccca gtacggctac   1140

ctaacactca acaacggtag tcaggccgtg ggacgctcct ccttctactg cctggaatac   1200

tttccttcgc agatgctgag aaccggcaac aacttccagt ttacttacac cttcgaggac   1260

gtgcctttcc acagcagcta cgcccacagc cagagcttgg accggctgat gaatcctctg   1320

attgaccagt acctgtacta cttgtctcgg actcaaacaa caggaggcac ggcaaatacg   1380

cagactctgg gcttcagcca aggtgggcct aatacaatgg ccaatcaggc aaagaactgg   1440

ctgccaggac cctgttaccg ccaacaacgc gtctcaacga caaccgggca aaacaacaat   1500

agcaactttg cctggactgc tgggaccaaa taccatctga atggaagaaa ttcattggct   1560

aatcctggca tcgctatggc aacacacaaa gacgacgagg agcgtttttt tcccagtaac   1620

gggatcctga tttttggcaa acaaaatgct gccagagaca atgcggatta cagcgatgtc   1680

atgctcacca gcgaggaaga aatcaaaacc actaaccctg tggctacaga ggaatacggt   1740

atcgtggcag ataacttgca gcagcaaaac acggctcctc aaattggaac tgtcaacagc   1800

caggggggcct tacccggtat ggtctggcag aaccgggacg tgtacctgca gggtcccatc   1860

tgggccaaga ttcctcacac ggacggcaac ttccacccgt ctccgctgat gggcggcttt   1920

ggcctgaaac atcctccgcc tcagatcctg atcaagaaca cgcctgtacc tgcggatcct   1980

ccgaccacct tcaaccagtc aaagctgaac tctttcatca cgcaatacag caccggacag   2040

gtcagcgtgg aaattgaatg ggagctgcag aaggaaaaca gcaagcgctg gaaccccgag   2100

atccagtaca cctccaacta ctacaaatct acaagtgtgg actttgctgt taatacagaa   2160

ggcgtgtact ctgaaccccg ccccattggc acccgttacc tcacccgtaa tctgtaa      2217
```

<210> SEQ ID NO 15
<211> LENGTH: 738
<212> TYPE: PRT
<213> ORGANISM: Artificial Sequence
<220> FEATURE:
<223> OTHER INFORMATION: Description of Artificial Sequence: AAV8 VP1 Amino Acid Sequence

<400> SEQUENCE: 15

```
Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Gln Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125
```

```
Leu Gly Leu Val Glu Glu Gly Ala Lys Thr Ala Pro Gly Lys Lys Arg
    130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Arg Lys Arg Leu Asn Phe Gly Gln
                165                 170                 175

Thr Gly Asp Ser Glu Ser Val Pro Asp Pro Gln Pro Leu Gly Glu Pro
            180                 185                 190

Pro Ala Ala Pro Ser Gly Val Gly Pro Asn Thr Met Ala Ala Gly Gly
        195                 200                 205

Gly Ala Pro Met Ala Asp Asn Asn Glu Gly Ala Asp Gly Val Gly Ser
    210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Asn Gly Thr Ser Gly Gly Ala Thr Asn Asp
            260                 265                 270

Asn Thr Tyr Phe Gly Tyr Ser Thr Pro Trp Gly Tyr Phe Asp Phe Asn
        275                 280                 285

Arg Phe His Cys His Phe Ser Pro Arg Asp Trp Gln Arg Leu Ile Asn
    290                 295                 300

Asn Asn Trp Gly Phe Arg Pro Lys Arg Leu Ser Phe Lys Leu Phe Asn
305                 310                 315                 320

Ile Gln Val Lys Glu Val Thr Gln Asn Glu Gly Thr Lys Thr Ile Ala
                325                 330                 335

Asn Asn Leu Thr Ser Thr Ile Gln Val Phe Thr Asp Ser Glu Tyr Gln
            340                 345                 350

Leu Pro Tyr Val Leu Gly Ser Ala His Gln Gly Cys Leu Pro Pro Phe
        355                 360                 365

Pro Ala Asp Val Phe Met Ile Pro Gln Tyr Gly Tyr Leu Thr Leu Asn
    370                 375                 380

Asn Gly Ser Gln Ala Val Gly Arg Ser Ser Phe Tyr Cys Leu Glu Tyr
385                 390                 395                 400

Phe Pro Ser Gln Met Leu Arg Thr Gly Asn Asn Phe Gln Phe Thr Tyr
                405                 410                 415

Thr Phe Glu Asp Val Pro Phe His Ser Ser Tyr Ala His Ser Gln Ser
            420                 425                 430

Leu Asp Arg Leu Met Asn Pro Leu Ile Asp Gln Tyr Leu Tyr Tyr Leu
        435                 440                 445

Ser Arg Thr Gln Thr Thr Gly Gly Thr Ala Asn Thr Gln Thr Leu Gly
    450                 455                 460

Phe Ser Gln Gly Gly Pro Asn Thr Met Ala Asn Gln Ala Lys Asn Trp
465                 470                 475                 480

Leu Pro Gly Pro Cys Tyr Arg Gln Gln Arg Val Ser Thr Thr Thr Gly
                485                 490                 495

Gln Asn Asn Asn Ser Asn Phe Ala Trp Thr Ala Gly Thr Lys Tyr His
            500                 505                 510

Leu Asn Gly Arg Asn Ser Leu Ala Asn Pro Gly Ile Ala Met Ala Thr
        515                 520                 525

His Lys Asp Asp Glu Glu Arg Phe Phe Pro Ser Asn Gly Ile Leu Ile
    530                 535                 540

Phe Gly Lys Gln Asn Ala Ala Arg Asp Asn Ala Asp Tyr Ser Asp Val
```

```
545                 550                 555                 560

Met Leu Thr Ser Glu Glu Glu Ile Lys Thr Thr Asn Pro Val Ala Thr
                565                 570                 575

Glu Glu Tyr Gly Ile Val Ala Asp Asn Leu Gln Gln Gln Asn Thr Ala
            580                 585                 590

Pro Gln Ile Gly Thr Val Asn Ser Gln Gly Ala Leu Pro Gly Met Val
        595                 600                 605

Trp Gln Asn Arg Asp Val Tyr Leu Gln Gly Pro Ile Trp Ala Lys Ile
    610                 615                 620

Pro His Thr Asp Gly Asn Phe His Pro Ser Pro Leu Met Gly Gly Phe
625                 630                 635                 640

Gly Leu Lys His Pro Pro Pro Gln Ile Leu Ile Lys Asn Thr Pro Val
                645                 650                 655

Pro Ala Asp Pro Pro Thr Thr Phe Asn Gln Ser Lys Leu Asn Ser Phe
            660                 665                 670

Ile Thr Gln Tyr Ser Thr Gly Gln Val Ser Val Glu Ile Glu Trp Glu
        675                 680                 685

Leu Gln Lys Glu Asn Ser Lys Arg Trp Asn Pro Glu Ile Gln Tyr Thr
    690                 695                 700

Ser Asn Tyr Tyr Lys Ser Thr Ser Val Asp Phe Ala Val Asn Thr Glu
705                 710                 715                 720

Gly Val Tyr Ser Glu Pro Arg Pro Ile Gly Thr Arg Tyr Leu Thr Arg
                725                 730                 735

Asn Leu


<210> SEQ ID NO 16
<211> LENGTH: 2211
<212> TYPE: DNA
<213> ORGANISM: Artificial Sequence
<220> FEATURE:
<223> OTHER INFORMATION: Description of Artificial Sequence: AAV9 VP1
      Nucleic Acid Sequence

<400> SEQUENCE: 16

atggctgccg atggttatct tccagattgg ctcgaggaca accttagtga aggaattcgc      60

gagtggtggg ctttgaaacc tggagcccct caacccaagg caaatcaaca acatcaagac     120

aacgctcgag gtcttgtgct tccgggttac aaataccttg gacccggcaa cggactcgac     180

aagggggagc cggtcaacgc agcagacgcg gcggccctcg agcacgacaa ggcctacgac     240

cagcagctca aggccggaga caacccgtac ctcaagtaca accacgccga cgccgagttc     300

caggagcggc tcaaagaaga tacgtctttt gggggcaacc tcgggcgagc agtcttccag     360

gccaaaaaga ggcttcttga acctcttggt ctggttgagg aagcggctaa gacggctcct     420

ggaaagaaga ggcctgtaga gcagtctcct caggaaccgg actcctccgc gggtattggc     480

aaatcgggtg cacagcccgc taaaaagaga ctcaatttcg gtcagactgg cgacacagag     540

tcagtcccag accctcaacc aatcggagaa cctcccgcag ccccctcagg tgtgggatct     600

cttacaatgg cttcaggtgg tggcgcacca gtggcagaca ataacgaagg tgccgatgga     660

gtgggtagtt cctcgggaaa ttggcattgc gattcccaat ggctgggga cagagtcatc     720

accaccagca cccgaacctg ggccctgccc acctacaaca atcacctcta caagcaaatc     780

tccaacagca catctggagg atcttcaaat gacaacgcct acttcggcta cagcaccccc     840

tgggggtatt ttgacttcaa cagattccac tgccacttct caccacgtga ctggcagcga     900

ctcatcaaca acaactgggg attccggcct aagcgactca acttcaagct cttcaacatt     960
```

```
caggtcaaag aggttacgga caacaatgga gtcaagacca tcgccaataa ccttaccagc   1020

acggtccagg tcttcacgga ctcagactat cagctcccgt acgtgctcgg gtcggctcac   1080

gagggctgcc tcccgccgtt cccagcggac gttttcatga ttcctcagta cgggtatctg   1140

acgcttaatg atggaagcca ggccgtgggt cgttcgtcct tttactgcct ggaatatttc   1200

ccgtcgcaaa tgctaagaac gggtaacaac ttccagttca gctacgagtt tgagaacgta   1260

cctttccata gcagctacgc tcacagccaa agcctggacc gactaatgaa tccactcatc   1320

gaccaatact tgtactatct ctcaaagact attaacggtt ctggacagaa tcaacaaacg   1380

ctaaaattca gtgtggccgg acccagcaac atggctgtcc agggaagaaa ctacatacct   1440

ggacccagct accgacaaca acgtgtctca accactgtga ctcaaaacaa caacagcgaa   1500

tttgcttggc ctggagcttc ttcttgggct ctcaatggac gtaatagctt gatgaatcct   1560

ggacctgcta tggccagcca caaagaagga gaggaccgtt tctttccttt gtctggatct   1620

ttaatttttg gcaaacaagg aactggaaga gacaacgtgg atgcggacaa agtcatgata   1680

accaacgaag aagaaattaa aactactaac ccggtagcaa cggagtccta tggacaagtg   1740

gccacaaacc accagagtgc ccaagcacag gcgcagaccg gctgggttca aaaccaagga   1800

atacttccgg gtatggtttg gcaggacaga gatgtgtacc tgcaaggacc catttgggcc   1860

aaaattcctc acacggacgg caactttcac ccttctccgc tgatgggagg gtttggaatg   1920

aagcacccgc ctcctcagat cctcatcaaa aacacacctg tacctgcgga tcctccaacg   1980

gccttcaaca aggacaagct gaactctttc atcacccagt attctactgg ccaagtcagc   2040

gtggagatcg agtgggagct gcagaaggaa aacagcaagc gctggaaccc ggagatccag   2100

tacacttcca actattacaa gtctaataat gttgaatttg ctgttaatac tgaaggtgta   2160

tatagtgaac cccgccccat tggcaccaga tacctgactc gtaatctgta a            2211
```

<210> SEQ ID NO 17
<211> LENGTH: 736
<212> TYPE: PRT
<213> ORGANISM: Artificial Sequence
<220> FEATURE:
<223> OTHER INFORMATION: Description of Artificial Sequence: AAV9 VP1 Amino Acid Sequence

<400> SEQUENCE: 17

```
Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Ala Lys Thr Ala Pro Gly Lys Lys Arg
```

-continued

```
    130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
        195                 200                 205

Ala Pro Val Ala Asp Asn Asn Glu Gly Ala Asp Gly Val Gly Ser Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
            260                 265                 270

Ala Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
    290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
            340                 345                 350

Pro Tyr Val Leu Gly Ser Ala His Glu Gly Cys Leu Pro Pro Phe Pro
        355                 360                 365

Ala Asp Val Phe Met Ile Pro Gln Tyr Gly Tyr Leu Thr Leu Asn Asp
    370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                405                 410                 415

Phe Glu Asn Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ser
        435                 440                 445

Lys Thr Ile Asn Gly Ser Gly Gln Asn Gln Gln Thr Leu Lys Phe Ser
    450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
                485                 490                 495

Asn Asn Ser Glu Phe Ala Trp Pro Gly Ala Ser Ser Trp Ala Leu Asn
            500                 505                 510

Gly Arg Asn Ser Leu Met Asn Pro Gly Pro Ala Met Ala Ser His Lys
        515                 520                 525

Glu Gly Glu Asp Arg Phe Phe Pro Leu Ser Gly Ser Leu Ile Phe Gly
    530                 535                 540

Lys Gln Gly Thr Gly Arg Asp Asn Val Asp Ala Asp Lys Val Met Ile
545                 550                 555                 560
```

```
Thr Asn Glu Glu Glu Ile Lys Thr Thr Asn Pro Val Ala Thr Glu Ser
                565                 570                 575

Tyr Gly Gln Val Ala Thr Asn His Gln Ser Ala Gln Ala Gln Ala Gln
            580                 585                 590

Thr Gly Trp Val Gln Asn Gln Gly Ile Leu Pro Gly Met Val Trp Gln
        595                 600                 605

Asp Arg Asp Val Tyr Leu Gln Gly Pro Ile Trp Ala Lys Ile Pro His
    610                 615                 620

Thr Asp Gly Asn Phe His Pro Ser Pro Leu Met Gly Gly Phe Gly Met
625                 630                 635                 640

Lys His Pro Pro Pro Gln Ile Leu Ile Lys Asn Thr Pro Val Pro Ala
                645                 650                 655

Asp Pro Pro Thr Ala Phe Asn Lys Asp Lys Leu Asn Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Ile Gln Tyr Thr Ser Asn
    690                 695                 700

Tyr Tyr Lys Ser Asn Asn Val Glu Phe Ala Val Asn Thr Glu Gly Val
705                 710                 715                 720

Tyr Ser Glu Pro Arg Pro Ile Gly Thr Arg Tyr Leu Thr Arg Asn Leu
                725                 730                 735


<210> SEQ ID NO 18
<211> LENGTH: 145
<212> TYPE: DNA
<213> ORGANISM: Artificial Sequence
<220> FEATURE:
<223> OTHER INFORMATION: Description of Artificial Sequence: AAV2 ITR

<400> SEQUENCE: 18

ttggccactc cctctctgcg cgctcgctcg ctcactgagg ccgggcgacc aaaggtcgcc      60

cgacgcccgg gctttgcccg ggcggcctca gtgagcgagc gagcgcgcag agagggagtg     120

gccaactcca tcactagggg ttcct                                           145


<210> SEQ ID NO 19
<211> LENGTH: 728
<212> TYPE: PRT
<213> ORGANISM: Homo sapiens
<220> FEATURE:
<221> NAME/KEY: MISC_FEATURE
<222> LOCATION: (1)..(728)
<223> OTHER INFORMATION: PCCA Amino Acid Sequence

<400> SEQUENCE: 19

Met Ala Gly Phe Trp Val Gly Thr Ala Pro Leu Val Ala Ala Gly Arg
1               5                   10                  15

Arg Gly Arg Trp Pro Pro Gln Gln Leu Met Leu Ser Ala Ala Leu Arg
            20                  25                  30

Thr Leu Lys His Val Leu Tyr Tyr Ser Arg Gln Cys Leu Met Val Ser
        35                  40                  45

Arg Asn Leu Gly Ser Val Gly Tyr Asp Pro Asn Glu Lys Thr Phe Asp
    50                  55                  60

Lys Ile Leu Val Ala Asn Arg Gly Glu Ile Ala Cys Arg Val Ile Arg
65                  70                  75                  80

Thr Cys Lys Lys Met Gly Ile Lys Thr Val Ala Ile His Ser Asp Val
                85                  90                  95
```

-continued

```
Asp Ala Ser Ser Val His Val Lys Met Ala Asp Glu Ala Val Cys Val
            100                 105                 110

Gly Pro Ala Pro Thr Ser Lys Ser Tyr Leu Asn Met Asp Ala Ile Met
        115                 120                 125

Glu Ala Ile Lys Lys Thr Arg Ala Gln Ala Val His Pro Gly Tyr Gly
    130                 135                 140

Phe Leu Ser Glu Asn Lys Glu Phe Ala Arg Cys Leu Ala Ala Glu Asp
145                 150                 155                 160

Val Val Phe Ile Gly Pro Asp Thr His Ala Ile Gln Ala Met Gly Asp
                165                 170                 175

Lys Ile Glu Ser Lys Leu Leu Ala Lys Lys Ala Glu Val Asn Thr Ile
            180                 185                 190

Pro Gly Phe Asp Gly Val Val Lys Asp Ala Glu Glu Ala Val Arg Ile
        195                 200                 205

Ala Arg Glu Ile Gly Tyr Pro Val Met Ile Lys Ala Ser Ala Gly Gly
    210                 215                 220

Gly Gly Lys Gly Met Arg Ile Ala Trp Asp Asp Glu Glu Thr Arg Asp
225                 230                 235                 240

Gly Phe Arg Leu Ser Ser Gln Glu Ala Ala Ser Ser Phe Gly Asp Asp
                245                 250                 255

Arg Leu Leu Ile Glu Lys Phe Ile Asp Asn Pro Arg His Ile Glu Ile
            260                 265                 270

Gln Val Leu Gly Asp Lys His Gly Asn Ala Leu Trp Leu Asn Glu Arg
        275                 280                 285

Glu Cys Ser Ile Gln Arg Arg Asn Gln Lys Val Val Glu Glu Ala Pro
    290                 295                 300

Ser Ile Phe Leu Asp Ala Glu Thr Arg Arg Ala Met Gly Glu Gln Ala
305                 310                 315                 320

Val Ala Leu Ala Arg Ala Val Lys Tyr Ser Ser Ala Gly Thr Val Glu
                325                 330                 335

Phe Leu Val Asp Ser Lys Lys Asn Phe Tyr Phe Leu Glu Met Asn Thr
            340                 345                 350

Arg Leu Gln Val Glu His Pro Val Thr Glu Cys Ile Thr Gly Leu Asp
        355                 360                 365

Leu Val Gln Glu Met Ile Arg Val Ala Lys Gly Tyr Pro Leu Arg His
    370                 375                 380

Lys Gln Ala Asp Ile Arg Ile Asn Gly Trp Ala Val Glu Cys Arg Val
385                 390                 395                 400

Tyr Ala Glu Asp Pro Tyr Lys Ser Phe Gly Leu Pro Ser Ile Gly Arg
                405                 410                 415

Leu Ser Gln Tyr Gln Glu Pro Leu His Leu Pro Gly Val Arg Val Asp
            420                 425                 430

Ser Gly Ile Gln Pro Gly Ser Asp Ile Ser Ile Tyr Tyr Asp Pro Met
        435                 440                 445

Ile Ser Lys Leu Ile Thr Tyr Gly Ser Asp Arg Thr Glu Ala Leu Lys
    450                 455                 460

Arg Met Ala Asp Ala Leu Asp Asn Tyr Val Ile Arg Gly Val Thr His
465                 470                 475                 480

Asn Ile Ala Leu Leu Arg Glu Val Ile Ile Asn Ser Arg Phe Val Lys
                485                 490                 495

Gly Asp Ile Ser Thr Lys Phe Leu Ser Asp Val Tyr Pro Asp Gly Phe
            500                 505                 510
```

```
Lys Gly His Met Leu Thr Lys Ser Glu Lys Asn Gln Leu Leu Ala Ile
        515                 520                 525

Ala Ser Ser Leu Phe Val Ala Phe Gln Leu Arg Ala Gln His Phe Gln
    530                 535                 540

Glu Asn Ser Arg Met Pro Val Ile Lys Pro Asp Ile Ala Asn Trp Glu
545                 550                 555                 560

Leu Ser Val Lys Leu His Asp Lys Val His Thr Val Val Ala Ser Asn
                565                 570                 575

Asn Gly Ser Val Phe Ser Val Glu Val Asp Gly Ser Lys Leu Asn Val
            580                 585                 590

Thr Ser Thr Trp Asn Leu Ala Ser Pro Leu Leu Ser Val Ser Val Asp
        595                 600                 605

Gly Thr Gln Arg Thr Val Gln Cys Leu Ser Arg Glu Ala Gly Gly Asn
    610                 615                 620

Met Ser Ile Gln Phe Leu Gly Thr Val Tyr Lys Val Asn Ile Leu Thr
625                 630                 635                 640

Arg Leu Ala Ala Glu Leu Asn Lys Phe Met Leu Glu Lys Val Thr Glu
                645                 650                 655

Asp Thr Ser Ser Val Leu Arg Ser Pro Met Pro Gly Val Val Val Ala
            660                 665                 670

Val Ser Val Lys Pro Gly Asp Ala Val Ala Glu Gly Gln Glu Ile Cys
        675                 680                 685

Val Ile Glu Ala Met Lys Met Gln Asn Ser Met Thr Ala Gly Lys Thr
    690                 695                 700

Gly Thr Val Lys Ser Val His Cys Gln Ala Gly Asp Thr Val Gly Glu
705                 710                 715                 720

Gly Asp Leu Leu Val Glu Leu Glu
                725


<210> SEQ ID NO 20
<211> LENGTH: 539
<212> TYPE: PRT
<213> ORGANISM: Homo sapiens
<220> FEATURE:
<221> NAME/KEY: MISC_FEATURE
<222> LOCATION: (1)..(539)
<223> OTHER INFORMATION: PCCB Amino Acid Sequence

<400> SEQUENCE: 20

Met Ala Ala Ala Leu Arg Val Ala Ala Val Gly Ala Arg Leu Ser Val
1               5                   10                  15

Leu Ala Ser Gly Leu Arg Ala Ala Val Arg Ser Leu Cys Ser Gln Ala
            20                  25                  30

Thr Ser Val Asn Glu Arg Ile Glu Asn Lys Arg Arg Thr Ala Leu Leu
        35                  40                  45

Gly Gly Gly Gln Arg Arg Ile Asp Ala Gln His Lys Arg Gly Lys Leu
    50                  55                  60

Thr Ala Arg Glu Arg Ile Ser Leu Leu Leu Asp Pro Gly Ser Phe Val
65                  70                  75                  80

Glu Ser Asp Met Phe Val Glu His Arg Cys Ala Asp Phe Gly Met Ala
                85                  90                  95

Ala Asp Lys Asn Lys Phe Pro Gly Asp Ser Val Val Thr Gly Arg Gly
            100                 105                 110

Arg Ile Asn Gly Arg Leu Val Tyr Val Phe Ser Gln Asp Phe Thr Val
        115                 120                 125

Phe Gly Gly Ser Leu Ser Gly Ala His Ala Gln Lys Ile Cys Lys Ile
```

```
    130                 135                 140

Met Asp Gln Ala Ile Thr Val Gly Ala Pro Val Ile Gly Leu Asn Asp
145                 150                 155                 160

Ser Gly Gly Ala Arg Ile Gln Glu Gly Val Glu Ser Leu Ala Gly Tyr
                165                 170                 175

Ala Asp Ile Phe Leu Arg Asn Val Thr Ala Ser Gly Val Ile Pro Gln
            180                 185                 190

Ile Ser Leu Ile Met Gly Pro Cys Ala Gly Gly Ala Val Tyr Ser Pro
        195                 200                 205

Ala Leu Thr Asp Phe Thr Phe Met Val Lys Asp Thr Ser Tyr Leu Phe
    210                 215                 220

Ile Thr Gly Pro Asp Val Val Lys Ser Val Thr Asn Glu Asp Val Thr
225                 230                 235                 240

Gln Glu Glu Leu Gly Gly Ala Lys Thr His Thr Thr Met Ser Gly Val
                245                 250                 255

Ala His Arg Ala Phe Glu Asn Asp Val Asp Ala Leu Cys Asn Leu Arg
            260                 265                 270

Asp Phe Phe Asn Tyr Leu Pro Leu Ser Ser Gln Asp Pro Ala Pro Val
        275                 280                 285

Arg Glu Cys His Asp Pro Ser Asp Arg Leu Val Pro Glu Leu Asp Thr
    290                 295                 300

Ile Val Pro Leu Glu Ser Thr Lys Ala Tyr Asn Met Val Asp Ile Ile
305                 310                 315                 320

His Ser Val Val Asp Glu Arg Glu Phe Phe Glu Ile Met Pro Asn Tyr
                325                 330                 335

Ala Lys Asn Ile Ile Val Gly Phe Ala Arg Met Asn Gly Arg Thr Val
            340                 345                 350

Gly Ile Val Gly Asn Gln Pro Lys Val Ala Ser Gly Cys Leu Asp Ile
        355                 360                 365

Asn Ser Ser Val Lys Gly Ala Arg Phe Val Arg Phe Cys Asp Ala Phe
    370                 375                 380

Asn Ile Pro Leu Ile Thr Phe Val Asp Val Pro Gly Phe Leu Pro Gly
385                 390                 395                 400

Thr Ala Gln Glu Tyr Gly Gly Ile Ile Arg His Gly Ala Lys Leu Leu
                405                 410                 415

Tyr Ala Phe Ala Glu Ala Thr Val Pro Lys Val Thr Val Ile Thr Arg
            420                 425                 430

Lys Ala Tyr Gly Gly Ala Tyr Asp Val Met Ser Ser Lys His Leu Cys
        435                 440                 445

Gly Asp Thr Asn Tyr Ala Trp Pro Thr Ala Glu Ile Ala Val Met Gly
    450                 455                 460

Ala Lys Gly Ala Val Glu Ile Ile Phe Lys Gly His Glu Asn Val Glu
465                 470                 475                 480

Ala Ala Gln Ala Glu Tyr Ile Glu Lys Phe Ala Asn Pro Phe Pro Ala
                485                 490                 495

Ala Val Arg Gly Phe Val Asp Asp Ile Ile Gln Pro Ser Ser Thr Arg
            500                 505                 510

Ala Arg Ile Cys Cys Asp Leu Asp Val Leu Ala Ser Lys Lys Val Gln
        515                 520                 525

Arg Pro Trp Arg Lys His Ala Asn Ile Pro Leu
    530                 535

<210> SEQ ID NO 21
```

<211> LENGTH: 276
<212> TYPE: DNA
<213> ORGANISM: Artificial Sequence
<220> FEATURE:
<223> OTHER INFORMATION: Description of Artificial Sequence: CBA Promoter

<400> SEQUENCE: 21

```
tcgaggtgag ccccacgttc tgcttcactc tccccatctc ccccccctcc ccacccccaa     60

ttttgtattt atttattttt taattatttt atgcagcgat gggggcgggg gggggggggg    120

cgcgcgccag gcggggcggg gcggggcgag gggcggggcg gggcgaggcg gagaggtgcg    180

gcggcagcca atcagagcgg cgcgctccga aagtttcctt ttatggcgag gcggcggcgg    240

cggcggccct ataaaaagcg aagcgcgcgg cgggcg                              276
```

<210> SEQ ID NO 22
<211> LENGTH: 304
<212> TYPE: DNA
<213> ORGANISM: Artificial Sequence
<220> FEATURE:
<223> OTHER INFORMATION: Description of Artificial Sequence: CMV Enhancer

<400> SEQUENCE: 22

```
cgttacataa cttacggtaa atggcccgcc tggctgaccg cccaacgacc cccgcccatt     60

gacgtcaata atgacgtatg ttcccatagt aacgccaata gggactttcc attgacgtca    120

atgggtggac tatttacggt aaactgccca cttggcagta catcaagtgt atcatatgcc    180

aagtacgccc cctattgacg tcaatgacgg taaatggccc gcctggcatt atgcccagta    240

catgacctta tgggactttc ctacttggca gtacatctac gtattagtca tcgctattac    300

catg                                                                 304
```

<210> SEQ ID NO 23
<211> LENGTH: 197
<212> TYPE: DNA
<213> ORGANISM: Artificial Sequence
<220> FEATURE:
<223> OTHER INFORMATION: Description of Artificial Sequence: SV40 Late polyadenylation signal sequence

<400> SEQUENCE: 23

```
atccagacat gataagatac attgatgagt ttggacaaac cacaactaga atgcagtgaa     60

aaaaatgctt tatttgtgaa atttgtgatg ctattgcttt atttgtaacc attataagct    120

gcaataaaca agttaacaac aacaattgca ttcattttat gtttcaggtt cagggggagg    180

tgtgggaggt tttttag                                                   197
```

<210> SEQ ID NO 24
<211> LENGTH: 6
<212> TYPE: DNA
<213> ORGANISM: Artificial Sequence
<220> FEATURE:
<223> OTHER INFORMATION: Description of Artificial Sequence: Consensus Kozak Sequence

<400> SEQUENCE: 24

```
gccgcc                                                                 6
```

<210> SEQ ID NO 25
<211> LENGTH: 728
<212> TYPE: PRT
<213> ORGANISM: Homo sapiens

```
<220> FEATURE:
<221> NAME/KEY: MISC_FEATURE
<222> LOCATION: (1)..(728)
<223> OTHER INFORMATION: UniProtKB-Swiss-Prot Accession No. P05165-1
      Amino Acid Sequence

<400> SEQUENCE: 25

Met Ala Gly Phe Trp Val Gly Thr Ala Pro Leu Val Ala Ala Gly Arg
1               5                   10                  15

Arg Gly Arg Trp Pro Pro Gln Gln Leu Met Leu Ser Ala Ala Leu Arg
            20                  25                  30

Thr Leu Lys His Val Leu Tyr Tyr Ser Arg Gln Cys Leu Met Val Ser
        35                  40                  45

Arg Asn Leu Gly Ser Val Gly Tyr Asp Pro Asn Glu Lys Thr Phe Asp
    50                  55                  60

Lys Ile Leu Val Ala Asn Arg Gly Glu Ile Ala Cys Arg Val Ile Arg
65                  70                  75                  80

Thr Cys Lys Lys Met Gly Ile Lys Thr Val Ala Ile His Ser Asp Val
                85                  90                  95

Asp Ala Ser Ser Val His Val Lys Met Ala Asp Glu Ala Val Cys Val
            100                 105                 110

Gly Pro Ala Pro Thr Ser Lys Ser Tyr Leu Asn Met Asp Ala Ile Met
        115                 120                 125

Glu Ala Ile Lys Lys Thr Arg Ala Gln Ala Val His Pro Gly Tyr Gly
    130                 135                 140

Phe Leu Ser Glu Asn Lys Glu Phe Ala Arg Cys Leu Ala Ala Glu Asp
145                 150                 155                 160

Val Val Phe Ile Gly Pro Asp Thr His Ala Ile Gln Ala Met Gly Asp
                165                 170                 175

Lys Ile Glu Ser Lys Leu Leu Ala Lys Lys Ala Glu Val Asn Thr Ile
            180                 185                 190

Pro Gly Phe Asp Gly Val Val Lys Asp Ala Glu Glu Ala Val Arg Ile
        195                 200                 205

Ala Arg Glu Ile Gly Tyr Pro Val Met Ile Lys Ala Ser Ala Gly Gly
    210                 215                 220

Gly Gly Lys Gly Met Arg Ile Ala Trp Asp Asp Glu Glu Thr Arg Asp
225                 230                 235                 240

Gly Phe Arg Leu Ser Ser Gln Glu Ala Ala Ser Ser Phe Gly Asp Asp
                245                 250                 255

Arg Leu Leu Ile Glu Lys Phe Ile Asp Asn Pro Arg His Ile Glu Ile
            260                 265                 270

Gln Val Leu Gly Asp Lys His Gly Asn Ala Leu Trp Leu Asn Glu Arg
        275                 280                 285

Glu Cys Ser Ile Gln Arg Arg Asn Gln Lys Val Val Glu Glu Ala Pro
    290                 295                 300

Ser Ile Phe Leu Asp Ala Glu Thr Arg Arg Ala Met Gly Glu Gln Ala
305                 310                 315                 320

Val Ala Leu Ala Arg Ala Val Lys Tyr Ser Ser Ala Gly Thr Val Glu
                325                 330                 335

Phe Leu Val Asp Ser Lys Lys Asn Phe Tyr Phe Leu Glu Met Asn Thr
            340                 345                 350

Arg Leu Gln Val Glu His Pro Val Thr Glu Cys Ile Thr Gly Leu Asp
        355                 360                 365

Leu Val Gln Glu Met Ile Arg Val Ala Lys Gly Tyr Pro Leu Arg His
    370                 375                 380
```

```
Lys Gln Ala Asp Ile Arg Ile Asn Gly Trp Ala Val Glu Cys Arg Val
385                 390                 395                 400

Tyr Ala Glu Asp Pro Tyr Lys Ser Phe Gly Leu Pro Ser Ile Gly Arg
                405                 410                 415

Leu Ser Gln Tyr Gln Glu Pro Leu His Leu Pro Gly Val Arg Val Asp
            420                 425                 430

Ser Gly Ile Gln Pro Gly Ser Asp Ile Ser Ile Tyr Tyr Asp Pro Met
        435                 440                 445

Ile Ser Lys Leu Ile Thr Tyr Gly Ser Asp Arg Thr Glu Ala Leu Lys
    450                 455                 460

Arg Met Ala Asp Ala Leu Asp Asn Tyr Val Ile Arg Gly Val Thr His
465                 470                 475                 480

Asn Ile Ala Leu Leu Arg Glu Val Ile Ile Asn Ser Arg Phe Val Lys
                485                 490                 495

Gly Asp Ile Ser Thr Lys Phe Leu Ser Asp Val Tyr Pro Asp Gly Phe
            500                 505                 510

Lys Gly His Met Leu Thr Lys Ser Glu Lys Asn Gln Leu Leu Ala Ile
        515                 520                 525

Ala Ser Ser Leu Phe Val Ala Phe Gln Leu Arg Ala Gln His Phe Gln
    530                 535                 540

Glu Asn Ser Arg Met Pro Val Ile Lys Pro Asp Ile Ala Asn Trp Glu
545                 550                 555                 560

Leu Ser Val Lys Leu His Asp Lys Val His Thr Val Val Ala Ser Asn
                565                 570                 575

Asn Gly Ser Val Phe Ser Val Glu Val Asp Gly Ser Lys Leu Asn Val
            580                 585                 590

Thr Ser Thr Trp Asn Leu Ala Ser Pro Leu Leu Ser Val Ser Val Asp
        595                 600                 605

Gly Thr Gln Arg Thr Val Gln Cys Leu Ser Arg Glu Ala Gly Gly Asn
    610                 615                 620

Met Ser Ile Gln Phe Leu Gly Thr Val Tyr Lys Val Asn Ile Leu Thr
625                 630                 635                 640

Arg Leu Ala Ala Glu Leu Asn Lys Phe Met Leu Glu Lys Val Thr Glu
                645                 650                 655

Asp Thr Ser Ser Val Leu Arg Ser Pro Met Pro Gly Val Val Val Ala
            660                 665                 670

Val Ser Val Lys Pro Gly Asp Ala Val Ala Glu Gly Gln Glu Ile Cys
        675                 680                 685

Val Ile Glu Ala Met Lys Met Gln Asn Ser Met Thr Ala Gly Lys Thr
    690                 695                 700

Gly Thr Val Lys Ser Val His Cys Gln Ala Gly Asp Thr Val Gly Glu
705                 710                 715                 720

Gly Asp Leu Leu Val Glu Leu Glu
                725
```

<210> SEQ ID NO 26
<211> LENGTH: 702
<212> TYPE: PRT
<213> ORGANISM: Homo sapiens
<220> FEATURE:
<221> NAME/KEY: MISC_FEATURE
<222> LOCATION: (1)..(702)
<223> OTHER INFORMATION: UniProtKB-Swiss-Prot Accession No. P05165-2
Amino Acid Sequence

<400> SEQUENCE: 26

```
Met Ala Gly Phe Trp Val Gly Thr Ala Pro Leu Val Ala Ala Gly Arg
1               5                   10                  15

Arg Gly Arg Trp Pro Pro Gln Gln Leu Met Leu Ser Ala Ala Leu Arg
            20                  25                  30

Thr Leu Lys Thr Phe Asp Lys Ile Leu Val Ala Asn Arg Gly Glu Ile
        35                  40                  45

Ala Cys Arg Val Ile Arg Thr Cys Lys Lys Met Gly Ile Lys Thr Val
    50                  55                  60

Ala Ile His Ser Asp Val Asp Ala Ser Ser Val His Val Lys Met Ala
65                  70                  75                  80

Asp Glu Ala Val Cys Val Gly Pro Ala Pro Thr Ser Lys Ser Tyr Leu
                85                  90                  95

Asn Met Asp Ala Ile Met Glu Ala Ile Lys Lys Thr Arg Ala Gln Ala
            100                 105                 110

Val His Pro Gly Tyr Gly Phe Leu Ser Glu Asn Lys Glu Phe Ala Arg
        115                 120                 125

Cys Leu Ala Ala Glu Asp Val Val Phe Ile Gly Pro Asp Thr His Ala
    130                 135                 140

Ile Gln Ala Met Gly Asp Lys Ile Glu Ser Lys Leu Leu Ala Lys Lys
145                 150                 155                 160

Ala Glu Val Asn Thr Ile Pro Gly Phe Asp Gly Val Val Lys Asp Ala
                165                 170                 175

Glu Glu Ala Val Arg Ile Ala Arg Glu Ile Gly Tyr Pro Val Met Ile
            180                 185                 190

Lys Ala Ser Ala Gly Gly Gly Gly Lys Gly Met Arg Ile Ala Trp Asp
        195                 200                 205

Asp Glu Glu Thr Arg Asp Gly Phe Arg Leu Ser Ser Gln Glu Ala Ala
    210                 215                 220

Ser Ser Phe Gly Asp Asp Arg Leu Leu Ile Glu Lys Phe Ile Asp Asn
225                 230                 235                 240

Pro Arg His Ile Glu Ile Gln Val Leu Gly Asp Lys His Gly Asn Ala
                245                 250                 255

Leu Trp Leu Asn Glu Arg Glu Cys Ser Ile Gln Arg Arg Asn Gln Lys
            260                 265                 270

Val Val Glu Glu Ala Pro Ser Ile Phe Leu Asp Ala Glu Thr Arg Arg
        275                 280                 285

Ala Met Gly Glu Gln Ala Val Ala Leu Ala Arg Ala Val Lys Tyr Ser
    290                 295                 300

Ser Ala Gly Thr Val Glu Phe Leu Val Asp Ser Lys Lys Asn Phe Tyr
305                 310                 315                 320

Phe Leu Glu Met Asn Thr Arg Leu Gln Val Glu His Pro Val Thr Glu
                325                 330                 335

Cys Ile Thr Gly Leu Asp Leu Val Gln Glu Met Ile Arg Val Ala Lys
            340                 345                 350

Gly Tyr Pro Leu Arg His Lys Gln Ala Asp Ile Arg Ile Asn Gly Trp
        355                 360                 365

Ala Val Glu Cys Arg Val Tyr Ala Glu Asp Pro Tyr Lys Ser Phe Gly
    370                 375                 380

Leu Pro Ser Ile Gly Arg Leu Ser Gln Tyr Gln Glu Pro Leu His Leu
385                 390                 395                 400

Pro Gly Val Arg Val Asp Ser Gly Ile Gln Pro Gly Ser Asp Ile Ser
                405                 410                 415
```

```
Ile Tyr Tyr Asp Pro Met Ile Ser Lys Leu Ile Thr Tyr Gly Ser Asp
            420                 425                 430

Arg Thr Glu Ala Leu Lys Arg Met Ala Asp Ala Leu Asp Asn Tyr Val
        435                 440                 445

Ile Arg Gly Val Thr His Asn Ile Ala Leu Leu Arg Glu Val Ile Ile
    450                 455                 460

Asn Ser Arg Phe Val Lys Gly Asp Ile Ser Thr Lys Phe Leu Ser Asp
465                 470                 475                 480

Val Tyr Pro Asp Gly Phe Lys Gly His Met Leu Thr Lys Ser Glu Lys
                485                 490                 495

Asn Gln Leu Leu Ala Ile Ala Ser Ser Leu Phe Val Ala Phe Gln Leu
            500                 505                 510

Arg Ala Gln His Phe Gln Glu Asn Ser Arg Met Pro Val Ile Lys Pro
        515                 520                 525

Asp Ile Ala Asn Trp Glu Leu Ser Val Lys Leu His Asp Lys Val His
    530                 535                 540

Thr Val Val Ala Ser Asn Asn Gly Ser Val Phe Ser Val Glu Val Asp
545                 550                 555                 560

Gly Ser Lys Leu Asn Val Thr Ser Thr Trp Asn Leu Ala Ser Pro Leu
                565                 570                 575

Leu Ser Val Ser Val Asp Gly Thr Gln Arg Thr Val Gln Cys Leu Ser
            580                 585                 590

Arg Glu Ala Gly Gly Asn Met Ser Ile Gln Phe Leu Gly Thr Val Tyr
        595                 600                 605

Lys Val Asn Ile Leu Thr Arg Leu Ala Ala Glu Leu Asn Lys Phe Met
    610                 615                 620

Leu Glu Lys Val Thr Glu Asp Thr Ser Ser Val Leu Arg Ser Pro Met
625                 630                 635                 640

Pro Gly Val Val Val Ala Val Ser Val Lys Pro Gly Asp Ala Val Ala
                645                 650                 655

Glu Gly Gln Glu Ile Cys Val Ile Glu Ala Met Lys Met Gln Asn Ser
            660                 665                 670

Met Thr Ala Gly Lys Thr Gly Thr Val Lys Ser Val His Cys Gln Ala
        675                 680                 685

Gly Asp Thr Val Gly Glu Gly Asp Leu Leu Val Glu Leu Glu
    690                 695                 700


<210> SEQ ID NO 27
<211> LENGTH: 681
<212> TYPE: PRT
<213> ORGANISM: Homo sapiens
<220> FEATURE:
<221> NAME/KEY: MISC_FEATURE
<222> LOCATION: (1)..(681)
<223> OTHER INFORMATION: UniProtKB-Swiss-Prot Accession No. P05165-3
      Amino Acid Sequence

<400> SEQUENCE: 27

Met Ala Gly Phe Trp Val Gly Thr Ala Pro Leu Val Ala Ala Gly Arg
1               5                   10                  15

Arg Gly Arg Trp Pro Pro Gln Gln Leu Met Leu Ser Ala Ala Leu Arg
            20                  25                  30

Thr Leu Lys His Val Leu Tyr Tyr Ser Arg Gln Cys Leu Met Val Ser
        35                  40                  45

Arg Asn Leu Gly Ser Val Gly Tyr Asp Pro Asn Glu Lys Thr Phe Asp
    50                  55                  60
```

```
Lys Ile Leu Val Ala Asn Arg Gly Glu Ile Ala Cys Arg Val Ile Arg
65                  70                  75                  80

Thr Cys Lys Lys Met Gly Ile Lys Thr Val Ala Ile His Ser Asp Val
                85                  90                  95

Asp Ala Ser Ser Val His Val Lys Met Ala Asp Glu Ala Val Cys Val
            100                 105                 110

Gly Pro Ala Pro Thr Ser Lys Ser Tyr Leu Asn Met Asp Ala Ile Met
        115                 120                 125

Glu Ala Ile Lys Lys Thr Arg Ala Gln Ala Val His Pro Gly Tyr Gly
    130                 135                 140

Phe Leu Ser Glu Asn Lys Glu Phe Ala Arg Cys Leu Ala Ala Glu Asp
145                 150                 155                 160

Val Val Phe Ile Gly Pro Asp Thr His Ala Ile Gln Ala Met Gly Asp
                165                 170                 175

Lys Ile Glu Ser Lys Leu Leu Ala Lys Lys Ala Glu Val Asn Thr Ile
            180                 185                 190

Pro Gly Phe Asp Gly Val Val Lys Asp Ala Glu Glu Ala Val Arg Ile
        195                 200                 205

Ala Arg Glu Ile Gly Tyr Pro Val Met Ile Lys Ala Ser Ala Gly Gly
    210                 215                 220

Gly Gly Lys Gly Met Arg Ile Ala Trp Asp Asp Glu Glu Thr Arg Asp
225                 230                 235                 240

Gly Phe Arg Leu Ser Ser Gln Glu Ala Ala Ser Ser Phe Gly Asp Asp
                245                 250                 255

Arg Leu Leu Ile Glu Lys Phe Ile Asp Asn Pro Arg His Ile Glu Ile
            260                 265                 270

Gln Val Leu Gly Asp Lys His Gly Asn Ala Leu Trp Leu Asn Glu Arg
        275                 280                 285

Glu Cys Ser Ile Gln Arg Arg Asn Gln Lys Val Val Glu Glu Ala Pro
    290                 295                 300

Ser Ile Phe Leu Asp Ala Glu Thr Arg Arg Ala Met Gly Glu Gln Ala
305                 310                 315                 320

Val Ala Leu Ala Arg Ala Val Lys Tyr Ser Ser Ala Gly Thr Val Glu
                325                 330                 335

Phe Leu Val Asp Ser Lys Lys Asn Phe Tyr Phe Leu Glu Met Asn Thr
            340                 345                 350

Arg Leu Gln Val Glu His Pro Val Thr Glu Cys Ile Thr Gly Leu Asp
        355                 360                 365

Leu Val Gln Glu Met Ile Arg Val Ala Lys Gly Tyr Pro Leu Arg His
    370                 375                 380

Lys Gln Ala Asp Ile Arg Ile Asn Gly Trp Ala Val Glu Cys Arg Val
385                 390                 395                 400

Tyr Ala Glu Asp Pro Tyr Lys Ser Phe Gly Leu Pro Ser Ile Gly Arg
                405                 410                 415

Leu Ser Gln Tyr Gln Glu Pro Leu His Leu Pro Gly Val Arg Val Asp
            420                 425                 430

Ser Gly Ile Gln Pro Gly Ser Asp Ile Ser Ile Tyr Tyr Asp Pro Met
        435                 440                 445

Ile Ser Lys Leu Ile Thr Tyr Gly Ser Asp Arg Thr Glu Ala Leu Lys
    450                 455                 460

Arg Met Ala Asp Ala Leu Asp Asn Tyr Val Ile Arg Gly Val Thr His
465                 470                 475                 480

Asn Ile Ala Leu Leu Arg Glu Val Ile Ile Asn Ser Arg Phe Val Lys
```

```
                485                 490                 495

Gly Asp Ile Ser Thr Lys Phe Leu Ser Asp Val Tyr Pro Asp Gly Phe
            500                 505                 510

Lys Gly His Met Leu Thr Lys Ser Glu Lys Asn Gln Leu Leu Ala Ile
        515                 520                 525

Ala Ser Ser Leu Phe Val Ala Phe Gln Leu Arg Ala Gln His Phe Gln
    530                 535                 540

Glu Asn Ser Arg Met Pro Val Ile Lys Pro Asp Ile Ala Asn Trp Glu
545                 550                 555                 560

Leu Ser Val Lys Leu His Asp Lys Val His Thr Val Val Ala Ser Asn
                565                 570                 575

Asn Gly Ser Val Phe Ser Val Glu Val Asp Gly Ser Lys Leu Asn Val
            580                 585                 590

Thr Ser Thr Trp Asn Leu Ala Ser Pro Leu Leu Ser Val Ser Val Asp
        595                 600                 605

Gly Thr Gln Arg Thr Val Gln Cys Leu Ser Arg Glu Ala Gly Gly Asn
    610                 615                 620

Met Ser Ile Gln Phe Leu Gly Thr Val Val Ala Glu Gly Gln Glu Ile
625                 630                 635                 640

Cys Val Ile Glu Ala Met Lys Met Gln Asn Ser Met Thr Ala Gly Lys
                645                 650                 655

Thr Gly Thr Val Lys Ser Val His Cys Gln Ala Gly Asp Thr Val Gly
            660                 665                 670

Glu Gly Asp Leu Leu Val Glu Leu Glu
        675                 680


<210> SEQ ID NO 28
<211> LENGTH: 539
<212> TYPE: PRT
<213> ORGANISM: Homo sapiens
<220> FEATURE:
<221> NAME/KEY: MISC_FEATURE
<222> LOCATION: (1)..(539)
<223> OTHER INFORMATION: UniProtKB-Swiss-Prot Accession No. P05166-1
      Amino Acid Sequence

<400> SEQUENCE: 28

Met Ala Ala Ala Leu Arg Val Ala Ala Val Gly Ala Arg Leu Ser Val
1               5                   10                  15

Leu Ala Ser Gly Leu Arg Ala Ala Val Arg Ser Leu Cys Ser Gln Ala
            20                  25                  30

Thr Ser Val Asn Glu Arg Ile Glu Asn Lys Arg Arg Thr Ala Leu Leu
        35                  40                  45

Gly Gly Gly Gln Arg Arg Ile Asp Ala Gln His Lys Arg Gly Lys Leu
    50                  55                  60

Thr Ala Arg Glu Arg Ile Ser Leu Leu Leu Asp Pro Gly Ser Phe Val
65                  70                  75                  80

Glu Ser Asp Met Phe Val Glu His Arg Cys Ala Asp Phe Gly Met Ala
                85                  90                  95

Ala Asp Lys Asn Lys Phe Pro Gly Asp Ser Val Val Thr Gly Arg Gly
            100                 105                 110

Arg Ile Asn Gly Arg Leu Val Tyr Val Phe Ser Gln Asp Phe Thr Val
        115                 120                 125

Phe Gly Gly Ser Leu Ser Gly Ala His Ala Gln Lys Ile Cys Lys Ile
    130                 135                 140

Met Asp Gln Ala Ile Thr Val Gly Ala Pro Val Ile Gly Leu Asn Asp
```

```
145                 150                 155                 160

Ser Gly Gly Ala Arg Ile Gln Glu Gly Val Glu Ser Leu Ala Gly Tyr
                165                 170                 175

Ala Asp Ile Phe Leu Arg Asn Val Thr Ala Ser Gly Val Ile Pro Gln
            180                 185                 190

Ile Ser Leu Ile Met Gly Pro Cys Ala Gly Gly Ala Val Tyr Ser Pro
        195                 200                 205

Ala Leu Thr Asp Phe Thr Phe Met Val Lys Asp Thr Ser Tyr Leu Phe
    210                 215                 220

Ile Thr Gly Pro Asp Val Val Lys Ser Val Thr Asn Glu Asp Val Thr
225                 230                 235                 240

Gln Glu Glu Leu Gly Gly Ala Lys Thr His Thr Thr Met Ser Gly Val
                245                 250                 255

Ala His Arg Ala Phe Glu Asn Asp Val Asp Ala Leu Cys Asn Leu Arg
            260                 265                 270

Asp Phe Phe Asn Tyr Leu Pro Leu Ser Ser Gln Asp Pro Ala Pro Val
        275                 280                 285

Arg Glu Cys His Asp Pro Ser Asp Arg Leu Val Pro Glu Leu Asp Thr
    290                 295                 300

Ile Val Pro Leu Glu Ser Thr Lys Ala Tyr Asn Met Val Asp Ile Ile
305                 310                 315                 320

His Ser Val Val Asp Glu Arg Glu Phe Phe Glu Ile Met Pro Asn Tyr
                325                 330                 335

Ala Lys Asn Ile Ile Val Gly Phe Ala Arg Met Asn Gly Arg Thr Val
            340                 345                 350

Gly Ile Val Gly Asn Gln Pro Lys Val Ala Ser Gly Cys Leu Asp Ile
        355                 360                 365

Asn Ser Ser Val Lys Gly Ala Arg Phe Val Arg Phe Cys Asp Ala Phe
    370                 375                 380

Asn Ile Pro Leu Ile Thr Phe Val Asp Val Pro Gly Phe Leu Pro Gly
385                 390                 395                 400

Thr Ala Gln Glu Tyr Gly Gly Ile Ile Arg His Gly Ala Lys Leu Leu
                405                 410                 415

Tyr Ala Phe Ala Glu Ala Thr Val Pro Lys Val Thr Val Ile Thr Arg
            420                 425                 430

Lys Ala Tyr Gly Gly Ala Tyr Asp Val Met Ser Ser Lys His Leu Cys
        435                 440                 445

Gly Asp Thr Asn Tyr Ala Trp Pro Thr Ala Glu Ile Ala Val Met Gly
    450                 455                 460

Ala Lys Gly Ala Val Glu Ile Ile Phe Lys Gly His Glu Asn Val Glu
465                 470                 475                 480

Ala Ala Gln Ala Glu Tyr Ile Glu Lys Phe Ala Asn Pro Phe Pro Ala
                485                 490                 495

Ala Val Arg Gly Phe Val Asp Asp Ile Ile Gln Pro Ser Ser Thr Arg
            500                 505                 510

Ala Arg Ile Cys Cys Asp Leu Asp Val Leu Ala Ser Lys Lys Val Gln
        515                 520                 525

Arg Pro Trp Arg Lys His Ala Asn Ile Pro Leu
    530                 535
```

<210> SEQ ID NO 29
<211> LENGTH: 559
<212> TYPE: PRT
<213> ORGANISM: Homo sapiens

```
<220> FEATURE:
<221> NAME/KEY: MISC_FEATURE
<222> LOCATION: (1)..(559)
<223> OTHER INFORMATION: UniProtKB-Swiss-Prot Accession No. P05166-2
      Amino Acid Sequence

<400> SEQUENCE: 29

Met Ala Ala Ala Leu Arg Val Ala Ala Val Gly Ala Arg Leu Ser Val
1               5                   10                  15

Leu Ala Ser Gly Leu Arg Ala Ala Val Arg Ser Leu Cys Ser Gln Ala
            20                  25                  30

Thr Ser Val Asn Glu Arg Ile Glu Asn Lys Arg Arg Thr Ala Leu Leu
        35                  40                  45

Gly Gly Gly Gln Arg Arg Ile Asp Ala Gln His Lys Arg Gly Lys Leu
    50                  55                  60

Thr Ala Arg Glu Arg Ile Ser Leu Leu Leu Asp Pro Gly Ser Phe Val
65                  70                  75                  80

Glu Ser Asp Met Phe Val Glu His Arg Cys Ala Asp Phe Gly Met Ala
                85                  90                  95

Ala Asp Lys Asn Lys Phe Pro Gly Asp Ser Val Val Thr Gly Arg Gly
            100                 105                 110

Arg Ile Asn Gly Arg Leu Val Tyr Val Phe Ser Gln Gln Ile Ile Gly
        115                 120                 125

Trp Ala Gln Trp Leu Pro Leu Val Ile Ser Ala Leu Trp Glu Ala Glu
    130                 135                 140

Asp Phe Thr Val Phe Gly Gly Ser Leu Ser Gly Ala His Ala Gln Lys
145                 150                 155                 160

Ile Cys Lys Ile Met Asp Gln Ala Ile Thr Val Gly Ala Pro Val Ile
                165                 170                 175

Gly Leu Asn Asp Ser Gly Gly Ala Arg Ile Gln Glu Gly Val Glu Ser
            180                 185                 190

Leu Ala Gly Tyr Ala Asp Ile Phe Leu Arg Asn Val Thr Ala Ser Gly
        195                 200                 205

Val Ile Pro Gln Ile Ser Leu Ile Met Gly Pro Cys Ala Gly Gly Ala
    210                 215                 220

Val Tyr Ser Pro Ala Leu Thr Asp Phe Thr Phe Met Val Lys Asp Thr
225                 230                 235                 240

Ser Tyr Leu Phe Ile Thr Gly Pro Asp Val Val Lys Ser Val Thr Asn
                245                 250                 255

Glu Asp Val Thr Gln Glu Glu Leu Gly Gly Ala Lys Thr His Thr Thr
            260                 265                 270

Met Ser Gly Val Ala His Arg Ala Phe Glu Asn Asp Val Asp Ala Leu
        275                 280                 285

Cys Asn Leu Arg Asp Phe Phe Asn Tyr Leu Pro Leu Ser Ser Gln Asp
    290                 295                 300

Pro Ala Pro Val Arg Glu Cys His Asp Pro Ser Asp Arg Leu Val Pro
305                 310                 315                 320

Glu Leu Asp Thr Ile Val Pro Leu Glu Ser Thr Lys Ala Tyr Asn Met
                325                 330                 335

Val Asp Ile Ile His Ser Val Val Asp Glu Arg Glu Phe Phe Glu Ile
            340                 345                 350

Met Pro Asn Tyr Ala Lys Asn Ile Ile Val Gly Phe Ala Arg Met Asn
        355                 360                 365

Gly Arg Thr Val Gly Ile Val Gly Asn Gln Pro Lys Val Ala Ser Gly
    370                 375                 380
```

```
Cys Leu Asp Ile Asn Ser Ser Val Lys Gly Ala Arg Phe Val Arg Phe
385                 390                 395                 400

Cys Asp Ala Phe Asn Ile Pro Leu Ile Thr Phe Val Asp Val Pro Gly
                405                 410                 415

Phe Leu Pro Gly Thr Ala Gln Glu Tyr Gly Gly Ile Ile Arg His Gly
            420                 425                 430

Ala Lys Leu Leu Tyr Ala Phe Ala Glu Ala Thr Val Pro Lys Val Thr
        435                 440                 445

Val Ile Thr Arg Lys Ala Tyr Gly Gly Ala Tyr Asp Val Met Ser Ser
    450                 455                 460

Lys His Leu Cys Gly Asp Thr Asn Tyr Ala Trp Pro Thr Ala Glu Ile
465                 470                 475                 480

Ala Val Met Gly Ala Lys Gly Ala Val Glu Ile Ile Phe Lys Gly His
                485                 490                 495

Glu Asn Val Glu Ala Ala Gln Ala Glu Tyr Ile Glu Lys Phe Ala Asn
            500                 505                 510

Pro Phe Pro Ala Ala Val Arg Gly Phe Val Asp Asp Ile Ile Gln Pro
        515                 520                 525

Ser Ser Thr Arg Ala Arg Ile Cys Cys Asp Leu Asp Val Leu Ala Ser
    530                 535                 540

Lys Lys Val Gln Arg Pro Trp Arg Lys His Ala Asn Ile Pro Leu
545                 550                 555
```

```
<210> SEQ ID NO 30
<211> LENGTH: 3843
<212> TYPE: DNA
<213> ORGANISM: Artificial Sequence
<220> FEATURE:
<223> OTHER INFORMATION: Description of Artificial Sequence: DTC430

<400> SEQUENCE: 30

ttggccactc cctctctgcg cgctcgctcg ctcactgagg ccgggcgacc aaaggtcgcc     60

cgacgcccgg gctttgcccg ggcggcctca gtgagcgagc gagcgcgcag agagggagtg    120

gccaactcca tcactagggg ttcctcgtta cataacttac ggtaaatggc ccgcctggct    180

gaccgcccaa cgacccccgc ccattgacgt caataatgac gtatgttccc atagtaacgc    240

caatagggac tttccattga cgtcaatggg tggactattt acggtaaact gcccacttgg    300

cagtacatca agtgtatcat atgccaagta cgccccctat tgacgtcaat gacggtaaat    360

ggcccgcctg gcattatgcc cagtacatga ccttatggga ctttcctact tggcagtaca    420

tctacgtatt agtcatcgct attaccatgc gtcgaggtga gccccacgtt ctgcttcact    480

ctccccatct cccccccctc cccaccccca attttgtatt tatttatttt ttaattattt    540

tatgcagcga tgggggcggg gggggggggg gcgcgcgcca ggcggggcgg ggcggggcga    600

ggggcggggc ggggcgaggc ggagaggtgc ggcggcagcc aatcagagcg gcgcgctccg    660

aaagtttcct tttatggcga ggcggcggcg gcggcggccc tataaaaagc gaagcgcgcg    720

gcgggcgatc agcttacttg tggtaccgag ctcggatcct gagaacttca gggtgagtct    780

atgggaccct tgatgttttc tttccccttc ttttctatgg ttaagttcat gtcataggaa    840

ggggagaagt aacagggtac acatattgac caaatcaggg taattttgca tttgtaattt    900

taaaaaatgc tttcttcttt taatatactt ttttgtttat cttatttcta atactttccc    960

taatctcttt ctttcagggc aataatgata caatgtatca tgcctctttg caccattcta   1020

aagaataaca gtgataattt ctgggttaag gcaatagcaa tatttctgca tataaatatt   1080
```

```
tctgcatata aattgtaact gatgtaagag gtttcatatt gctaatagca gctacaatcc   1140
agctaccatt ctgcttttat tttatggttg ggataaggct ggattattct gagtccaagc   1200
taggcccttt tgctaatcat gttcatacct cttatcttcc tcccacagct cctgggcaac   1260
gtgctggtct gtgtgctggc ccatcacttt ggcaaagaat tgatcgccgc caccatggcg   1320
gggttctggg tcgggacagc accgctggtc gctgccggac ggcgtgggcg gtggccgccg   1380
cagcagctga tgctgagcgc ggcgctgcgg accctgaagc atgttctgta ctattcaaga   1440
cagtgcttaa tggtgtcccg taatcttggt tcagtgggat atgatcctaa tgaaaaaact   1500
tttgataaaa ttcttgttgc taatagagga gaaattgcat gtcgggttat tagaacttgc   1560
aagaagatgg gcattaagac agttgccatc cacagtgatg ttgatgctag ttctgttcat   1620
gtgaaaatgg cggatgaggc tgtctgtgtt ggcccagctc ccaccagtaa aagctacctc   1680
aacatggatg ccatcatgga agccattaag aaaaccaggg cccaagctgt acatccaggt   1740
tatggattcc tttcagaaaa caaagaattt gccagatgtt tggcagcaga agatgtcgtt   1800
ttcattggac ctgacacaca tgctattcaa gccatgggcg acaagattga aagcaaatta   1860
ttagctaaga aagcagaggt taatacaatc cctggctttg atggagtagt caaggatgca   1920
gaagaagctg tcagaattgc aagggaaatt ggctaccctg tcatgatcaa ggcctcagca   1980
ggtggtggtg ggaaaggcat gcgcattgct tgggatgatg aagagaccag ggatggtttt   2040
agattgtcat ctcaagaagc tgcttctagt tttggcgatg atagactact aatagaaaaa   2100
tttattgata atcctcgtca tatagaaatc caggttctag gtgataaaca tgggaatgct   2160
ttatggctta atgaaagaga gtgctcaatt cagagaagaa atcagaaggt ggtggaggaa   2220
gcaccaagca ttttttggga tgcggagact cgaagagcga tgggagaaca agctgtagct   2280
cttgccagag cagtaaaata ttcctctgct gggaccgtgg agttccttgt ggactctaag   2340
aagaattttt atttcttgga aatgaataca agactccagg ttgagcatcc tgtcacagaa   2400
tgcattactg gcctggacct agtccaggaa atgatccgtg ttgctaaggg ctaccctctc   2460
aggcacaaac aagctgatat tcgcatcaac ggctgggcag ttgaatgtcg ggtttatgct   2520
gaggacccct acaagtcttt tggtttacca tctattggga gattgtctca gtaccaagaa   2580
ccgttacatc tacctggtgt ccgagtggac agtggcatcc aaccaggaag tgatattagc   2640
atttattatg atcctatgat ttcaaaacta atcacatatg gctctgatag aactgaggca   2700
ctgaagagaa tggcagatgc actggataac tatgttattc gaggtgttac acataatatt   2760
gcattacttc gagaggtgat aatcaactca cgctttgtaa aaggagacat cagcactaaa   2820
tttctctccg atgtgtatcc tgatggcttc aaaggacaca tgctaaccaa gagtgagaag   2880
aaccagttat tggcaatagc atcatcattg tttgtggcat tccagttaag agcacaacat   2940
tttcaagaaa attcaagaat gcctgttatt aaaccagaca tagccaactg ggagctctca   3000
gtaaaattgc atgataaagt tcataccgta gtagcatcaa acaatgggtc agtgttctcg   3060
gtggaagttg atgggtcgaa actaaatgtg accagcacgt ggaacctggc ttcgccctta   3120
ttgtctgtca gcgttgatgg cactcagagg actgtccagt gtctttctcg agaagcaggt   3180
ggaaacatga gcattcagtt tcttggtaca gtgtacaagg tgaatatctt aaccagactt   3240
gccgcagaat tgaacaaatt tatgctggaa aaagtgactg aggacacaag cagtgttctg   3300
cgttccccga tgcccggagt ggtggtggcc gtctctgtca agcctggaga cgcggtagca   3360
gaaggtcaag aaatttgtgt gattgaagcc atgaaaatgc agaatagtat gacagctggg   3420
```

```
aaaactggca cggtgaaatc tgtgcactgt caagctggag acacagttgg agaaggggat   3480

ctgctcgtgg agctggaatg aatccagaca tgataagata cattgatgag tttggacaaa   3540

ccacaactag aatgcagtga aaaaaatgct ttatttgtga aatttgtgat gctattgctt   3600

tatttgtaac cattataagc tgcaataaac aagttaacaa caacaattgc attcatttta   3660

tgtttcaggt tcagggggag gtgtgggagg tttttagag gaacccctag tgatggagtt   3720

ggccactccc tctctgcgcg ctcgctcgct cactgaggcc gcccgggcaa agcccgggcg   3780

tcgggcgacc tttggtcgcc cggcctcagt gagcgagcga gcgcgcagag agggagtggc   3840

caa                                                                3843
```

<210> SEQ ID NO 31
<211> LENGTH: 3276
<212> TYPE: DNA
<213> ORGANISM: Artificial Sequence
<220> FEATURE:
<223> OTHER INFORMATION: Description of Artificial Sequence: DTC504

<400> SEQUENCE: 31

```
ttggccactc cctctctgcg cgctcgctcg ctcactgagg ccgggcgacc aaaggtcgcc     60

cgacgcccgg gctttgcccg ggcggcctca gtgagcgagc gagcgcgcag agagggagtg    120

gccaactcca tcactagggg ttcctcgtta cataacttac ggtaaatggc ccgcctggct    180

gaccgcccaa cgacccccgc ccattgacgt caataatgac gtatgttccc atagtaacgc    240

caatagggac tttccattga cgtcaatggg tggactattt acggtaaact gcccacttgg    300

cagtacatca agtgtatcat atgccaagta cgccccctat tgacgtcaat gacggtaaat    360

ggcccgcctg gcattatgcc cagtacatga ccttatggga ctttcctact tggcagtaca    420

tctacgtatt agtcatcgct attaccatgc gtcgaggtga gccccacgtt ctgcttcact    480

ctccccatct cccccccctc cccaccccca attttgtatt tatttatttt ttaattattt    540

tatgcagcga tgggggcggg gggggggggg gcgcgcgcca ggcggggcgg ggcggggcga    600

ggggcggggc ggggcgaggc ggagaggtgc ggcggcagcc aatcagagcg gcgcgctccg    660

aaagtttcct tttatggcga ggcggcggcg gcggcggccc tataaaaagc gaagcgcgcg    720

gcgggcgatc agcttacttg tggtaccgag ctcggatcct gagaacttca gggtgagtct    780

atgggaccct tgatgttttc tttccccttc ttttctatgg ttaagttcat gtcataggaa    840

ggggagaagt aacagggtac acatattgac caaatcaggg taattttgca tttgtaattt    900

taaaaaatgc tttcttcttt taatatactt ttttgtttat cttatttcta atactttccc    960

taatctcttt ctttcagggc aataatgata caatgtatca tgcctctttg caccattcta   1020

aagaataaca gtgataattt ctgggttaag gcaatagcaa tatttctgca tataaatatt   1080

tctgcatata aattgtaact gatgtaagag gtttcatatt gctaatagca gctacaatcc   1140

agctaccatt ctgcttttat tttatggttg ggataaggct ggattattct gagtccaagc   1200

taggcccttt tgctaatcat gttcatacct cttatcttcc tcccacagct cctgggcaac   1260

gtgctggtct gtgtgctggc ccatcacttt ggcaaagaat tgatcgccgc caccatggcg   1320

gcggcattac gggtggcggc ggtcggggca aggctcagcg ttctggcgag cggtctccgc   1380

gccgcggtcc gcagcctttg cagccaggcc acctctgtta acgaacgcat cgaaaacaag   1440

cgccggaccg cgctgctggg agggggccaa cgccgtattg acgcgcagca caagcgagga   1500

aagctaacag ccagggagag gatcagtctc ttgctggacc ctggcagctt tgttgagagc   1560

gacatgtttg tggaacacag atgtgcagat tttggaatgg ctgctgataa gaataagttt   1620
```

-continued

```
cctggagaca gcgtggtcac tggacgaggc cgaatcaatg gaagattggt ttatgtcttc   1680
agtcaggatt ttacagtttt tggaggcagt ctgtcaggag cacatgccca aaagatctgc   1740
aaaatcatgg accaggccat aacggtgggg gctccagtga ttgggctgaa tgactctggg   1800
ggagcacgga tccaagaagg agtggagtct ttggctggct atgcagacat ctttctgagg   1860
aatgttacgg catccggagt catccctcag atttctctga tcatgggccc atgtgctggt   1920
ggggccgtct actccccagc cctaacagac ttcacgttca tggtaaagga cacctcctac   1980
ctgttcatca ctggccctga tgttgtgaag tctgtcacca atgaggatgt tacccaggag   2040
gagctcggtg gtgccaagac ccacaccacc atgtcaggtg tggcccacag agcttttgaa   2100
aatgatgttg atgccttgtg taatctccgg gatttcttca actacctgcc cctgagcagt   2160
caggacccgg ctcccgtccg tgagtgccac gatcccagtg accgtctggt tcctgagctt   2220
gacacaattg tccctttgga atcaaccaaa gcctacaaca tggtggacat catacactct   2280
gttgttgatg agcgtgaatt ttttgagatc atgcccaatt atgccaagaa catcattgtt   2340
ggttttgcaa gaatgaatgg gaggactgtt ggaattgttg gcaaccaacc taaggtggcc   2400
tcaggatgct tggatattaa ttcatctgtg aaaggggctc gttttgtcag attctgtgat   2460
gcattcaata ttccactcat cacttttgtt gatgtccctg gctttctacc tggcacagca   2520
caggaatacg gggcatcat ccggcatggt gccaagcttc tctacgcatt tgctgaggca   2580
actgtaccca aagtcacagt catcaccagg aaggcctatg gaggtgccta tgatgtcatg   2640
agctctaagc acctttgtgg tgataccaac tatgcctggc ccaccgcaga gattgcagtc   2700
atgggagcaa agggcgctgt ggagatcatc ttcaaagggc atgagaatgt ggaagctgct   2760
caggcagagt acatcgagaa gtttgccaac cctttccctg cagcagtgcg agggtttgtg   2820
gatgacatca tccaaccttc ttccacacgt gcccgaatct gctgtgacct ggatgtcttg   2880
gccagcaaga aggtacaacg tccttggaga aaacatgcaa atattccatt gtgaatccag   2940
acatgataag atacattgat gagtttggac aaaccacaac tagaatgcag tgaaaaaaat   3000
gctttatttg tgaaatttgt gatgctattg ctttatttgt aaccattata agctgcaata   3060
aacaagttaa caacaacaat tgcattcatt ttatgtttca ggttcagggg gaggtgtggg   3120
aggtttttta gaggaacccc tagtgatgga gttggccact ccctctctgc gcgctcgctc   3180
gctcactgag gccgcccggg caaagcccgg gcgtcgggcg acctttggtc gcccggcctc   3240
agtgagcgag cgagcgcgca gagagggagt ggccaa                             3276
```

GENE THERAPY FOR TREATING PROPIONIC ACIDEMIA

CROSS-REFERENCE TO RELATED APPLICATIONS

The present application is a U.S. national stage application, filed under 35 U.S.C. § 371, of International Application No. PCT/US2021/024892, filed Mar. 30, 2021, which claims the benefit of and priority to U.S. Provisional Application No. 63/002,541, filed on Mar. 31, 2020, the entire disclosure of each of which is incorporated herein by reference in its entirety for all purposes.

SEQUENCE LISTING

The instant application contains a Sequence Listing which has been submitted electronically in ASCII format and is hereby incorporated by reference in its entirety. Said ASCII copy, created on Mar. 24, 2021, is named ULP-009WO_SL.txt and is 103,435 bytes in size.

TECHNICAL FIELD OF THE INVENTION

The present disclosure relates generally to recombinant adeno-associated virus (rAAV) and methods of their use in gene therapy for treating propionic acidemia (PA).

BACKGROUND OF THE INVENTION

Propionic acidemia (PA), also known as propionic aciduria, is an inborn error of organic acid metabolism caused by a deficiency of active propionyl-CoA carboxylase (PCC), an enzyme needed to convert propionyl-CoA to (D)-methylmalonyl-CoA, a key step in the catabolic pathway for odd chain fatty acids and the propiogenic amino acids, particularly isoleucine, threonine, methionine, and valine. The PCC enzyme is composed of two non-identical subunits, α and β, which are encoded by the PCCA and PCCB genes, respectively. A propionyl-CoA carboxylase deficiency can result from mutations in either PCCA or PCCB. In one study, a mutation analysis of 30 patients with PA was performed and found that 15 patients were α-subunit deficient and 15 patients were β-subunit deficient. See Yang et al., 2004, *Mol Genet and Metab.* 81: 335-342.

The estimated incidence of PA is 1:105,000 to 1:130,000 in the United States. This rare autosomal recessive metabolic disorder presents in the early neonatal period with poor feeding, vomiting, lethargy, seizures, and lack of muscle tone. Left untreated, death can occur quickly, due to secondary hyperammonemia, infection, cardiomyopathy, or basal ganglial stroke. PA can be diagnosed almost immediately in newborns and the disease is included in newborn screening panels in the United States.

PA is currently managed by dietary restriction of amino acid precursors, supplementation of L-carnitine to address diminished carnitine levels, and administration of antibiotics to reduce propionic acid production by intestinal bacteria. Liver transplantation is gaining a role in the management of PA in situations where the patient cannot be managed by standard treatment. However, despite the aggressive efforts to address the disease through complex combinations of nutritional, cofactor, and antibiotic therapy, the long-term prognosis for patients with PA remains poor. See van der Meer et al., 1996, *Eur. J. Pediatr.* 155: 205-210. Accordingly, improved therapeutic approaches are needed that address the underlying cause of the disease, namely the deficiency of PCC.

One strategy that has gained interest in recent years is the use of adeno-associated virus (AAV) vectors for in vivo delivery of a functional copy of a deficient protein. For the treatment of PA, the present applicant has previously described recombinant AAV (rAAV) capable of delivering a gene encoding a functional PCCA protein or a gene encoding a functional PCCB protein. See. e.g., PCT/US2019/054003 (published as WO/2020/072451), which is herein incorporated by reference in its entirety. For optimal AAV-based gene therapy, it is important to maximize transgene expression levels, which in turn enables a reduction in the vector dose required to achieve therapeutic efficacy and decreases the risk of unwanted dose-related immune responses.

The present invention addresses the need for high-expression rAAV for the treatment of PA. Notably, it has been discovered by the present applicant that insertion of a human β-globin IVS2 intron sequence (SEQ ID NO: 1) into a PA gene therapy vector substantially and surprisingly increases transgene expression relative to comparator vectors expressing an alternative intron sequence. Thus, rAAVs of the invention can provide unexpectedly high transgene expression, thereby reducing the vector dose required for successful treatment of PA.

SUMMARY OF THE INVENTION

This invention provides compositions and methods of their use in gene therapy. More specifically, the present disclosure provides recombinant adeno-associated virus (rAAV) comprising an adeno-associated virus (AAV) capsid, and a vector genome packaged therein useful for the treatment of PA.

In one aspect, the present disclosure provides a recombinant adeno-associated virus (rAAV) comprising an AAV capsid, and a vector genome packaged therein, wherein said vector genome comprises: (a) a promoter sequence; (b) an intron sequence at least 90% identical to SEQ ID NO: 1; and (c) a partial or complete coding sequence for PCCA or an isoform thereof, or a functional fragment or functional variant thereof.

In another aspect, the present disclosure provides a recombinant adeno-associated virus (rAAV) comprising an AAV capsid, and a vector genome packaged therein, wherein said vector genome comprises: (a) a 5'-inverted terminal repeat sequence (5'-ITR) sequence; (b) a promoter sequence; (c) an intron sequence at least 90% identical to SEQ ID NO: 1; (d) a partial or complete coding sequence for PCCA or an isoform thereof, or a functional fragment or functional variant thereof; and (e) a 3'-inverted terminal repeat sequence (3'-ITR) sequence.

In another aspect, the present disclosure provides a recombinant adeno-associated virus (rAAV) comprising an AAV capsid, and a vector genome packaged therein, wherein said vector genome comprises: (a) a 5'-ITR sequence; (b) an enhancer sequence; (c) a promoter sequence; (d) an intron sequence at least 90% identical to SEQ ID NO: 1; (e) a partial or complete coding sequence for PCCA; (f) a polyadenylation signal sequence; and (g) a 3'-ITR sequence.

In various aspects described herein, the packaged vector genome comprises an intron sequence which is at least 90% identical to SEQ ID NO: 1. In some embodiments, the packaged vector genome comprises an intron sequence which is at least 90%, 91%, 92%, 93%, 94%, 95%, 96%, 97%, 98%, 99%, 99.5%, or 99.9% identical to SEQ ID NO: 1. In some embodiments, the intron sequence comprises or consists of SEQ ID NO: 1.

In one embodiment, the partial or complete coding sequence for PCCA is a wild-type coding sequence. In an alternative embodiment, the partial or complete coding sequence for PCCA is a codon-optimized coding sequence. In one exemplary embodiment, the partial or complete coding sequence for PCCA is codon-optimized for expression in humans.

In some embodiments, PCCA is encoded by the wild-type coding sequence shown in SEQ ID NO: 2. In another embodiment, a coding sequence expressing a natural isoform or variant of PCCA may be used, such as those shown in UniProtKB/Swiss-Prot Accession Nos. P05165-1 (SEQ ID NO: 25), P05165-2 (SEQ ID NO: 26), and P05165-3 (SEQ ID NO: 27). In certain embodiments, PCCA is encoded by a codon-optimized coding sequence. In some embodiments, PCCA is encoded by a codon-optimized coding sequence that is less than 80% identical to the wild-type coding sequence shown in SEQ ID NO: 2. In some exemplary embodiments, PCCA is encoded by a codon-optimized coding sequence selected from SEQ ID NOs: 3-7. In some embodiments, PCCA is encoded by a codon-optimized coding sequence which is at least 80% identical to a sequence selected from SEQ ID NOs: 3-7. In some embodiments, PCCA is encoded by a codon-optimized coding sequence which is at least 90% identical to a sequence selected from SEQ ID NOs: 3-7. In some embodiments, PCCA is encoded by a codon-optimized coding sequence which is at least 95% identical to a sequence selected from SEQ ID NOs: 3-7. In some embodiments, the coding sequence for PCCA may further comprise a stop codon (TGA, TAA, or TAG) at the 3' end. In some embodiments, the expressed PCCA comprises or consists of an amino acid sequence of SEQ ID NO: 19.

In some embodiments, the present disclosure provides a recombinant adeno-associated virus (rAAV) comprising an AAV capsid, and a vector genome packaged therein, wherein said vector genome comprises a sequence which is at least 90%, 91%, 92%, 93%, 94%, 95%, 96%, 97%, 98%, 99%, 99.5%, or 99.9% identical to SEQ ID NO: 30. In some embodiments, the vector genome comprises SEQ ID NO: 30. In some embodiments, vector genome consists of SEQ ID NO: 30.

In another aspect, the present disclosure provides a recombinant adeno-associated virus (rAAV) comprising an AAV capsid, and a vector genome packaged therein, wherein said vector genome comprises: (a) a promoter sequence; (b) an intron sequence at least 90% identical to SEQ ID NO: 1; and (c) a partial or complete coding sequence for PCCB or an isoform thereof, or a functional fragment or functional variant thereof.

In another aspect, the present disclosure provides a recombinant adeno-associated virus (rAAV) comprising an AAV capsid, and a vector genome packaged therein, wherein said vector genome comprises: (a) a 5'-ITR sequence; (b) a promoter sequence; (c) an intron sequence at least 90% identical to SEQ ID NO: 1; (d) a partial or complete coding sequence for PCCB or an isoform thereof, or a functional fragment or functional variant thereof; and (e) a 3'-ITR sequence.

In another aspect, the present disclosure provides a recombinant adeno-associated virus (rAAV) comprising an AAV capsid, and a vector genome packaged therein, wherein said vector genome comprises: (a) a 5'-ITR sequence; (b) an enhancer sequence; (c) a promoter sequence; (d) an intron sequence at least 90% identical to SEQ ID NO: 1; (e) a partial or complete coding sequence for PCCB; (f) a polyadenylation signal sequence; and (g) a 3'-ITR sequence.

In one embodiment, the partial or complete coding sequence for PCCB is a wild-type coding sequence. In an alternative embodiment, the partial or complete coding sequence for PCCB is a codon-optimized coding sequence. In one exemplary embodiment, the partial or complete coding sequence for PCCB is codon-optimized for expression in humans.

In some embodiments, PCCB is encoded by the wild-type coding sequence shown in SEQ ID NO: 8. In another embodiment, a coding sequence expressing a natural isoform or variant of PCCB may be used, such as those shown in UniProtKB/Swiss-Prot Accession Nos. P05166-1 (SEQ ID NO: 28) and P05166-2 (SEQ ID NO: 29). In alternative embodiments, PCCB is encoded by a codon-optimized coding sequence. In some embodiments, PCCB is encoded by a codon-optimized coding sequence that is less than 80% identical to the wild-type coding sequence shown in SEQ ID NO: 8. In some exemplary embodiments, PCCB is encoded by a codon-optimized coding sequence selected from SEQ ID NOs: 9-13. In some embodiments, PCCB is encoded by a codon-optimized coding sequence which is at least 80% identical to a sequence selected from SEQ ID NOs: 9-13. In some embodiments, PCCB is encoded by a codon-optimized coding sequence which is at least 90% identical to a sequence selected from SEQ ID NOs: 9-13. In some embodiments, PCCB is encoded by a codon-optimized coding sequence which is at least 95% identical to a sequence selected from SEQ ID NOs: 9-13. In some embodiments, the coding sequence for PCCB may further comprise a stop codon (TGA, TAA, or TAG) at the 3' end. In some embodiments, the expressed PCCB comprises or consists of an amino acid sequence of SEQ ID NO: 20.

In some embodiments, the present disclosure provides a recombinant adeno-associated virus (rAAV) comprising an AAV capsid, and a vector genome packaged therein, wherein said vector genome comprises a sequence which is at least 90%, 91%, 92%, 93%, 94%, 95%, 96%, 97%, 98%, 99%, 99.5%, or 99.9% identical to SEQ ID NO: 31. In some embodiments, the vector genome comprises SEQ ID NO: 31. In some embodiments, vector genome consists of SEQ ID NO: 31.

In one embodiment, the promoter is selected from a chicken β-actin (CBA) promoter, a cytomegalovirus (CMV) immediate early gene promoter, a transthyretin (TTR) promoter, a thyroxine binding globulin (TBG) promoter, an alpha-1 anti-trypsin (A1AT) promoter, a CAG promoter (constructed using the CMV early enhancer element, the promoter, the first exon, and the first intron of CBA gene, and the splice acceptor of the rabbit beta-globin gene), a PCCA gene-specific endogenous promoter, and a PCCB gene-specific endogenous promoter. In an exemplary embodiment, the promoter is the CBA promoter. In one embodiment, the CBA promoter comprises or consists of SEQ ID NO: 21.

In some embodiments, the packaged vector genome comprises a 5'-ITR sequence and/or a 3'-ITR sequence. In certain embodiments, the 5'-ITR sequence is from AAV2. In some embodiments, the 3'-ITR sequence is from AAV2. In some embodiments, the 5'-ITR sequence and/or the 3'-ITR sequence are from AAV2. In some embodiments, the 5'-ITR sequence and/or the 3'-ITR sequence comprise or consist of SEQ ID NO: 18. In other embodiments, the 5'-ITR sequence and/or the 3'-ITR sequence are from a non-AAV2 source In some embodiments, the packaged vector genome further comprises one or more enhancer sequences. In one embodiment, the enhancer is selected from a cytomegalovirus (CMV) immediate early gene enhancer, a transthyretin enhancer (enTTR), a chicken β-actin (CBA) enhancer, an En34 enhancer, and an apolipoprotein E (ApoE) enhancer. In an exemplary embodiment, the enhancer is the CMV immediate early gene enhancer. In one embodiment, the CMV immediate early gene enhancer comprises or consists of SEQ ID NO: 22. In certain embodiments, the enhancer is located upstream of the promoter sequence.

In some embodiments, packaged vector genome further comprises a consensus Kozak sequence. In some embodiments, the consensus Kozak sequence is located downstream of an intron sequence. In one embodiment, the consensus Kozak sequence is GCCGCC (SEQ ID NO: 24). In certain embodiments, the consensus Kozak sequence is located upstream of coding sequence for PCCA. In certain embodiments, the consensus Kozak sequence is located upstream of coding sequence for PCCB.

In some embodiments, packaged vector genome further comprises a polyadenylation signal sequence. In certain embodiments, the polyadenylation signal sequence is selected from an SV40 polyadenylation signal sequence, a bovine growth hormone (BGH) polyadenylation signal sequence, and a rabbit beta globin polyadenylation signal sequence. In an exemplary embodiment, the polyadenylation signal sequence is the SV40 polyadenylation signal sequence. In one embodiment, the SV40 polyadenylation signal sequence comprises or consists of SEQ ID NO: 23.

In some embodiments, the AAV capsid is from an AAV of serotype 8, 1, 2, 3, 4, 5, 6, 7, 9, 10, 11, 12, rh10, hu37 (i.e., AAV8, AAV1, AAV2, AAV3, AAV4, AAV5, AAV6, AAV7, AAV9, AAV10, AAV11, AAV12, AAVrh10, AAVhu37), or an engineered variant thereof. In an exemplary embodiment, the AAV capsid is an AAV serotype 9 (AAV9) capsid, an AAV9 variant capsid, an AAV serotype 8 (AAV8) capsid, an AAV8 variant capsid, or an AAV serotype hu37 (AAVhu37) capsid.

In certain embodiments, the present disclosure provides recombinant adeno-associated virus (rAAV) useful as agents for gene therapy in the treatment of PA, wherein said rAAV comprises an AAV capsid, and a vector genome as described herein packaged therein. In some embodiments, the AAV capsid is from an AAV of serotype 8, 1, 2, 3, 4, 5, 6, 7, 9, 10, 11, 12, rh10, hu37 (i.e., AAV8, AAV1, AAV2, AAV3, AAV4, AAV5, AAV6, AAV7, AAV9, AAV10, AAV11, AAV12, AAVrh10, AAVhu37), or an engineered variant thereof. In an exemplary embodiment, the AAV capsid is an AAV serotype 9 (AAV9) capsid, an AAV9 variant capsid, an AAV serotype 8 (AAV8) capsid, an AAV8 variant capsid, or an AAV serotype hu37 (AAVhu37) capsid.

In certain embodiments, the present disclosure provides an rAAV useful for the treatment of propionic acidemia (PA), said rAAV comprising an AAV capsid, and a vector genome packaged therein, said vector genome comprising as operably linked components in 5' to 3' order: (a) a promoter sequence; (b) an intron sequence at least 90% identical to SEQ ID NO: 1; and (c) a coding sequence for PCCA selected from SEQ ID NOs: 2-7.

In certain embodiments, the present disclosure provides an rAAV useful for the treatment of propionic acidemia (PA), said rAAV comprising an AAV capsid, and a vector genome packaged therein, said vector genome comprising as operably linked components in 5' to 3' order: (a) a 5'-ITR sequence; (b) an enhancer sequence; (c) a promoter sequence; (d) an intron sequence at least 90% identical to SEQ ID NO: 1; (e) a coding sequence for PCCA selected from SEQ ID NOs: 2-7; (f) a polyadenylation signal sequence; and (g) a 3'-ITR sequence.

In certain embodiments, the present disclosure provides an rAAV useful for the treatment of propionic acidemia (PA), said rAAV comprising an AAV capsid, and a vector genome packaged therein, said vector genome comprising as operably linked components in 5' to 3' order: (a) a promoter sequence; (b) an intron sequence at least 90% identical to SEQ ID NO: 1; and (c) a coding sequence for PCCB selected from SEQ ID NOs: 8-13.

In certain embodiments, the present disclosure provides an rAAV useful for the treatment of propionic acidemia (PA), said rAAV comprising an AAV capsid, and a vector genome packaged therein, said vector genome comprising as operably linked components in 5' to 3' order: (a) a 5'-ITR sequence; (b) an enhancer sequence; (c) a promoter sequence; (d) an intron sequence at least 90% identical to SEQ ID NO: 1; (e) a coding sequence for PCCB selected from SEQ ID NOs: 8-13; (f) a polyadenylation signal sequence; and (g) a 3'-ITR sequence.

In certain embodiments, the present disclosure provides an rAAV useful for the treatment of propionic acidemia (PA), said rAAV comprising an AAV8 capsid or AAV9 capsid, and a vector genome packaged therein, said vector genome comprising as operably linked components in 5' to 3' order: (a) a promoter sequence; (b) an intron sequence at least 90% identical to SEQ ID NO: 1; and (c) a coding sequence for PCCA selected from SEQ ID NOs: 2-7.

In certain embodiments, the present disclosure provides an rAAV useful for the treatment of propionic acidemia (PA), said rAAV comprising an AAV8 capsid or AAV9 capsid, and a vector genome packaged therein, said vector genome comprising as operably linked components in 5' to 3' order: (a) a promoter sequence; (b) an intron sequence at least 90% identical to SEQ ID NO: 1; and (c) a coding sequence for PCCB selected from SEQ ID NOs: 8-13.

In certain embodiments, the present disclosure provides an rAAV useful for the treatment of propionic acidemia (PA), said rAAV comprising an AAV8 capsid or AAV9 capsid, and a vector genome packaged therein, said vector genome comprising as operably linked components in 5' to 3' order: (a) an AAV2 5'-ITR sequence; (b) a CMV enhancer sequence; (c) a CBA promoter sequence; (d) an intron sequence at least 90% identical to SEQ ID NO: 1; (e) a coding sequence for PCCA selected from SEQ ID NOs: 2-7; (f) an SV40 polyadenylation signal sequence; and (g) an AAV2 3'-ITR sequence.

In certain embodiments, the present disclosure provides an rAAV useful for the treatment of propionic acidemia (PA), said rAAV comprising an AAV8 capsid or AAV9 capsid, and a vector genome packaged therein, said vector genome comprising as operably linked components in 5' to 3' order: (a) an AAV2 5'-ITR sequence; (b) a CMV enhancer sequence; (c) a CBA promoter sequence; (d) an intron sequence at least 90% identical to SEQ ID NO: 1; (e) a coding sequence for PCCB selected from SEQ ID NOs: 8-13; (f) an SV40 polyadenylation signal sequence; and (g) an AAV2 3'-ITR sequence.

In certain embodiments, the present disclosure provides a recombinant nucleic acid construct comprising (a) a promoter sequence; (b) an intron sequence at least 90% identical to SEQ ID NO: 1; and (c) a partial or complete coding sequence for PCCA. In certain embodiments, the present disclosure provides a recombinant nucleic acid construct comprising (a) a promoter sequence; (b) an intron sequence at least 90% identical to SEQ ID NO: 1; and (c) a partial or complete coding sequence for PCCB.

In some aspects, the present disclosure provides the use of an rAAV disclosed herein for the treatment of PA, wherein the rAAV includes an AAV capsid and a vector genome packaged therein. In some embodiments, the rAAV contains a packaged genome comprising as operably linked components in 5' to 3' order: a 5'-ITR, a promoter sequence, an intron sequence at least 90% identical to SEQ ID NO: 1, a partial or complete coding sequence for PCCA or an isoform thereof, or a functional fragment or functional variant thereof, and a 3'-ITR. In an exemplary embodiment, the packaged genome also comprises an enhancer sequence upstream of the promoter sequence and a polyadenylation signal sequence upstream of the 3'-ITR. In one exemplary embodiment, the rAAV contains a packaged genome comprising as operably linked components in 5' to 3' order: an AAV2 5'-ITR sequence, a CMV enhancer, a CBA promoter, an intron sequence at least 90% identical to SEQ ID NO: 1, a coding sequence for PCCA, an SV40 polyadenylation signal sequence, and an AAV2 3'-ITR. In some embodiments, the packaged genome further comprises a consensus Kozak sequence located downstream of the intron sequence. In some embodiments, the coding sequence for PCCA is selected from SEQ ID NOs: 2-7. In some embodiments, the capsid is an AAV8 capsid. In some embodiments, the capsid is an AAV9 capsid.

In some aspects, the present disclosure provides the use of an rAAV disclosed herein for the treatment of PA, wherein the rAAV includes an AAV capsid and a vector genome packaged therein. In some embodiments, the packaged genome comprising as operably linked components in 5' to 3' order comprises: a 5'-ITR, a promoter sequence, an intron sequence at least 90% identical to SEQ ID NO: 1, a partial or complete coding sequence for PCCB or an isoform thereof, or a functional fragment or functional variant thereof, and a 3'-ITR. In an exemplary embodiment, the packaged genome also comprises an enhancer sequence upstream of the promoter sequence and a polyadenylation signal sequence upstream of the 3'-ITR. In one exemplary embodiment, the packaged genome comprising as operably linked components in 5' to 3' order comprises: an AAV2 5'-ITR sequence, a CMV enhancer, a CBA promoter, an intron sequence at least 90% identical to SEQ ID NO: 1, a coding sequence for PCCB, an SV40 polyadenylation signal sequence, and an AAV2 3'-ITR. In some embodiments, the packaged genome further comprises a consensus Kozak sequence located downstream of the intron sequence. In some embodiments, the coding sequence for PCCB is selected from SEQ ID NOs: 8-13. In some embodiments, the capsid is an AAV8 capsid. In some embodiments, the capsid is an AAV9 capsid.

The present disclosure further relates to pharmaceutical compositions comprising an rAAV disclosed herein. In some embodiments, the pharmaceutical composition comprises a pharmaceutically acceptable carrier or excipient. In some embodiments, the pharmaceutical composition is formulated for subcutaneous, intramuscular, intradermal, intraperitoneal, or intravenous administration. In an exemplary embodiment, the pharmaceutical composition is formulated for intravenous administration.

In yet another aspect, the present disclosure provides methods of treating PA in a human subject comprising administering to the human subject a therapeutically effective amount of at least one rAAV disclosed herein. In one embodiment, the present disclosure provides a method of treating PA comprising administering an rAAV that includes an AAV capsid and a vector genome packaged therein, wherein the vector genome comprises a partial or complete coding sequence for PCCA or an isoform thereof, or a functional fragment or functional variant thereof. In another embodiment, the present disclosure provides a method of treating PA comprising administering an rAAV that includes an AAV capsid and a vector genome packaged therein, wherein the vector genome comprises a partial or complete coding sequence for PCCB or an isoform thereof, or a functional fragment or functional variant thereof.

In certain embodiments, the present disclosure provides a method of treating PA comprising administering (1) an rAAV that includes an AAV capsid and a vector genome packaged therein, wherein the vector genome comprises a partial or complete coding sequence for PCCA or an isoform thereof, or a functional fragment or functional variant thereof; and (2) an rAAV that includes an AAV capsid and a vector genome packaged therein, wherein the vector genome comprises a partial or complete coding sequence for PCCB or an isoform thereof, or a functional fragment or functional variant thereof. In some embodiments, the rAAV of (1) and (2) may be administered simultaneously. In some embodiments, the rAAV of (1) and (2) may be administered sequentially. In some embodiments, the rAAV of (1) and (2) may be administered separately.

In certain embodiments, the present disclosure provides methods of treating PA in a human subject comprising administering to a human subject diagnosed with at least one mutation in PCCA a therapeutically effective amount of at least one rAAV disclosed herein. In one embodiment, the present disclosure provides a method of treating PA in a human subject diagnosed with at least one mutation in PCCA comprising administering an rAAV that includes an AAV capsid and a vector genome packaged therein, wherein the vector genome comprises a partial or complete coding sequence for PCCA or an isoform thereof, or a functional fragment or functional variant thereof. In certain embodiments, the mutation in PCCA is selected from Table 1. In some embodiments, the coding sequence for PCCA is selected from SEQ ID NOs: 2-7. In some embodiments, the capsid is an AAV8 capsid. In some embodiments, the capsid is an AAV9 capsid.

In certain embodiments, the present disclosure provides methods of treating PA in a human subject comprising administering to a human subject diagnosed with at least one mutation in PCCB a therapeutically effective amount of at least one rAAV disclosed herein. In one embodiment, the present disclosure provides a method of treating PA in a human subject diagnosed with at least one mutation in PCCB comprising administering an rAAV that includes an AAV capsid and a vector genome packaged therein, wherein the vector genome comprises a partial or complete coding sequence for PCCB or an isoform thereof, or a functional fragment or functional variant thereof. In certain embodiments, the mutation in PCCB is selected from Table 2. In some embodiments, the coding sequence for PCCB is selected from SEQ ID NOs: 8-13. In some embodiments, the capsid is an AAV8 capsid. In some embodiments, the capsid is an AAV9 capsid.

In some embodiments, the rAAV is administered subcutaneously, intramuscularly, intradermally, intraperitoneally, or intravenously. In an exemplary embodiment, the rAAV is administered intravenously. In some embodiments, the rAAV is administered at a dose of about $1\times10^{11}$ to about $1\times10^{14}$ genome copies (GC)/kg. In further embodiments, the rAAV is administered at a dose of about $1\times10^{12}$ to about $1\times10^{13}$ genome copies (GC)/kg. In some embodiments, a single dose of rAAV is administered. In other embodiments, multiple doses of rAAV are administered.

In some aspects, the present disclosure provides host cells comprising a recombinant nucleic acid molecule, an AAV vector, or an rAAV disclosed herein. In specific embodiments, the host cells may be suitable for the propagation of AAV. In certain embodiments, the host cell is selected from a HeLa, Cos-7, HEK293, A549, BHK, Vero, RD, HT-1080, ARPE-19, or MRC-5 cell.

These and other aspects and features of the invention are described in the following sections of the present disclosure.

BRIEF DESCRIPTION OF THE DRAWINGS

The invention can be more completely understood with reference to the following drawings.

FIG. 7A is a line graph showing plasma concentration of 2-methylcitrate (2MC) in a hypomorphic PA mouse model, $Pcca^{-/-}$ (A138T), following rAAV-mediated delivery of a transgene cassette encoding PCCA, comprising the IVS2 intron sequence of SEQ ID NO: 1 (DTC430 (SEQ ID NO: 30)).

FIG. 7B is a line graph showing plasma C3/C2 (propionylcarnitine/acylcarnitine) concentration ratio in a hypomorphic PA mouse model, $Pcca^{-/-}$ (A138T), following administration of PBS ("CONT") or varying doses of rAAV-mediated delivery of a transgene cassette encoding PCCA, comprising the IVS2 intron sequence of SEQ ID NO: 1 (DTC430 (SEQ ID NO: 30)) (time after injection is provided in weeks (W)). "Pre" indicates 2 weeks before injection of rAAV comprising the transgene cassette encoding PCCA. Error bars represent standard error. * denotes $P<0.05$ in comparison to PBS-treated group using Dunnett's test.

DETAILED DESCRIPTION OF THE INVENTION

Figure 1:
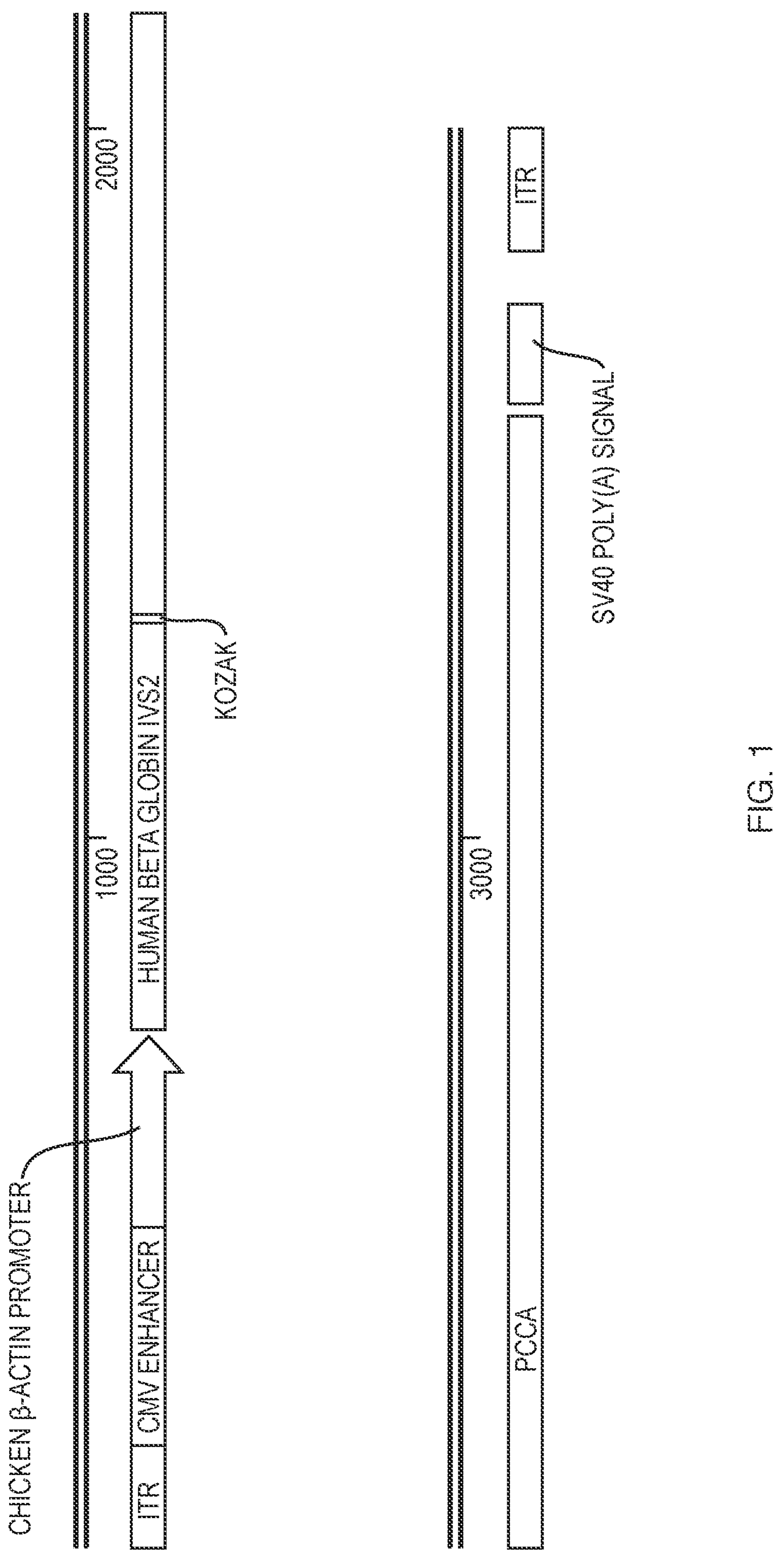
FIG. 1 is an illustrative diagram showing an exemplary packaged vector genome construct comprising PCCA, according to one embodiment. The elements in 5' to 3' order are as follows: 5'-ITR, CMV enhancer, chicken β-actin promoter, an intron sequence of SEQ ID NO: 1 (human β-globin IVS2), consensus Kozak sequence, PCCA coding sequence, SV40 polyadenylation signal, and 3'-ITR.

As described herein, it has been discovered by the present applicant that insertion of a human β-globin IVS2 intron sequence (SEQ ID NO: 1) into a PA gene therapy vector substantially and surprisingly increases transgene expression relative to comparator vectors expressing an alternative intron sequence. Thus, rAAVs of the invention provide unexpectedly high transgene expression, thereby reducing the vector dose required for successful treatment of PA.

As described more fully in the detailed description that follows, this invention provides a range of novel agents and compositions to be used in methods for ameliorating, preventing, or treating PA. More specifically, the invention provides recombinant nucleic acid constructs, vectors, host cells, and recombinant AAV that comprise an intron sequence which is at least 90% identical to SEQ ID NO: 1. In some embodiments, the recombinant nucleic acid constructs, vectors, host cells, and recombinant AAV of the invention may comprise an intron sequence which is at least 90%, 91%, 92%, 93%, 94%, 95%, 96%, 97%, 98%, 99%, 99.5%, or 99.9% identical to SEQ ID NO: 1. In some embodiments, the recombinant nucleic acid constructs, vectors, host cells, and recombinant AAV of the invention may comprise an intron sequence of SEQ ID NO: 1.

Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of the disclosure, the following explanations of specific terms are provided:

Adeno-associated virus (AAV): A small, replication-defective, non-enveloped virus that infects humans and some other primate species. AAV is not known to cause disease and elicits a very mild immune response. Gene therapy vectors that utilize AAV can infect both dividing and quiescent cells and can persist in an extrachromosomal state without integrating into the genome of the host cell. These features make AAV an attractive viral vector for gene therapy. There are currently 12 recognized serotypes of AAV (AAV1-12).

Administration/Administer: To provide or give a subject an agent, such as a therapeutic agent (e.g., a recombinant AAV), by any effective route. Exemplary routes of administration include, but are not limited to, injection (such as subcutaneous, intramuscular, intradermal, intraperitoneal, and intravenous), oral, intraductal, sublingual, rectal, transdermal, intranasal, vaginal and inhalation routes.

Codon-optimized: A "codon-optimized" nucleic acid refers to a nucleic acid sequence that has been altered such that the codons are optimal for expression in a particular system (such as a particular species or group of species). For example, a nucleic acid sequence can be optimized for expression in mammalian cells or in a particular mammalian species (such as human cells). Codon optimization does not alter the amino acid sequence of the encoded protein.

Enhancer: A nucleic acid sequence that increases the rate of transcription by increasing the activity of a promoter.

Intron: A stretch of DNA within a gene that does not contain coding information for a protein. Introns are removed before translation of a messenger RNA.

Inverted terminal repeat (ITR): Symmetrical nucleic acid sequences in the genome of adeno-associated viruses required for efficient replication. ITR sequences are located at each end of the AAV DNA genome. The ITRs serve as the origins of replication for viral DNA synthesis and are essential cis components for generating AAV integrating vectors.

Isolated: An "isolated" biological component (such as a nucleic acid molecule, protein, virus or cell) has been substantially separated or purified away from other biological components in the cell or tissue of the organism, or the organism itself, in which the component naturally occurs, such as other chromosomal and extra-chromosomal DNA and RNA, proteins and cells. Nucleic acid molecules and proteins that have been "isolated" include those purified by standard purification methods. The term also embraces nucleic acid molecules and proteins prepared by recombinant expression in a host cell as well as chemically synthesized nucleic acid molecules and proteins.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein-coding regions, in the same reading frame.

Pharmaceutically acceptable carrier: The pharmaceutically acceptable carriers (vehicles) useful in this disclosure are conventional. *Remington's Pharmaceutical Sciences*, by E. W. Martin, Mack Publishing Co., Easton, Pa., 15th Edition (1975), describes compositions and formulations suitable for pharmaceutical delivery of one or more therapeutic compounds, molecules or agents.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions for example, powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Preventing, treating or ameliorating a disease: "Preventing" a disease (such as PA) refers to inhibiting the full development of a disease. "Treating" refers to a therapeutic intervention that ameliorates a sign or symptom of a disease or pathological condition (such as PA) after it has begun to develop. "Ameliorating" refers to the reduction in the number or severity of signs or symptoms of a disease (such as PA).

Promoter: A region of DNA that directs/initiates transcription of a nucleic acid (e.g., a gene). A promoter includes necessary nucleic acid sequences near the start site of transcription. Many promoter sequences are known to the person skilled in the art and even a combination of different promoter sequences in artificial nucleic acid molecules is possible. As used herein, gene-specific endogenous promoter refers to native promoter element that regulates expression of the endogenous gene of interest. In one embodiment, a PCCA gene-specific endogenous promoter regulates expression of a PCCA gene. In another embodiment, a PCCB gene-specific endogenous promoter regulates expression of a PCCB gene.

Purified: The term "purified" does not require absolute purity; rather, it is intended as a relative term. Thus, for example, a purified peptide, protein, virus, or other active compound is one that is isolated in whole or in part from naturally associated proteins and other contaminants. In certain embodiments, the term "substantially purified" refers to a peptide, protein, virus or other active compound that has been isolated from a cell, cell culture medium, or other crude preparation and subjected to fractionation to remove various components of the initial preparation, such as proteins, cellular debris, and other components.

Recombinant: A recombinant nucleic acid molecule is one that has a sequence that is not naturally occurring or has a sequence that is made by an artificial combination of two otherwise separated segments of sequence. This artificial combination can be accomplished by chemical synthesis or by the artificial manipulation of isolated segments of nucleic acid molecules, such as by genetic engineering techniques.

Similarly, a recombinant virus is a virus comprising sequence (such as genomic sequence) that is non-naturally occurring or made by artificial combination of at least two sequences of different origin. The term "recombinant" also includes nucleic acids, proteins and viruses that have been altered solely by addition, substitution, or deletion of a portion of a natural nucleic acid molecule, protein or virus. As used herein, "recombinant AAV" refers to an AAV particle in which a recombinant nucleic acid molecule such as a recombinant nucleic acid molecule encoding PCCA and/or a recombinant nucleic acid molecule encoding PCCB has been packaged.

Sequence identity: The identity or similarity between two or more nucleic acid sequences, or two or more amino acid sequences, is expressed in terms of the identity or similarity between the sequences. Sequence identity can be measured in terms of percentage identity; the higher the percentage, the more identical the sequences are. Sequence similarity can be measured in terms of percentage similarity (which takes into account conservative amino acid substitutions); the higher the percentage, the more similar the sequences are. Homologs or orthologs of nucleic acid or amino acid sequences possess a relatively high degree of sequence identity/similarity when aligned using standard methods. This homology is more significant when the orthologous proteins or cDNAs are derived from species which are more closely related (such as human and mouse sequences), compared to species more distantly related (such as human and *C. elegans* sequences).

Methods of alignment of sequences for comparison are well known in the art. Various programs and alignment algorithms are described in: Smith & Waterman, *Adv. Appl. Math.* 2:482, 1981; Needleman & Wunsch, *J. Mol. Biol.* 48:443, 1970: Pearson & Lipman, *Proc. Natl. Acad. Sci. USA* 85:2444, 1988; Higgins & Sharp, *Gene,* 73:237-44, 1988; Higgins & Sharp, *CABIOS* 5:151-3, 1989; Corpet et al., *Nuc. Acids Res.* 16:10881-90, 1988; Huang et al. *Computer Appls. in the Biosciences* 8, 155-65, 1992; and Pearson et al., *Meth. Mol. Rio.* 24:307-31, 1994. Altschul et al., *J. Mol. Biol.* 215:403-10, 1990, presents a detailed consideration of sequence alignment methods and homology calculations.

The NCBI Basic Local Alignment Search Tool (BLAST) (Altschul et al., *J. Mol. Biol.* 215:403-10, 1990) is available from several sources, including the National Center for Biological Information (NCBI) and on the internet, for use in connection with the sequence analysis programs blastp, blastn, blastx, tblastn and tblastx. Additional information can be found at the NCBI web site.

Serotype: A group of closely related microorganisms (such as viruses) distinguished by a characteristic set of antigens.

Stuffer sequence: Refers to a sequence of nucleotides contained within a larger nucleic acid molecule (such as a vector) that is typically used to create desired spacing between two nucleic acid features (such as between a promoter and a coding sequence), or to extend a nucleic acid molecule so that it is of a desired length. Stuffer sequences do not contain protein coding information and can be of unknown/synthetic origin and/or unrelated to other nucleic acid sequences within a larger nucleic acid molecule.

Subject: Living multi-cellular vertebrate organisms, a category that includes human and non-human mammals.

Synthetic: Produced by artificial means in a laboratory, for example a synthetic nucleic acid can be chemically synthesized in a laboratory.

Untranslated region (UTR): A typical mRNA contains a 5' untranslated region ("5' UTR") and a 3' untranslated region (3' UTR) upstream and downstream, respectively, of the coding region (see Mignone et al., 2002, *Genome Biol* 3: REVIEWS0004).

Therapeutically effective amount: A quantity of a specified pharmaceutical or therapeutic agent (e.g., a recombinant AAV) sufficient to achieve a desired effect in a subject, or in a cell, being treated with the agent. The effective amount of the agent will be dependent on several factors, including, but not limited to the subject or cells being treated, and the manner of administration of the therapeutic composition.

Vector: A vector is a nucleic acid molecule allowing insertion of foreign nucleic acid without disrupting the ability of the vector to replicate and/or integrate in a host cell. A vector can include nucleic acid sequences that permit it to replicate in a host cell, such as an origin of replication. A vector can also include one or more selectable marker genes and other genetic elements. An expression vector is a vector that contains the necessary regulatory sequences to allow transcription and translation of inserted gene or genes. In some embodiments herein, the vector is an AAV vector.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. "Comprising A or B" means including A, or B, or A and B. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present disclosure, suitable methods and materials are described below. All publications, patent applications, patents, and other references mentioned herein are incorporated by reference in their entirety. In case of conflict, the present specification, including explanations of terms, will control.

In addition, the materials, methods, and examples are illustrative only and not intended to be limiting.

Recombinant Adeno-Associated Virus (rAAV):

This invention provides compositions and methods of their use in gene therapy. More specifically, the present disclosure provides recombinant adeno-associated virus (rAAV) comprising an adeno-associated virus (AAV) capsid, and a vector genome packaged therein useful for the treatment of propionic acidemia (PA).

In one aspect, the present disclosure provides a recombinant adeno-associated virus (rAAV) comprising an AAV capsid, and a vector genome packaged therein, wherein said vector genome comprises: (a) a promoter sequence; (b) an intron sequence at least 90% identical to SEQ ID NO: 1; and (c) a partial or complete coding sequence for PCCA or an isoform thereof, or a functional fragment or functional variant thereof.

In another aspect, the present disclosure provides a recombinant adeno-associated virus (rAAV) comprising an AAV capsid, and a vector genome packaged therein, wherein said vector genome comprises: (a) a promoter sequence; (b) an intron sequence at least 90% identical to SEQ ID NO: 1; and (c) a partial or complete coding sequence for PCCB or an isoform thereof, or a functional fragment or functional variant thereof.

In some embodiments, the packaged genome may further comprise a 5'-ITR, an enhancer, a consensus Kozak sequence, a polyadenylation signal sequence, and a 3'-ITR as described herein. In some embodiments, the packaged genome may further comprise one or more stuffer nucleic acid sequences. In one embodiment, a stuffer nucleic acid sequence is situated between the intron and the partial or complete coding sequence for PCCA or PCCB.

In various embodiments described herein, the rAAV comprises an AAV capsid. The AAV capsid can be from an AAV of serotype 8, 1, 2, 3, 4, 5, 6, 7, 9, 10, 11, 12, rh10, hu37 (i.e., AAV8, AAV1, AAV2, AAV3, AAV4, AAV5, AAV6, AAV7, AAV9, AAV10, AAV11, AAV12, AAVrh10, AAVhu37), as well as any one of the more than 100 variants isolated from human and nonhuman primate tissues. See. e.g., Choi et al., 2005, *Curr Gene Ther.* 5: 299-310, 2005 and Gao et al., 2005, *Curr Gene Ther.* 5: 285-297.

Beyond the aforementioned capsids, also included within the scope of the invention are variant AAV capsids which have been engineered to harbor one or more beneficial therapeutic properties (e.g., improved targeting for select tissues, increased ability to evade the immune response, reduced stimulation of neutralizing antibodies, etc.). Non-limiting examples of such engineered variant capsids are described in U.S. Pat. Nos. 9,506,083, 9,585,971, 9,587,282, 9,611,302, 9,725,485, 9,856,539, 9,909,142, 9,920,097, 10,011,640, 10,081,659, 10,179,176, 10,202,657, 10,214,566, 10,214,785, 10,266,845, 10,294,281, 10,301,648, 10,385,320, and 10,392,632 and in PCT Publication Nos. WO/2017/165859, WO/2018/022905, WO/2018/156654, WO/2018/222503, and WO/2018/226602, the disclosures of which are herein incorporated by reference.

In certain exemplary embodiments, the rAAV administered according to the invention comprises an AAV8 capsid. The AAV8 capsid is a self-assembled AAV capsid composed of multiple AAV8 vp proteins. The AAV8 vp proteins are typically expressed as alternative splice variants encoded by a nucleic acid sequence of SEQ ID NO: 14 or a sequence that is at least 70%, at least 75%, at least 80%, at least 85%, at least 90%, at least 95%, at least 97%, at least 99% identical thereto, which encodes the vp1 amino acid sequence of SEQ ID NO: 15. These splice variants result in proteins of different length of SEQ ID NO: 15. As used herein, an AAV8 variant includes, e.g., those described in WO/2019/168961, WO/2017180854, and U.S. Pat. No. 9,909,142.

In certain exemplary embodiments, the rAAV administered according to the invention comprises an AAV9 capsid. The AAV9 capsid is a self-assembled AAV capsid composed of multiple AAV9 vp proteins. The AAV9 vp proteins are typically expressed as alternative splice variants encoded by a nucleic acid sequence of SEQ ID NO: 16 or a sequence that is at least 70%, at least 75%, at least 80%, at least 85%, at least 90%, at least 95%, at least 97%, at least 99% identical thereto, which encodes the vp1 amino acid sequence of SEQ ID NO: 17. These splice variants result in proteins of different length of SEQ ID NO: 17. As used herein, an AAV9 variant includes, e.g., those described in WO/2016/049230, U.S. Pat. No. 8,927,514, US Patent Publication No. 2015/0344911, and U.S. Pat. No. 8,734,809.

As indicated herein, the rAAV administered according to the invention may comprise, in some embodiments, an AAV8 capsid or AAV9 capsid. However, in other embodiments, another AAV capsid is selected. Tissue specificity is determined by the capsid type. AAV serotypes which transduce a suitable target (e.g., liver, muscle, lung, or CNS) may be selected as sources for capsids of AAV viral vectors including, e.g., AAV1, AAV2, AAV3, AAV4, AAV5, AAV6, AAV6.2, AAV7, AAV8, AAV9, AAVrh10, AAVrh64R1, AAVrh64R2, AAVrh8. See. e.g., US Patent Publication No. 2007/0036760; US Patent Publication No. 2009/0197338; and EP1310571. See also WO 2003/042397 (AAV7 and other simian AAV), U.S. Pat. Nos. 7,282,199 and 7,790,449 (AAV8). In addition, AAV yet to be discovered, or a recombinant AAV based thereon, may be used as a source for the AAV capsid. These documents also describe other AAV which may be selected for generating AAV and are incorporated by reference. In some embodiments, an AAV capsid for use in the viral vector can be generated by mutagenesis (i.e., by insertions, deletions, or substitutions) of one of the aforementioned AAV capsids or its encoding nucleic acid. In some embodiments, the AAV capsid is chimeric, comprising domains from two or three or four or more of the aforementioned AAV capsid proteins. In some embodiments, the AAV capsid is a mosaic of Vp1, Vp2, and Vp3 monomers from two or three different AAVs or recombinant AAVs. In some embodiments, an rAAV composition comprises more than one of the aforementioned capsids.

Promoter:

In various aspects described herein, the rAAV comprises a packaged vector genome which comprises a promoter sequence that helps drive and regulate PCCA or PCCB expression. In exemplary embodiments, the promoter sequence is located between a 5'-ITR sequence and the partial or complete coding sequence for PCCA or PCCB. In some embodiments, the promoter sequence is located downstream of an enhancer sequence. In some embodiments the promoter sequence is located upstream of an intron sequence.

In some embodiments, the promoter is selected from a chicken β-actin (CBA) promoter, a cytomegalovirus (CMV) immediate early gene promoter, a transthyretin (TTR) promoter, a thyroxine binding globulin (TBG) promoter, an alpha-1 anti-trypsin (AIAT) promoter, and a CAG promoter.

In an exemplary embodiment, the promoter is the CBA promoter. In one embodiment, the CBA promoter comprises or consists of SEQ ID NO: 21, or a sequence which is at least 90%, 91%, 92%, 93%, 94%, 95%, 96%, 97%, 98%, or 99% identical thereto.

In addition to a promoter, a packaged genome may contain other appropriate transcription initiation, termination, enhancer sequence, and efficient RNA processing signals. As described in further detail below, such sequences include splicing and polyadenylation (poly A) signals, regulatory elements that enhance expression (i.e., WPRE), sequences that stabilize cytoplasmic mRNA, sequences that enhance translation efficiency (i.e., the Kozak consensus sequence), and sequences that enhance protein stability.

Inverted Terminal Repeats (ITRs):

In some embodiments, the rAAV comprises a packaged vector genome which comprises an AAV ITR sequence, which functions as both the origin of vector DNA replication and the packaging signal of the vector genome, when AAV and adenovirus helper functions are provided in trans. Additionally, the ITRs serve as the target for single-stranded endonucleatic nicking by the large Rep proteins, resolving individual genomes from replication intermediates.

In some embodiments, the 5'-ITR sequence is from AAV2. In some embodiments, the 3'-ITR sequence is from AAV2. In some embodiments, the 5'-ITR sequence and the 3'-ITR sequence are from AAV2. In some embodiments, the 5'-ITR sequence and/or the 3'-ITR sequence is/are from AAV2 and each comprise or consist of SEQ ID NO: 18. In other embodiments, the 5'-ITR sequence and/or the 3'-ITR sequence is/are from a non-AAV2 source.

Enhancer:

In some embodiments, the rAAV contains a packaged vector genome that comprises one or more enhancer sequences. In one embodiment, the enhancer is selected from a cytomegalovirus (CMV) immediate early gene enhancer, a transthyretin enhancer (enTTR), a chicken β-actin (CBA) enhancer, an En34 enhancer, and an ApoE enhancer. In an exemplary embodiment, the enhancer is the CMV enhancer (e.g., CMV immediate early gene enhancer). In one embodiment, the CMV enhancer comprises or consists of SEQ ID NO: 22, or a sequence which is at least 90%, 91%, 92%, 93%, 94%, 95%, 96%, 97%, 98%, 99%, or more than 99% but less than 100% identical thereto.

Kozak Sequence:

In some embodiments, the rAAV contains a packaged vector genome that comprises a consensus Kozak sequence. In some embodiments, the consensus Kozak sequence is located downstream of an intron sequence. In one embodiment, the consensus Kozak sequence is GCCGCC (SEQ ID NO: 24). As will be understood by those skilled in the art, the consensus Kozak sequence is typically located immediately upstream of a coding sequence; in this case, immediately upstream of a partial or complete coding sequence for PCCA or PCCB. As will be appreciated by the skilled artisan, the consensus Kozak sequence can be considered to share an ATG residue corresponding to the start codon of the therapeutic polypeptide, e.g., PCCA or PCCB. For the simplicity of disclosure, the consensus Kozak sequence, as described herein, comprises a six-nucleotide sequence corresponding to the region not shared with the therapeutic polypeptide, e.g., PCCA or PCCB.

Polyadenylation Signal Sequence:

In some embodiments, the rAAV contains a packaged vector genome that comprises a polyadenylation signal sequence. In one embodiment, the polyadenylation signal sequence is selected from an SV40 polyadenylation signal sequence, a bovine growth hormone (BGH) polyadenylation signal sequence, and a rabbit beta globin polyadenylation signal sequence. In an exemplary embodiment, the polyadenylation signal sequence is the SV40 polyadenylation signal sequence. In one embodiment, the SV40 polyadenylation signal sequence comprises or consists of SEQ ID NO: 23, or a sequence which is at least 90%, 91%, 92%, 93%, 94%, 95%, 96%, 97%, 98%, 99%, or more than 99% but less than 100% identical thereto.

PCCA or PCCB Polypeptides:

As described herein, aspects of the invention provide rAAV that include a packaged genome that comprises a promoter sequence, an intron sequence at least 90% identical to SEQ ID NO: 1, and a partial or complete coding sequence for PCCA or an isoform thereof, or a functional fragment or functional variant thereof.

In one embodiment, the partial or complete coding sequence for PCCA or PCCB is a wild-type coding sequence. As used herein, the term "wild-type" refers to a biopolymer (e.g., a polypeptide sequence or polynucleotide sequence) that is the same as the biopolymer (e.g., polypeptide sequence or polynucleotide sequence) that exists in nature.

In an alternative embodiment, the partial or complete coding sequence for PCCA or PCCB is a codon-optimized coding sequence. In one embodiment, the partial or complete coding sequence for PCCA or PCCB is codon-optimized for expression in humans.

In various embodiments described herein, rAAV are provided that contain a packaged genome that comprise a coding sequence for PCCA or PCCB. The polypeptides delivered with the rAAV described herein encompass PCCA and PCCB polypeptides that may be useful in the treatment of mammals, including humans.

In some embodiments, the polypeptide expressed with a rAAV described herein is PCCA (SEQ ID NO: 19; GenBank Accession No. NP_000273.2; 728 amino acids) or a functional fragment, functional variant, or functional isoform thereof. In some embodiments, the polypeptide expressed with a rAAV described herein is PCCA and comprises or consists of SEQ ID NO: 19.

In one embodiment, the PCCA polypeptide is encoded by the wild-type coding sequence shown in SEQ ID NO: 2. In another embodiment, a coding sequence expressing a natural isoform or variant of PCCA may be used, such as those shown in UniProtKB/Swiss-Prot Accession Nos. P05165-1 (SEQ ID NO: 25), P05165-2 (SEQ ID NO: 26), and P05165-3 (SEQ ID NO: 27). In alternative embodiments, the PCCA polypeptide is encoded by a codon-optimized coding sequence. In some embodiments, the PCCA polypeptide is encoded by a codon-optimized coding sequence that is less than 80% identical to the wild-type coding sequence shown in SEQ ID NO: 1. In some exemplary embodiments, the PCCA polypeptide is encoded by a codon-optimized coding sequence selected from SEQ ID NOs: 3-7. In some embodiments, the coding sequence for PCCA may further comprise a stop codon (TGA, TAA, or TAG) at the 3' end.

In some embodiments, the polypeptide expressed with a rAAV described herein is PCCB (SEQ ID NO: 20; GenBank Accession No. NP_000523.2; 539 amino acids) or a functional fragment, functional variant, or functional isoform thereof. In some embodiments, the polypeptide expressed with a rAAV described herein is PCCB and comprises or consists of SEQ ID NO: 20.

In one embodiment, the PCCB polypeptide is encoded by the wild-type coding sequence shown in SEQ ID NO: 8. In another embodiment, a coding sequence expressing a natural isoform or variant of PCCB may be used, such as those shown in UniProtKB/Swiss-Prot Accession Nos. P05166-1 (SEQ ID NO: 28) and P05166-2 (SEQ ID NO: 29). In alternative embodiments, the PCCB polypeptide is encoded by a codon-optimized coding sequence. In some embodiments, the PCCB polypeptide is encoded by a codon-optimized coding sequence that is less than 80% identical to the wild-type coding sequence shown in SEQ ID NO: 8. In some exemplary embodiments, the PCCB polypeptide is encoded by a codon-optimized coding sequence selected from SEQ ID NOs: 9-13. In some embodiments, the coding sequence for PCCB may further comprise a stop codon (TGA, TAA, or TAG) at the 3' end.

In various aspects, the invention may be used to deliver fragments, variants, isoforms, or fusions of the PCCA or PCCB polypeptides described herein.

In some embodiments, the invention may be used to deliver fragments of the PCCA or PCCB polypeptides, which comprise at least 50, 100, 150, 200, 250, 300, 350, 400, 450, 500, 550, or 600 amino acid residues and retain one or more activities associated with the full-length polypeptide (e.g., catalytic activity in the case of an enzyme). Such fragments may be obtained by recombinant techniques that are routine and well-known in the art. Moreover, such fragments may be tested for catalytic activity by routine in vitro assays known to the skilled artisan. For instance, propionyl-CoA carboxylase (PCC) activity can be assayed by (1) diluting the polypeptide in 10 mM phosphate buffer (pH 7.0) containing 1 mM 2-mercaptoethanol and 0.1 mg/ml of bovine serum albumin, (2) taking the standard reaction mixture containing 50 mM Tris-HCl pH 8.0, 5 mM glutathione, 2 mM ATP, 100 mM KCl, 10 mM $MgCl_2$, 10 mM [$^{14}$C]-bicarbonate (specific activity 12.4 mCi/mmol), 3 mM propionyl-CoA, and incubating enzyme at 37 degrees C. for 15 min, (3) stopping the reaction by addition of 10% trichloroacetic acid, (4) centrifuging at 200×g, (5) drying an aliquot under a heat lamp, (6) dissolving in water, and (7) counting in AQUASOL®, wherein one unit of enzyme activity is defined as that amount of enzyme catalyzing the fixation of 1 pmol of bicarbonate/min at 37 degrees C. See Kalousek et al., 1980, *J Biol Chem* 255(1): 60-65 and Hsia et al., 1973 *J. Pediatr.* 83: 625-628 for a description of PCC activity assays. The invention further includes nucleic acid molecules which encode the above-described polypeptide fragments.

In some embodiments, the invention may be used to deliver variants of the PCCA or PCCB polypeptides. In some embodiments, the variant polypeptides may be at least 80% (e.g., 80%, 81%, 82%, 83%, 84%, 85%, 86%, 87%, 88%, 89%, 90%, 91%, 92%, 93%, 94%, 95%, 96%, 97%, 98%, 99%, 99.5%, 99.6%, 99.7%, 99.8%, 99.9%, or 100%) identical to the wild-type therapeutic polypeptide, e.g., a wild-type PCCA polypeptide of SEQ ID NO: 19 or a wild-type PCCB polypeptide of SEQ ID NO: 20. In some embodiments, the variant therapeutic polypeptides may have at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 different residues as compared to the respective wild-type polypeptide. Such variants may be obtained by recombinant techniques that are routine and well-known in the art. Moreover, such variants may be tested for catalytic activity by routine in vitro assays known to the skilled artisan. See, e.g., Kalousek et al., 1980, *J Biol Chem* 255(1): 60-65 and Hsia et al., 1973 *J. Pediatr.* 83: 625-628 for a description of propionyl-CoA carboxylase activity assays. The invention further includes nucleic acid molecules which encode the above described therapeutic polypeptide variants.

Codon-Optimized Sequences:

In some aspects, the present disclosure provides rAAV comprising a packaged genome that comprises a codon-optimized nucleic acid sequence encoding PCCA. In one embodiment, the codon-optimized nucleic acid sequence encoding PCCA is less than 80% identical to the wild-type coding sequence shown in SEQ ID NO: 2. In some embodiments, the codon-optimized nucleic acid sequence encoding PCCA is at least 80% (e.g., 80%, 81%, 82%, 83%, 84%, 85%, 86%, 87%, 88%, 89%, 90%, 91%, 92%, 93%, 94%, 95%, 96%, 97%, 98%, 99%, 99.5%, 99.6%, 99.7%, 99.8%, 99.9%, or 100%) identical to a sequence selected from SEQ ID NOs: 3-7. In some embodiments, the codon-optimized nucleic acid sequence encoding PCCA is 100% identical to a sequence selected from SEQ ID NOs: 3-7. In some embodiments, the present disclosure provides nucleic acid sequences which are less than 80% identical to the wild-type coding sequence shown in SEQ ID NO: 2 and are at least 80%, 85%, 90%, 91%, 92%, 93%, 94%, 95%, 96%, 97%, 98%, 99% or more identical to a sequence selected from SEQ ID NOs: 3-7. In exemplary embodiments, the present disclosure provides a nucleic acid sequence encoding PCCA selected from SEQ ID NOs: 3-7. Further provided are fragments of the nucleic acid sequences shown in SEQ ID NOs: 3-7 which each encode a polypeptide having functional PCCA activity. In some embodiments, the nucleic acid sequence encoding PCCA may further comprise a stop codon (TGA, TAA, or TAG) at the 3' end.

In some aspects, the present disclosure provides rAAV comprising a packaged genome that comprises a codon-optimized nucleic acid sequence encoding PCCB. In one embodiment, the codon-optimized nucleic acid sequence encoding PCCB is less than 80% identical to the wild-type coding sequence shown in SEQ ID NO: 8. In some embodiments, the codon-optimized nucleic acid sequence encoding PCCB is at least 80% (e.g., 80%, 81%, 82%, 83%, 84%, 85%, 86%, 87%, 88%, 89%, 90%, 91%, 92%, 93%, 94%, 95%, 96%, 97%, 98%, 99%, 99.5%, 99.6%, 99.7%, 99.8%, 99.9%, or 100%) identical to a sequence selected from SEQ ID NOs: 9-13. In some embodiments, the codon-optimized nucleic acid sequence encoding PCCB is 100% identical to a sequence selected from SEQ ID NOs: 9-13. In some embodiments, the present disclosure provides nucleic acid sequences which are less than 80% identical to the wild-type coding sequence shown in SEQ ID NO: 8 and are at least 80%, 85%, 90%, 91%, 92%, 93%, 94%, 95%, 96%, 97%, 98%, 99% or more identical to a sequence selected from SEQ ID NOs: 9-13. In exemplary embodiments, the present disclosure provides a nucleic acid sequence encoding PCCB selected from SEQ ID NOs: 9-13. Further provided are fragments of the nucleic acid sequences shown in SEQ ID NOs: 9-13 which each encode a polypeptide having functional PCCB activity. In some embodiments, the nucleic acid sequence encoding PCCB may further comprise a stop codon (TGA, TAA, or TAG) at the 3' end.

Recombinant Nucleic Acid Constructs:

In another aspect, the present disclosure provides recombinant nucleic acid constructs comprising a promoter sequence, an intron sequence at least 90% identical to SEQ ID NO: 1, and a partial or complete coding sequence for PCCA or an isoform thereof, or a functional fragment or functional variant thereof. In some embodiments, the recombinant nucleic acid construct also comprises one or more elements selected from a 5'-ITR, an enhancer sequence, a polyadenylation signal sequence, and a 3'-ITR. In one embodiment, the recombinant nucleic acid construct comprises a 5'-ITR, an enhancer sequence, a promoter sequence, an intron sequence at least 90% identical to SEQ ID NO: 1, a partial or complete coding sequence for PCCA or an isoform thereof, or a functional fragment or functional variant thereof, a polyadenylation signal sequence, and a 3'-ITR. In a further embodiment, the recombinant nucleic acid construct comprises an AAV2 5'-ITR, a CMV enhancer, a CBA promoter, an intron sequence at least 90% identical to SEQ ID NO: 1, a coding sequence for PCCA, an SV40 polyadenylation signal sequence, and an AAV2 3'-ITR. In some embodiments, the recombinant nucleic acid construct further comprises a consensus Kozak sequence located downstream of the intron sequence. In some embodiments, the intron sequence comprises or consists of SEQ ID NO: 1. In some embodiments, the coding sequence for PCCA is selected from SEQ ID NOs: 2-7.

In some embodiments, the present disclosure provides is a recombinant nucleic acid construct which comprises a sequence which is at least 90% identical to SEQ ID NO: 30. In some embodiments, the recombinant nucleic acid construct comprises a sequence which is at least 80%, 85%, 90%, 91%, 92%, 93%, 94%, 95%, 96%, 97%, 98%, 99%, 99.5%, or 99.9% identical to SEQ ID NO: 30. In some embodiments, the recombinant nucleic acid construct consists of a sequence which is at least 80%, 85%, 90%, 91%, 92%, 93%, 94%, 95%, 96%, 97%, 98%, 99%, 99.5%, or 99.9% identical to SEQ ID NO: 30. In some embodiments, the recombinant nucleic acid construct comprises SEQ ID NO: 30. In some embodiments, the recombinant nucleic acid construct consists of SEQ ID NO: 30.

In another aspect, the present disclosure provides recombinant nucleic acid constructs comprising a promoter sequence, an intron sequence at least 90% identical to SEQ ID NO: 1, and a partial or complete coding sequence for PCCB or an isoform thereof, or a functional fragment or functional variant thereof. In some embodiments, the recombinant nucleic acid construct also comprises one or more elements selected from a 5'-ITR, an enhancer sequence, a polyadenylation signal sequence, and a 3'-ITR. In one embodiment, the recombinant nucleic acid construct comprises a 5'-ITR, an enhancer sequence, a promoter sequence, an intron sequence at least 90% identical to SEQ ID NO: 1, a partial or complete coding sequence for PCCB or an isoform thereof, or a functional fragment or functional variant thereof, a polyadenylation signal sequence, and a 3'-ITR. In a further embodiment, the recombinant nucleic acid construct comprises an AAV2 5'-ITR, a CMV enhancer, a CBA promoter, an intron sequence at least 90% identical to SEQ ID NO: 1, a coding sequence for PCCB, an SV40 polyadenylation signal sequence, and an AAV2 3'-ITR. In some embodiments, the recombinant nucleic acid construct further comprises a consensus Kozak sequence located downstream of the intron sequence. In some embodiments, the intron sequence comprises or consists of SEQ ID NO: 1. In some embodiments, the coding sequence for PCCB is selected from SEQ ID NOs: 8-13.

In some embodiments, the present disclosure provides is a recombinant nucleic acid construct which comprises a sequence which is at least 90% identical to SEQ ID NO: 31. In some embodiments, the recombinant nucleic acid construct comprises a sequence which is at least 80%, 85%, 90%, 91%, 92%, 93%, 94%, 95%, 96%, 97%, 98%, 99%, 99.5%, or 99.9% identical to SEQ ID NO: 31. In some embodiments, the recombinant nucleic acid construct consists of a sequence which is at least 80%, 85%, 90%, 91%, 92%, 93%, 94%, 95%, 96%, 97%, 98%, 99%, 99.5%, or 99.9% identical to SEQ ID NO: 31. In some embodiments, the recombinant nucleic acid construct comprises SEQ ID NO: 31. In some embodiments, the recombinant nucleic acid construct consists of SEQ ID NO: 31.

Vectors:

In another aspect, the present disclosure provides a vector comprising a recombinant nucleic acid construct of the invention. In one embodiment, the vector comprises a recombinant nucleic acid construct comprising a 5'-ITR, a promoter sequence, an intron sequence at least 90% identical to SEQ ID NO: 1, a partial or complete coding sequence for PCCA or an isoform thereof, or a functional fragment or functional variant thereof, and a 3'-ITR. In another embodiment, the vector comprises a recombinant nucleic acid construct comprising a 5'-ITR, a promoter sequence, an intron sequence at least 90% identical to SEQ ID NO: 1, a partial or complete coding sequence for PCCB or an isoform thereof, or a functional fragment or functional variant thereof, and a 3'-ITR.

In some embodiments according to this aspect, the vector is selected from a plasmid, a cosmid, a phagemid, an episome, a non-viral delivery vehicle (e.g., a lipid nanoparticle), and a virus. In an exemplary embodiment, the vector is a plasmid.

The selected vector may be delivered to a host cell by any suitable method, including transfection, electroporation, liposome-based delivery, and membrane fusion techniques. In an exemplary embodiment, the vector is delivered to a host cell via transfection. Standard DNA transfection techniques may be used to deliver a vector to a host cell. See. e.g., Sambrook et al., 2000, *Molecular Cloning: A Laboratory Manual,* 3d. Ed., Cold Spring Harbor Press, Plainview, NY.

In some embodiments, the vector, e.g., a plasmid, may further comprise one or more nucleic acid sequences selected from an AAV Rep coding sequence, an AAV Cap coding sequence, and a coding sequence for a selectable marker.

Host Cells:

In another aspect, the present disclosure provides host cells comprising a recombinant nucleic acid molecule of the invention, a vector of the invention, or an rAAV of the invention.

In some embodiments, the host cells may be suitable for the propagation of AAV. A vast range of host cells can be used for the production of AAV, such as bacteria, yeast, insect, mammalian cells, etc. In some embodiments, the host cell can be a cell (or a cell line) appropriate for production of recombinant AAV (rAAV), for example, a HeLa, Cos-7, HEK293, A549, BHK, Vero, RD, HT-1080, ARPE-19, or MRC-5 cell.

The recombinant nucleic acid molecules or vectors can be delivered into the host cell culture using any suitable method known in the art. In some embodiments, a stable host cell line that has the recombinant nucleic acid molecule or vector inserted into its genome is generated. In some embodiments, a stable host cell line is generated, which contains an rAAV vector described herein. After transfection of the rAAV vector to the host culture, integration of the rAAV into the host genome can be assayed by various methods, such as antibiotic selection, fluorescence-activated cell sorting, southern blot, PCR based detection, fluorescence in situ hybridization as described by Nakai et al, Nature Genetics (2003) 34, 297-302; Philpott et al, Journal of Virology (2002) 76(11):5411-5421, and Howden et al, J Gene Med 2008; 10:42-50. Furthermore, a stable cell line can be established according to protocols well known in the art, such as those described in Clark, Kidney International Vol 61 (2002):S9-S15, and Yuan et al, Human Gene Therapy 2011 May; 22(5):613-24.

Recombinant AAV for Gene Therapy:

In another aspect, the present disclosure provides the use of an rAAV disclosed herein for the treatment of propionic acidemia (PA), wherein the rAAV includes an AAV capsid and a vector genome packaged therein. In some embodiments, the rAAV contains a packaged genome comprising as operably linked components in 5' to 3' order: a promoter sequence, an intron sequence at least 90% identical to SEQ ID NO: 1, and a partial or complete coding sequence for PCCA or an isoform thereof, or a functional fragment or functional variant thereof. In an exemplary embodiment, the packaged genome also comprises a 5'-ITR, an enhancer sequence upstream of the promoter sequence, a polyadenylation sequence upstream of a 3'-ITR, and a 3'-ITR. Thus, in another exemplary embodiment, the rAAV contains a packaged genome comprising as operably linked components in 5' to 3' order: a 5'-ITR, an enhancer sequence, a promoter sequence, an intron sequence at least 90% identical to SEQ ID NO: 1, a partial or complete coding sequence for PCCA or an isoform thereof, or a functional fragment or functional variant thereof, a polyadenylation signal sequence, and a 3'-ITR. In a further exemplary embodiment, the rAAV contains a packaged genome comprising as operably linked components in 5' to 3' order: an AAV2 5'-ITR sequence, a CMV enhancer, a CBA promoter, an intron sequence at least 90% identical to SEQ ID NO: 1, a coding sequence for PCCA, an SV40 polyadenylation signal sequence, and an AAV2 3'-ITR. In some embodiments, the packaged genome further comprises a consensus Kozak sequence located downstream of the intron sequence. In some embodiments, the intron sequence comprises or consists of SEQ ID NO: 1. In some embodiments, the coding sequence for PCCA is selected from SEQ ID NOs: 2-7. In some embodiments, the capsid is an AAV8 or AAV9 capsid.

An illustrative diagram showing an exemplary packaged vector genome construct for the expression of PCCA is provided in FIG. 1, which shows in 5' to 3' order: a 5'-ITR, a CMV enhancer, a CBA promoter, an intron sequence of SEQ ID NO: 1, a consensus Kozak sequence, a PCCA coding sequence, an SV40 polyadenylation signal sequence, and a 3'-ITR.

In another aspect, the present disclosure provides the use of an rAAV disclosed herein for the treatment of propionic acidemia (PA), wherein the rAAV includes an AAV capsid and a vector genome packaged therein. In some embodiments, the rAAV contains a packaged genome comprising as operably linked components in 5' to 3' order: a promoter sequence, an intron sequence at least 90% identical to SEQ ID NO: 1, and a partial or complete coding sequence for PCCB or an isoform thereof, or a functional fragment or functional variant thereof. In an exemplary embodiment, the packaged genome also comprises a 5'-ITR, an enhancer sequence upstream of the promoter sequence, a polyadenylation sequence upstream of a 3'-ITR, and a 3'-ITR. Thus, in another exemplary embodiment, the rAAV contains a packaged genome comprising as operably linked components in 5' to 3' order: a 5'-ITR, an enhancer sequence, a promoter sequence, an intron sequence at least 90% identical to SEQ ID NO: 1, a partial or complete coding sequence for PCCB or an isoform thereof, or a functional fragment or functional variant thereof, a polyadenylation signal sequence, and a 3'-ITR. In a further exemplary embodiment, the rAAV contains a packaged genome comprising as operably linked components in 5' to 3' order: an AAV2 5'-ITR sequence, a CMV enhancer, a CBA promoter, an intron sequence at least 90% identical to SEQ ID NO: 1, a coding sequence for PCCB, an SV40 polyadenylation signal sequence, and an AAV2 3'-ITR. In some embodiments, the packaged genome further comprises a consensus Kozak sequence located downstream of the intron sequence. In some embodiments, the intron sequence comprises or consists of SEQ ID NO: 1. In some embodiments, the coding sequence for PCCB is selected from SEQ ID NOs: 8-13. In some embodiments, the capsid is an AAV8 or AAV9 capsid.

Figure 2:
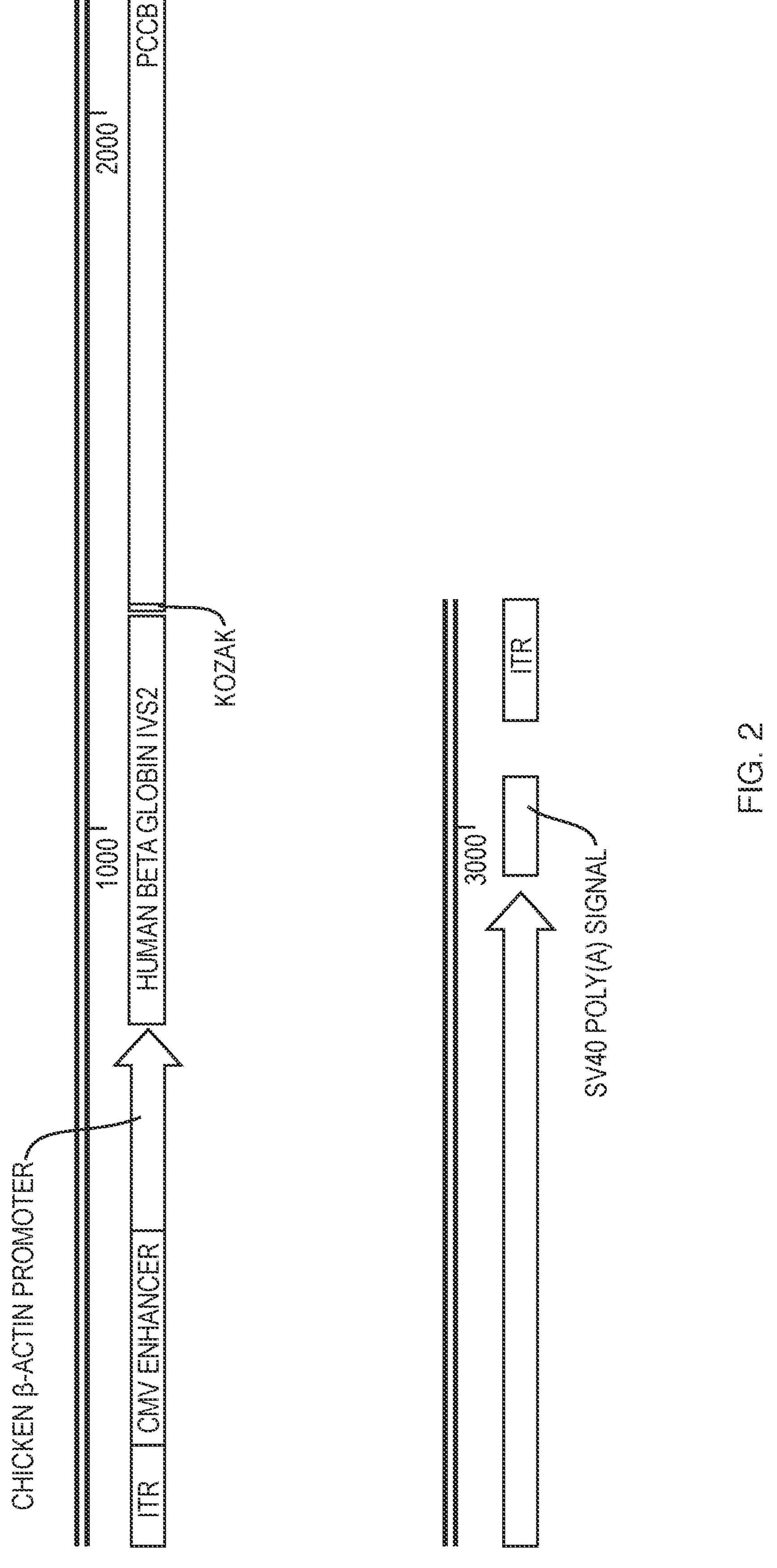
FIG. 2 is an illustrative diagram showing an exemplary packaged vector genome construct comprising PCCB, according to one embodiment. The elements in 5' to 3' order are as follows: 5'-ITR, CMV enhancer, chicken β-actin promoter, an intron sequence of SEQ ID NO: 1 (human β-globin IVS2), consensus Kozak sequence, PCCB coding sequence, SV40 polyadenylation signal, and 3'-ITR.

An illustrative diagram showing an exemplary packaged vector genome construct for the expression of PCCA is provided in FIG. 2, which shows in 5' to 3' order: a 5'-ITR, a CMV enhancer, a CBA promoter, an intron sequence of SEQ ID NO: 1, a consensus Kozak sequence, a PCCB coding sequence, an SV40 polyadenylation signal sequence, and a 3'-ITR.

Protein Localization:

Propionyl-CoA carboxylase is a multimeric protein that is localized to the mitochondrial matrix (see Browner et al., (1989). *Journal of Biological Chemistry.* 264:12680-5). Therefore, it is imperative that the gene therapy vectors delivering PCCA and/or PCCB gene(s) are capable of encoding for proteins that are functional and localized in mitochondria. In one aspect, one or more rAAV disclosed herein are capable of delivering genes that encode for PCCA and/or PCCB protein(s) that localize in the mitochondria.

Pharmaceutical Compositions:

In another aspect, the present disclosure provides a pharmaceutical composition that comprises an rAAV of the invention (e.g., an rAAV for the delivery of PCCA or PCCB) and a pharmaceutically acceptable carrier or excipient. In some embodiments, the pharmaceutical composition comprising an rAAV of the invention (e.g., an rAAV for the delivery of PCCA or PCCB) is formulated for subcutaneous, intramuscular, intradermal, intraperitoneal, or intravenous administration. In an exemplary embodiment, the pharmaceutical composition is formulated for intravenous administration.

In some embodiments, the rAAV is formulated in a buffer/carrier suitable for infusion in human subjects. The buffer/carrier should include a component that prevents the rAAV from sticking to the infusion tubing but does not interfere with the rAAV binding activity in vivo. Various suitable solutions may include one or more of: a buffering saline, a surfactant, and a physiologically compatible salt or mixture of salts adjusted to an ionic strength equivalent to about 100 mM sodium chloride (NaCl) to about 250 mM sodium chloride, or a physiologically compatible salt adjusted to an equivalent ionic concentration. The pH may be in the range of 6.5 to 8.5, or 7 to 8.5, or 7.5 to 8. A suitable surfactant, or combination of surfactants, may be selected from among Poloxamers, i.e., nonionic triblock copolymers composed of a central hydrophobic chain of polyoxypropylene 10 (poly(propylene oxide)) flanked by two hydrophilic chains of polyoxyethylene (poly(ethylene oxide)), SOLUTOL™ HS 15 (Macrogol-15 Hydroxystearate), LABRASOL® (Polyoxy caprYllic glyceride), polyoxy 10 oleyl ether, TWEEN® (polyoxyethylene sorbitan fatty acid esters), ethanol and polyethylene glycol.

In an exemplary embodiment, the rAAV is formulated in a solution comprising NaCl (e.g., 200 mM NaCl), $MgCl_2$ (e.g., 1 mM $MgCl_2$), Tris (e.g., 20 mM Tris), pH 8.0, and poloxamer 188 (e.g., 0.005% or 0.01% poloxamer 188).

Methods of Treating Propionic Acidemia:

In another aspect, the present disclosure provides methods of treating PA in a human subject comprising administering to the human subject a therapeutically effective amount of at least one rAAV disclosed herein.

In one embodiment, the present disclosure provides a method of treating PA comprising administering an rAAV that includes an AAV capsid and a vector genome packaged therein, wherein the vector genome comprises a promoter sequence, at least 90% identical to SEQ ID NO: 1, and a partial or complete coding sequence for PCCA or an isoform thereof, or a functional fragment or functional variant thereof.

In another embodiment, the present disclosure provides a method of treating PA comprising administering an rAAV that includes an AAV capsid and a vector genome packaged therein, wherein the vector genome comprises a promoter sequence, at least 90% identical to SEQ ID NO: 1, and a partial or complete coding sequence for PCCB or an isoform thereof, or a functional fragment or functional variant thereof.

In yet another embodiment, the present disclosure provides a method of treating PA comprising administering (1) an rAAV that includes an AAV capsid and a vector genome packaged therein, wherein said vector genome comprises a promoter sequence, at least 90% identical to SEQ ID NO: 1, and a partial or complete coding sequence for PCCA or an isoform thereof, or a functional fragment or functional variant thereof; and (2) an rAAV that includes an AAV capsid and a vector genome packaged therein, wherein said vector genome comprises a promoter sequence, at least 90% identical to SEQ ID NO: 1, and a partial or complete coding sequence for PCCB or an isoform thereof, or a functional fragment or functional variant thereof. In some embodiments, the rAAV of (1) and (2) may be administered simultaneously. In some embodiments, the rAAV of (1) and (2) may be administered sequentially. In some embodiments, the rAAV of (1) and (2) may be administered separately.

In another aspect, the present disclosure provides methods of treating PA in a human subject comprising administering to a human subject diagnosed with at least one mutation in PCCA a therapeutically effective amount of at least one rAAV disclosed herein. In one embodiment, the present disclosure provides a method of treating PA in a human subject diagnosed with at least one mutation in PCCA comprising administering an rAAV that includes an AAV capsid and a vector genome packaged therein, wherein said vector genome comprises a promoter sequence, at least 90% identical to SEQ ID NO: 1, and a partial or complete coding sequence for PCCA or an isoform thereof, or a functional fragment or functional variant thereof. In certain embodiments, the mutation in PCCA is selected from Table 1. In some embodiments, the coding sequence for PCCA is selected from SEQ ID NOs: 2-7. In some embodiments, the capsid is an AAV8 or AAV9 capsid.

In another aspect, the present disclosure provides methods of treating PA in a human subject comprising administering to a human subject diagnosed with at least one mutation in PCCB a therapeutically effective amount of at least one rAAV disclosed herein. In one embodiment, the present disclosure provides a method of treating PA in a human subject diagnosed with at least one mutation in PCCB comprising administering an rAAV that includes an AAV capsid and a vector genome packaged therein, wherein said vector genome comprises a promoter sequence, at least 90% identical to SEQ ID NO: 1, and a partial or complete coding sequence for PCCB or an isoform thereof, or a functional fragment or functional variant thereof. In certain embodiments, the mutation in PCCB is selected from Table 2. In some embodiments, the coding sequence for PCCB is selected from SEQ ID NOs: 8-13. In some embodiments, the capsid is an AAV8 or AAV9 capsid.

A review article describing PA-causing mutations in PCCA and PCCB is provided in Ugarte et al., 1999, *Hum. Mutat.* 14(4): 275-282.

In PA caused by a mutated PCCA gene, the following mutations and polymorphisms in the PCCA gene have been identified:

TABLE 1

| PCCA Gene Mutations and Polymorphisms: | |
|---|---|
| Missense Mutations: | 148 G→C, 154 C→T, 337 G→A, 416 T→C, 611 T→C, 815 A→G, 1028 A→G, 1043 T→A, 1061 G→T 1121 G→A, 1193 C→T, 1601 G→T, 1816 G→C, 1927 G→T |
| Nonsense Mutations: | 862 C→T, 1610 C→G |
| Small Deletions: | 700 del5, 1115del4, 2058del3 |
| Splicing Mutations: | 1645IVS + 1G→A, 1671IVS + 5G→C, 1771IV2-2del9, 1824IVS + 3del4, 1824IVS + 3insCT |
| Polymorphisms: | 552A→G, 1348A→G |

In PA caused by a mutated PCCB gene, the following mutations and polymorphisms in the PCCB gene have been identified:

TABLE 2

| PCCB Gene Mutations and Polymorphisms: | |
|---|---|
| Missense Mutations: | 49 C→A, 131 G→C, 318 C→A, 391 G→C, 493 C→T, 502 G→A, 593 G→A, 605 T→A, 683 C→T 1228 C→T, 1283 C→T, 1325 T→C, 1490 C→T, 1534 C→T, 1556 T→C, 1606 A→G, |
| Nonsense Mutations: | 1495 C→T, 1593 G→A |
| Insertions and Deletions; | 418ins12, 790insG, 1170insT, 1218del14ins12, 1222del3, 1298insA |
| Splicing Mutations: | IVS1 + 3G→C, IVS4 + 3del4, IVS10-11del6, IVS12 + 3del8, IVS13 + 1G→T |

Any suitable method or route can be used to administer an rAAV or an rAAV-containing composition described herein. Routes of administration include, for example, systemic, oral, inhalation, intranasal, intratracheal, intraarterial, intraocular, intravenous, intramuscular, subcutaneous, intradermal, and other parental routes of administration. In some embodiments, the rAAV, a composition comprising an rAAV, or a composition comprising multiple rAAVs (e.g., one rAAV expressing PCCA and a second rAAV expressing PCCB) are administered intravenously.

The specific dose administered can be a uniform dose for each patient, for example, $1.0\times10^{11}$-$1.0\times10^{14}$ genome copies (GC) of virus per patient. Alternatively, a patient's dose can be tailored to the approximate body weight or surface area of the patient. Other factors in determining the appropriate dosage can include the disease or condition to be treated or prevented, the severity of the disease, the route of administration, and the age, sex and medical condition of the patient. Further refinement of the calculations necessary to determine the appropriate dosage for treatment is routinely made by those skilled in the art, especially in light of the dosage information and assays disclosed herein. The dosage can also be determined through the use of known assays for determining dosages used in conjunction with appropriate dose-response data. An individual patient's dosage can also be adjusted as the progress of the disease is monitored.

In some embodiments, the rAAV is administered at a dose of, e.g., about $1.0\times10^{11}$ genome copies per kilogram of patient body weight (GC/kg) to about $1\times10^{14}$ GC/kg, about $5\times10^{11}$ genome copies per kilogram of patient body weight (GC/kg) to about $5\times10^{13}$ GC/kg, or about $1\times10^{12}$ to about $1\times10^{13}$ GC/kg, as measured by qPCR or digital droplet PCR (ddPCR). In some embodiments, the rAAV is administered at a dose of about $1\times10^{12}$ to about $1\times10^{13}$ genome copies (GC)/kg. In some embodiments, the rAAV is administered at a dose of about $1.1\times10^{11}$, about $1.3\times10^{11}$, about $1.6\times10^{11}$, about $1.9\times10^{1}$, about $2\times10^{11}$, about $2.5\times10^{11}$, about $3.0\times10^{11}$, about $3.5\times10^{11}$, about $4.0\times10^{11}$, about $4.5\times10^{11}$, about $5.0\times10^{11}$, about $5.5\times10^{1}$, about $6.0\times10^{11}$, about $6.5\times10^{11}$, about $7.0\times10^{11}$, about $7.5\times10^{11}$, about $8.0\times10^{11}$, about $8.5\times10^{11}$, about $9.0\times10^{11}$, about $9.5\times10^{11}$, about $1.0\times10^{12}$, about $1.5\times10^{12}$, about $2.0\times10^{12}$, about $2.5\times10^{12}$, about $3.0\times10^{12}$, about $3.5\times10^{12}$, about $4.0\times10^{12}$, about $4.5\times10^{12}$, about $5.0\times10^{12}$, about $5.5\times10^{12}$, about $6.0\times10^{12}$, about $6.5\times10^{12}$, about $7.0\times10^{12}$, about $7.5\times10^{12}$, about $8.0\times10^{12}$, about $8.5\times10^{12}$, about $9.0\times10^{12}$, about $9.5\times10^{12}$, about $1.0\times10^{13}$, about $1.5\times10^{13}$, about $2.0\times10^{13}$, about $2.5\times10^{13}$, about $3.0\times10^{13}$, about $3.5\times10^{13}$, about $4.0\times10^{13}$, about $4.5\times10^{13}$, about $5.0\times10^{13}$, about $5.5\times10^{13}$, about $6.0\times10^{13}$, about $6.5\times10^{13}$, about $7.0\times10^{13}$, about $7.5\times10^{13}$, about $8.0\times10^{13}$, about $8.5\times10^{13}$, about $9.0\times10^{13}$, about $9.5\times10^{13}$ genome copies (GC)/kg. The rAAV can be administered in a single dose, or in multiple doses (such as 2, 3, 4, 5, 6, 7, 8, 9, 10 or more doses) as needed for the desired therapeutic results.

Doses may be given once or more times weekly, monthly or yearly, or even once every 2 to 20 years. For example, each dose may be given at minimum of 1 week apart, 2 weeks apart, 3 weeks apart, a months apart, 3 months apart, 6 months apart, or 1 year apart. Persons of ordinary skill in the art can easily estimate repetition rates for dosing based on measured residence times and concentrations of the targetable construct or complex in bodily fluids or tissues.

Throughout the description, where compositions are described as having, including, or comprising specific components, or where processes and methods are described as having, including, or comprising specific steps, it is contemplated that, additionally, there are compositions of the present invention that consist essentially of, or consist of, the recited components, and that there are processes and methods according to the present invention that consist essentially of, or consist of, the recited processing steps.

In the present disclosure, where an element or component is said to be included in and/or selected from a list of recited elements or components, it should be understood that the element or component can be any one of the recited elements or components, or the element or component can be selected from a group consisting of two or more of the recited elements or components.

Further, it should be understood that elements and/or features of a composition or a method described herein can be combined in a variety of ways without departing from the spirit and scope of the present invention, whether explicit or implicit herein. For example, where reference is made to a particular compound, that compound can be used in various embodiments of compositions of the present invention and/or in methods of the present invention, unless otherwise understood from the context. In other words, within the present disclosure, embodiments have been described and depicted in a way that enables a clear and concise disclosure to be written and drawn, but it is intended and will be appreciated that embodiments may be variously combined or separated without parting from the present teachings and invention(s). For example, it will be appreciated that all features described and depicted herein can be applicable to all aspects of the invention(s) described and depicted herein.

It should be understood that the expression "at least one of" includes individually each of the recited objects after the expression and the various combinations of two or more of the recited objects unless otherwise understood from the context and use. The expression "and/or" in connection with three or more recited objects should be understood to have the same meaning unless otherwise understood from the context.

The use of the term "include," "includes," "including," "have," "has," "having," "contain," "contains," or "containing," including grammatical equivalents thereof, should be understood generally as open-ended and non-limiting, for example, not excluding additional unrecited elements or steps, unless otherwise specifically stated or understood from the context.

Where the use of the term "about" is before a quantitative value, the present invention also includes the specific quantitative value itself, unless specifically stated otherwise. As used herein, the term "about" refers to a 10% variation from the nominal value unless otherwise indicated or inferred.

It should be understood that the order of steps or order for performing certain actions is immaterial so long as the present invention remain operable. Moreover, two or more steps or actions may be conducted simultaneously.

The use of any and all examples, or exemplary language herein, for example, "such as" or "including" is intended merely to illustrate better the present invention and does not pose a limitation on the scope of the invention unless claimed. No language in the specification should be construed as indicating any non-claimed element as essential to the practice of the present invention.

EXAMPLES

The disclosure now being generally described, will be more readily understood by reference to the following examples, which are included merely for purposes of illustration of certain aspects and embodiments of the present disclosure, and are not intended to limit the scope of the disclosure in any way.

Example 1: Protein Expression of PCCA from HepG2 and HuH-7 Cells

In this example, the protein expression of PCCA was evaluated following transfection of HepG2 and HuH-7 hepatocytes.

Briefly, HepG2 and HuH-7 cell lines were transfected with a control plasmid (i.e., mock, a plasmid with an empty vector) or an rAAV vector plasmid carrying one of seven combinations of enhancer ("Enh"), promoter ("Pro"), intron sequence, PCCA coding sequence, and polyadenylation signal ("PS") as shown as in Table 3 as follows:

TABLE 3

| rAAV Vector Plasmids | |
|---|---|
| DTC346 | CMV Enh, CBA Pro, SV40 Intron, PCCA (SEQ ID NO: 2), SV40 PS |
| DTC426 | CMV Enh, CBA Pro, SV40 Intron, PCCA (SEQ ID NO: 2), Rabbit Globin PS |
| DTC427 | CMV Enh, CBA Pro, SV40 Intron, PCCA (SEQ ID NO: 2), BGH PS |
| DTC428 | CMV Enh, CBA Pro, hFIX Intron1, PCCA (SEQ ID NO: 2), SV40 PS |

TABLE 3-continued

| rAAV Vector Plasmids | |
|---|---|
| DTC429 | CMV Enh, CBA Pro, β-globin/IgG Chimeric Intron, PCCA (SEQ ID NO: 2), SV40 PS |
| DTC430 | CMV Enh, CBA Pro, IVS2 Intron (SEQ ID NO: 1), PCCA (SEQ ID NO: 2), SV40 PS |
| DTC431 | CMV Enh, CBA Pro, rHBB Intron, PCCA (SEQ ID NO: 2), SV40 PS |

Each plasmid was transfected using Lipofectamine 2000 (Invitrogen) according to manufacturer's instructions. Cells were harvested 72 hours post-transfection and lysed with NP-40 lysis buffer (50 mM Tris-HCl pH 8.0, 150 mM NaCl, 1% NP-40) supplemented with protease inhibitor mix (Sigma) and phosphatase inhibitor cocktail 2+3 (Sigma P5726 and P0044). Proteins were resolved on 10% SDS-PAGE gels and transferred onto a polyvinylidene fluoride (PVDF) membrane. Western blot analysis was performed using an anti-PCCA antibody at 1:1000 dilution followed by a secondary antibody conjugated to far red fluorophores.

Figure 3A:
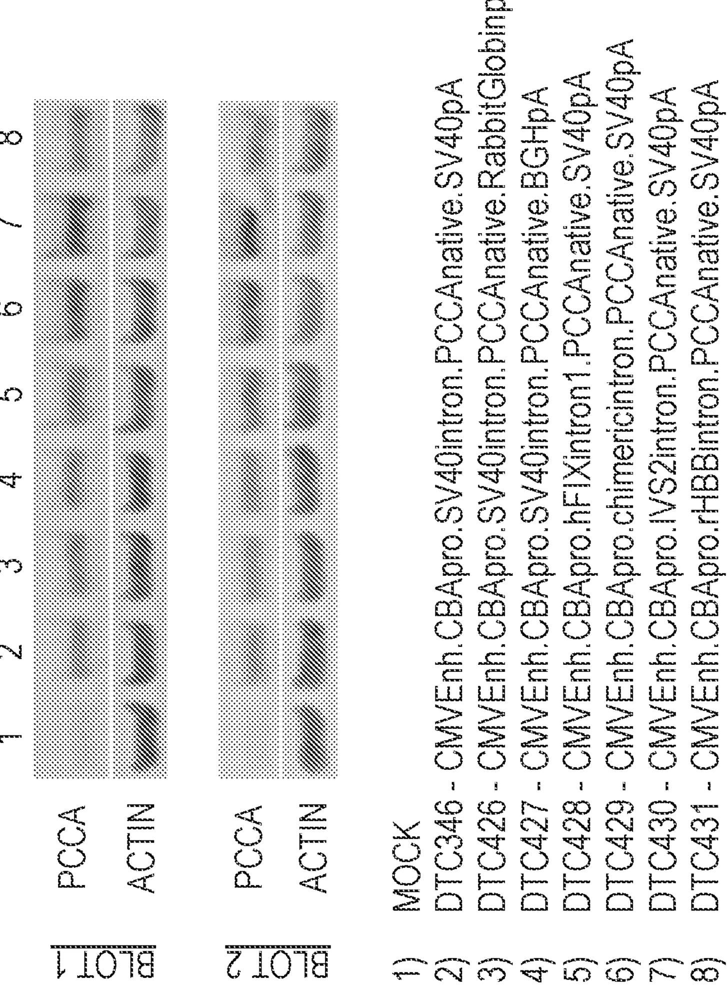
FIG. 3A is an image showing PCCA protein expression levels as detected by Western blots in HepG2 hepatocyte cells transfected with a control plasmid (mock, a plasmid with an empty vector, Lane 1) or an rAAV vector plasmid carrying one of seven combinations of enhancer, promoter, intron sequence, PCCA coding sequence, and polyadenylation signal (Lanes 2 to 8 as shown in the legend below the Western blots). β-actin (hereafter "Actin") was used as a loading control.
Figure 3B:
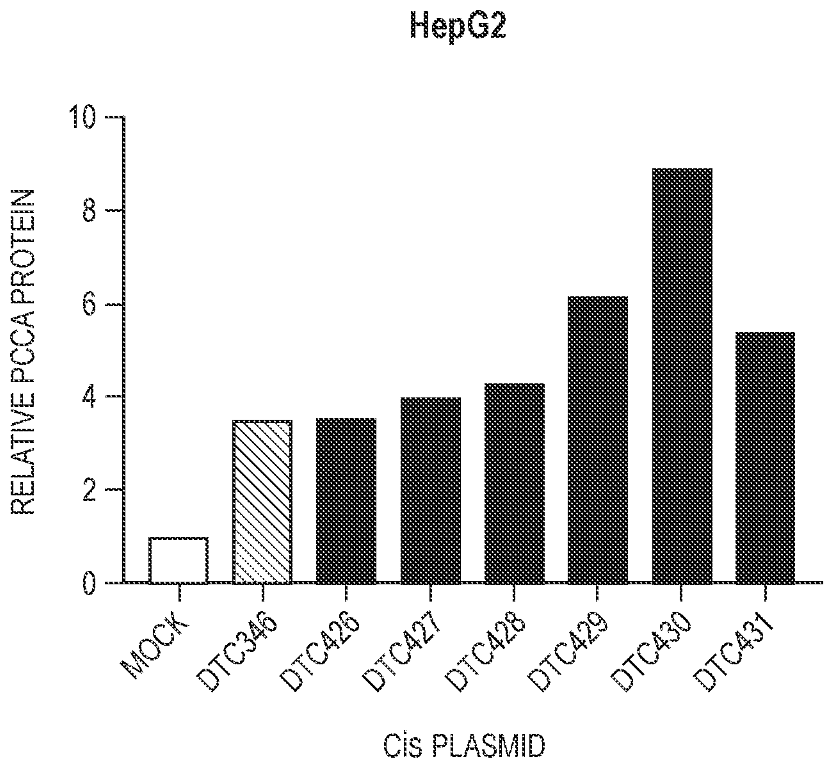
FIG. 3B is a bar graph showing relative PCCA protein expression as measured from a Western blot of HepG2 hepatocyte cells transfected with a control plasmid (mock, a plasmid with an empty vector) or an rAAV vector plasmid carrying one of seven combinations of enhancer, promoter, intron sequence, PCCA coding sequence, and polyadenylation signal.

FIG. 3A is an image showing PCCA protein expression levels as detected by Western blots in HepG2 hepatocyte cells transfected with the control plasmid (mock, a plasmid with an empty vector) or an rAAV vector plasmid corresponding to DTC346, DTC426, DTC427, DTC428, DTC429, DTC430, or DTC431. Actin was used as a loading control. FIG. 3B is a bar graph showing relative PCCA protein expression as measured from Blot 1. As FIG. 3B illustrates, DTC430 (SEQ ID NO: 30) comprising the IVS2 intron sequence of SEQ ID NO: 1 demonstrated substantially and surprisingly more PCCA protein expression in comparison to all other vector plasmids tested.

Figure 4A:
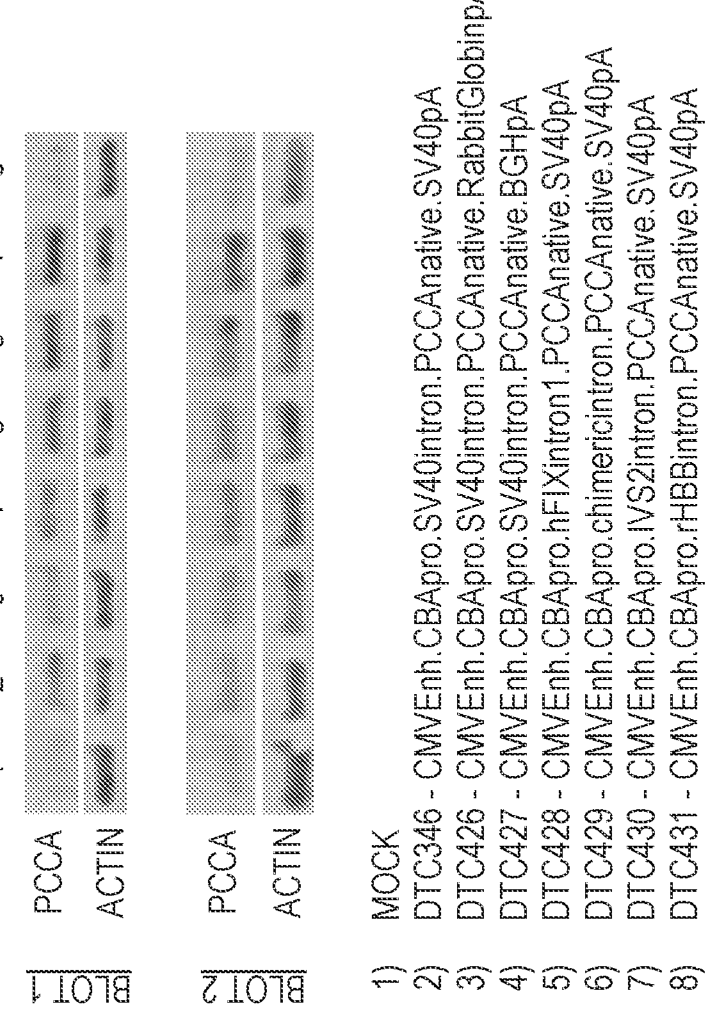
FIG. 4A is an image showing PCCA protein expression levels as detected by Western blots in HuH-7 hepatocyte cells transfected with a control plasmid (mock, a plasmid with an empty vector, Lane 1) or an rAAV vector plasmid carrying one of seven combinations of enhancer, promoter, intron sequence, PCCA coding sequence, and polyadenylation signal (Lanes 2 to 8 as shown in the legend below the Western blots). Actin was used as a loading control.
Figure 4B:
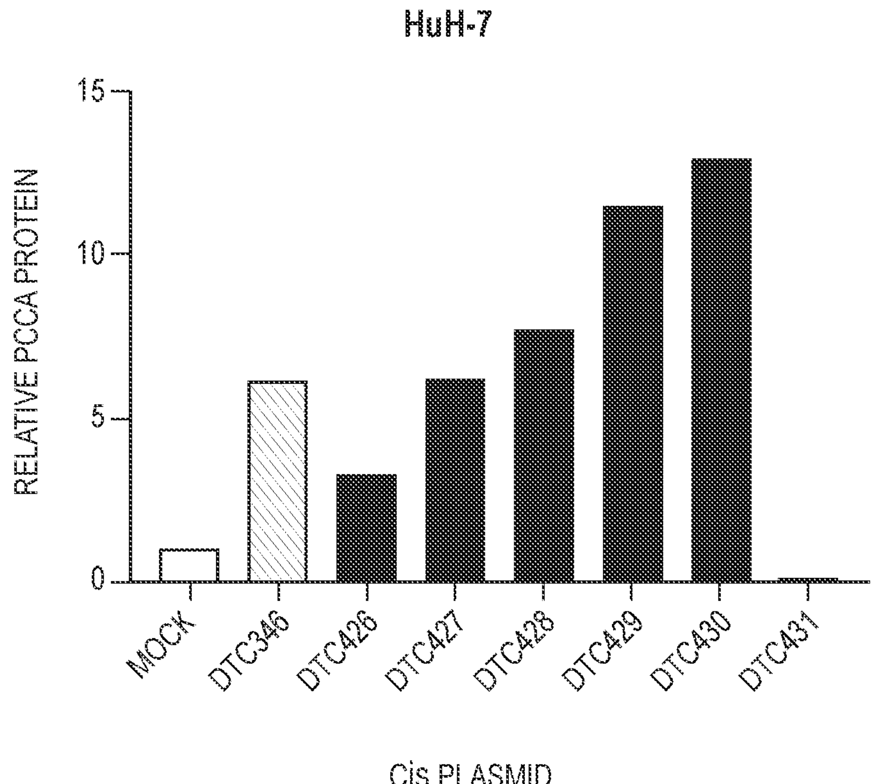
FIG. 4B is a bar graph showing relative PCCA protein expression as measured from a Western blot of HuH-7 hepatocyte cells transfected with a control plasmid (mock, a plasmid with an empty vector) or an rAAV vector plasmid carrying one of seven combinations of enhancer, promoter, intron sequence, PCCA coding sequence, and polyadenylation signal.

FIG. 4A is an image showing PCCA protein expression levels as detected by Western blots in HuH-7 hepatocyte cells transfected with the control plasmid or an rAAV vector plasmid corresponding to DTC346, DTC426, DTC427, DTC428, DTC429, DTC430, or DTC431. Actin was used as a loading control. FIG. 4B is a bar graph showing relative PCCA protein expression as measured from Blot 1. As FIG. 4B illustrates, DTC430 (SEQ ID NO: 30) comprising the IVS2 intron sequence of SEQ ID NO: 1 demonstrated substantially and surprisingly more PCCA protein expression in comparison to all other vector plasmids tested.

Figure 5A:
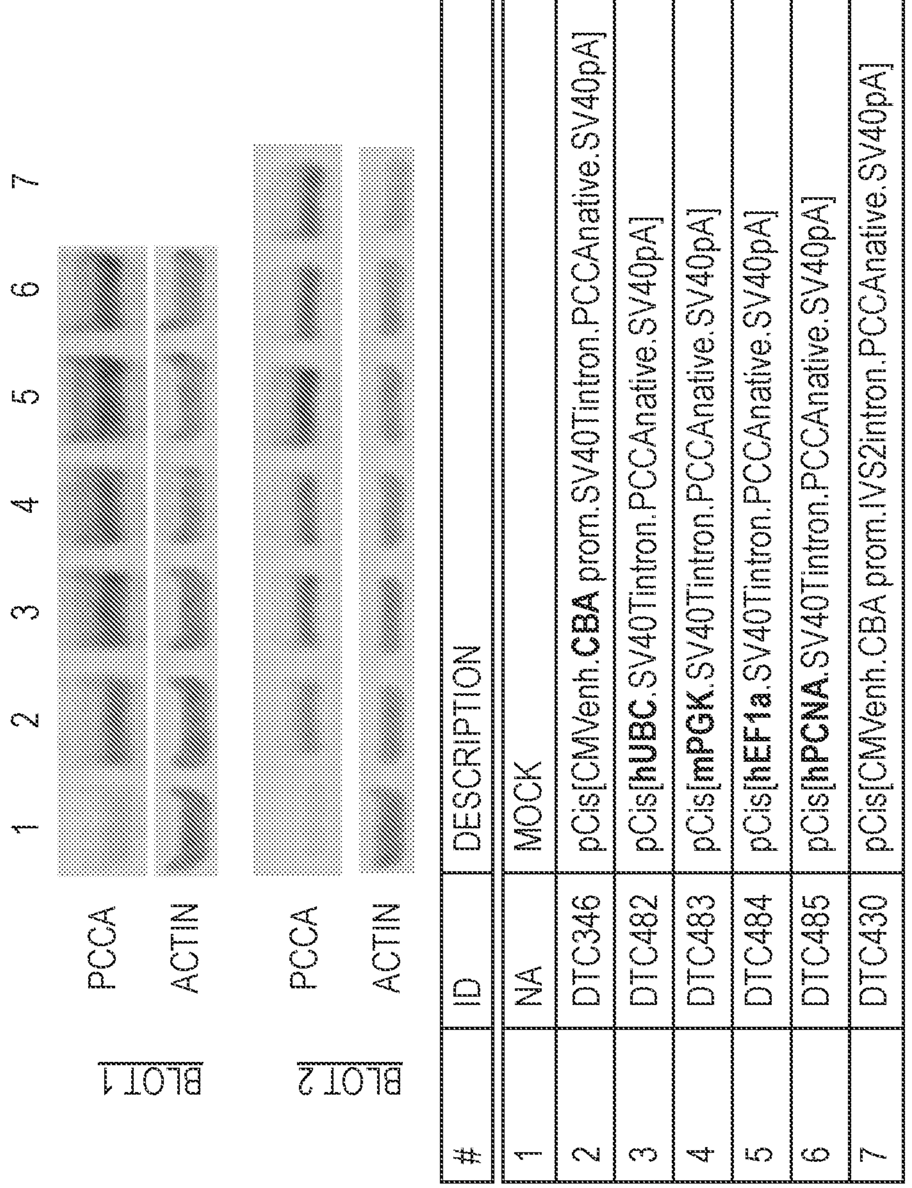
FIG. 5A is an image showing PCCA protein expression levels as detected by Western blots in HepG2 hepatocyte cells transfected with a control plasmid (mock, a plasmid with an empty vector, Lane 1) or an rAAV vector plasmid carrying one of five (Blot 1) or six (Blot 2) combinations of enhancer, promoter, intron sequence, PCCA coding sequence, and polyadenylation signal (Lanes 2 to 6 for Blot 1; Lanes 2 to 7 for Blot 2 as shown in the legend below the Western blots). Actin was used as a loading control.
Figure 5B:
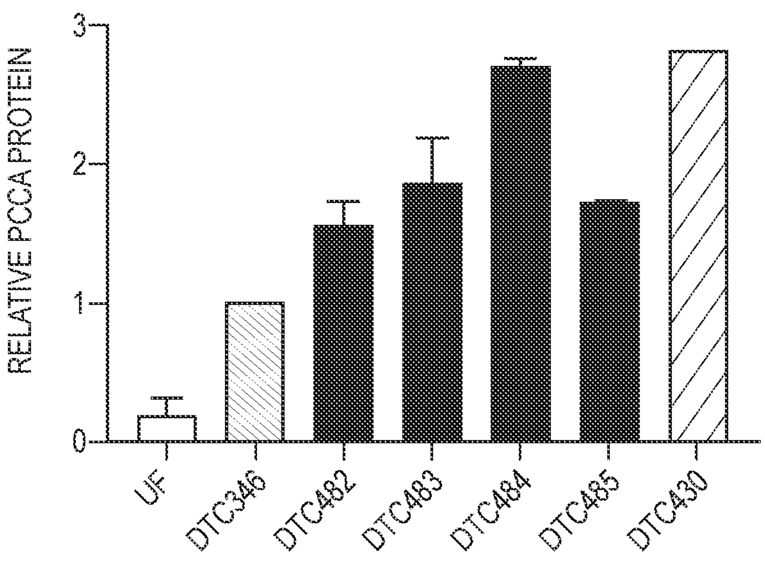
FIG. 5B is a bar graph showing relative PCCA protein expression as measured from a Western blot of HepG2 hepatocyte cells transfected with a control plasmid (UF, a plasmid with an empty vector) or an rAAV vector plasmid carrying one of six combinations of enhancer, promoter, intron sequence, PCCA coding sequence, and polyadenylation signal.

FIG. 5A is an image showing PCCA protein expression levels as detected by Western blots in HepG2 hepatocyte cells transfected with the control plasmid or an rAAV vector plasmid corresponding to DTC346, DTC482, DTC483, DTC484, or DTC485 (Blot 1); transfected with the control plasmid (UF) or an rAAV vector plasmid corresponding to DTC346, DTC482, DTC483, DTC484, DTC485, or DTC430 (Blot 2). Actin was used as a loading control. FIG. 5B is a bar graph showing relative PCCA protein expression post transfection with control plasmid or an rAAV vector plasmid (DTC346, DTC482, DTC483, DTC484, DTC485, or DTC430). The graph depicts mean protein expression levels as measured from Blot 1 and Blot 2 for UF, DTC482, DTC483, DTC484, and DTC485. The graph depicts protein expression levels as measured from Blot 2 for DTC430. As FIG. 5B illustrates, DTC430 (SEQ ID NO: 30) comprising the IVS2 intron sequence of SEQ ID NO: 1 demonstrated substantially and surprisingly more PCCA protein expression in comparison to all other vector plasmids tested.

Figure 6A:
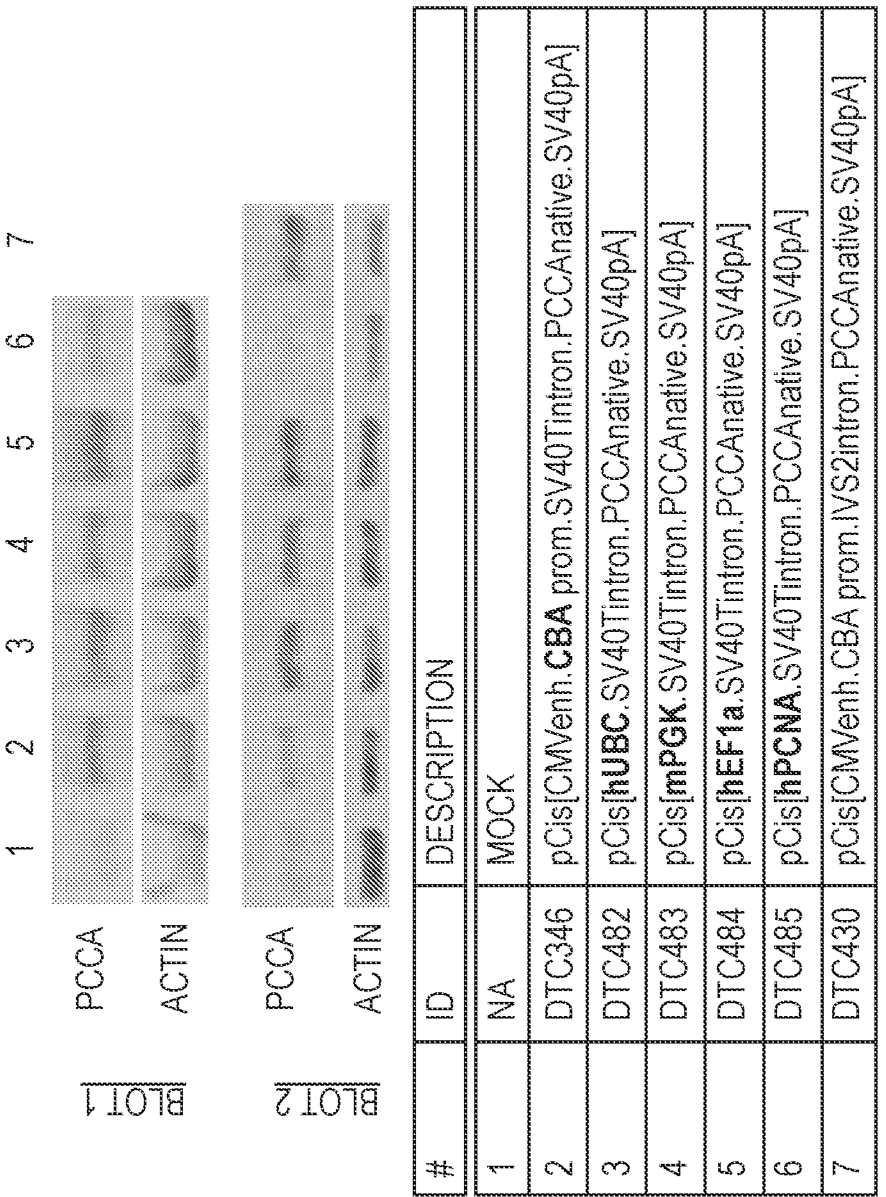
FIG. 6A is a bar graph showing relative PCCA protein expression as measured from a Western blot of HuH-7 hepatocyte cells transfected with a control plasmid (mock, a plasmid with an empty vector) or an rAAV vector plasmid carrying one of five (Blot 1) or six (Blot 2) combinations of enhancer, promoter, intron sequence, PCCA coding sequence, and polyadenylation signal. (Lanes 2 to 6 for Blot 1; Lanes 2 to 7 for Blot 2 as shown in the legend below the Western blots). Actin was used as a loading control.
Figure 6B:
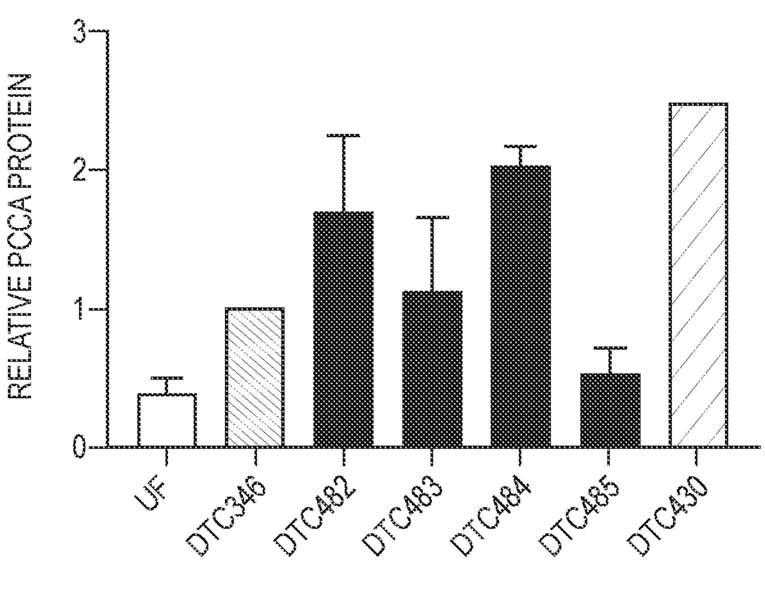
FIG. 6B is a bar graph showing relative PCCA protein expression as measured from a Western blot of HuH-7 hepatocyte cells transfected with a control plasmid (UF, a plasmid with an empty vector) or an rAAV vector plasmid carrying one of six combinations of enhancer, promoter, intron sequence, PCCA coding sequence, and polyadenylation signal.

FIG. 6A is an image showing PCCA protein expression levels as detected by Western blots in HuH-7 hepatocyte cells transfected with the control plasmid or an rAAV vector plasmid corresponding to DTC346, DTC482, DTC483, DTC484, or DTC485 (Blot 1); transfected with the control plasmid or an rAAV vector plasmid corresponding to DTC346, DTC482, DTC483, DTC484, DTC485, or DTC430 (Blot 2). Actin was used as a loading control. FIG. 6B is a bar graph showing relative PCCA protein expression post transfection with control plasmid or an rAAV vector plasmid (DTC346, DTC482, DTC483, DTC484, DTC485, or DTC430). The graph depicts mean protein expression levels as measured from Blot 1 and Blot 2 for UF, DTC482, DTC483, DTC484, and DTC485. The graph depicts protein expression levels as measured from Blot 2 for DTC430. As FIG. 6B illustrates, DTC430 (SEQ ID NO: 30) comprising the IVS2 intron sequence of SEQ ID NO: 1 demonstrated substantially and surprisingly more PCCA protein expression in comparison to all other vector plasmids tested.

This example suggests that insertion of a human β-globin IVS2 intron sequence (SEQ ID NO: 1) into a PA gene therapy vector may provide substantial advantages with respect to transgene expression. Utilization of this intron sequence in a PCCA- or PCCB-encoding rAAV shows promise for delivering high transgene expression, thereby reducing the vector dose required for successful gene therapy of propionic acidemia.

Example 2: Human PCCA activity in Hypomorphic PA Mouse Model

This example relates to testing the treatment effects of rAAV-mediated delivery of a transgene cassette encoding PCCA, comprising the IVS2 intron sequence of SEQ ID NO: 1 (DTC430 (SEQ ID NO: 30)) on propionic acidemia (PA) in a hypomorphic PA mouse model. Deletion of the Pcca gene in mice mimics the most severe forms of the human disease. Pcca-mice die within 36 hours of birth, making it difficult to test intravenous systemic therapies in them (see Guenzel et al., Mol Ther. 2013 July; 21 (7):1316-1323). Hypomorphic PA mouse model, $Pcca^{-/-}$ (A138T), was generated by deletion of the Pcca with a transgene bearing an A138T mutant of the human PCCA protein. $Pcca^{-/-}$ (A138T) mice have 2% of wild-type PCC activity, survive to adulthood, and have elevations in propionylcarnitine, methylcitrate, glycine, alanine, lysine, ammonia, and markers associated with cardiomyopathy similar to those in patients with PA. Briefly, eight mice were intravenously injected with $5\times10^{11}$, $1\times10^{12}$, $2\times10^{12}$ or $4\times10^{12}$ viral genomes (VG)/kg (5E11, 1E12, 2E12 and 4E12, respectively) of rAAV8 encoding DTC430 (SEQ ID NO: 30) comprising the IVS2 intron sequence of SEQ ID NO: 1 (PCCA expression levels after injection are provided in FIG. 8A). Five mice were intravenously injected with $3\times10^{11}$, $1\times10^{12}$, or $3\times10^{12}$ VG/kg (3E11, 1E12 or 3E12, respectively) of rAAV9 encoding DTC430 (SEQ ID NO: 30) comprising the IVS2 intron sequence of SEQ ID NO: 1 (PCCA expression levels after injection are provided in FIG. 8B). PBS was injected to the control mice ("CONT").

Figure 7A:
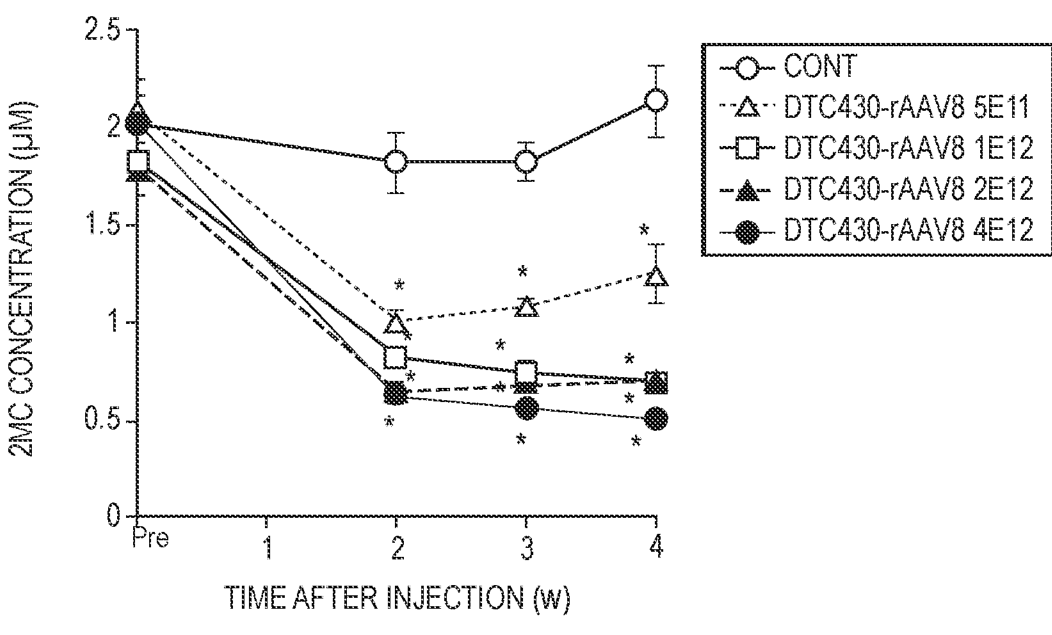
FIGS. 7A and 7B are line graphs showing plasma concentrations of known biomarkers of propionic acidemia in a hypomorphic PA mouse model, $Pcca^{-/-}$ (A138T), following rAAV-mediated delivery of a transgene cassette encoding PCCA, comprising the IVS2 intron sequence of SEQ ID NO: 1 (DTC430 (SEQ ID NO: 30)) (time after injection is provided in weeks (W)).
Figure 7B:
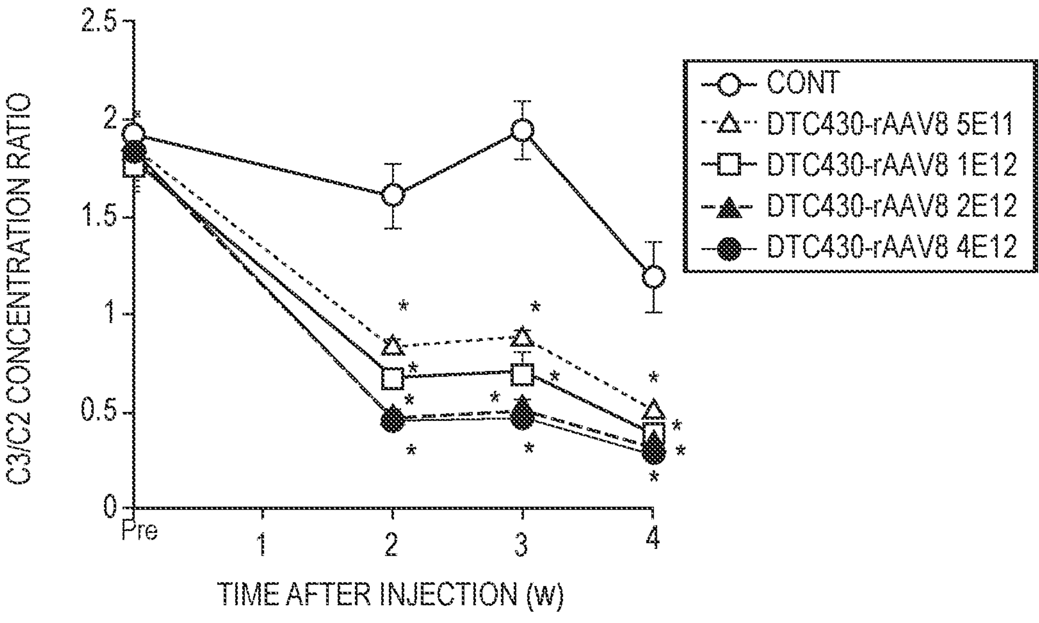

Plasma concentrations of known biomarkers of PA (2-methylcitrate (2MC), propionylcarnitine (C3) and acylcarnitine (C2)) were measured by liquid chromatography-mass spectrometry (LC-MS) before ("Pre") and 2, 3 and 4 weeks after injection of rAAV comprising a transgene cassette encoding PCCA (SEQ ID NO: 2), comprising the IVS2 intron sequence of SEQ ID NO: 1 (DTC430 (SEQ ID NO: 30)). FIGS. 7A and 7B are line graphs showing plasma concentrations of known biomarkers of propionic acidemia in a hypomorphic PA mouse model, $Pcca^{-/-}$ (A138T), following treatment with rAAV comprising a transgene cassette encoding PCCA (SEQ ID NO: 2), comprising the IVS2 intron sequence of SEQ ID NO: 1 (DTC430 (SEQ ID NO: 30)), compared to the level when a control (PBS) is injected ("CONT").

FIG. 7A is a line graph showing plasma concentration of 2-methylcitrate (2MC) in a hypomorphic PA mouse model, $Pcca^{-/-}$ (A138T), following treatment with rAAV comprising a transgene cassette encoding PCCA (SEQ ID NO: 2), comprising the IVS2 intron sequence of SEQ ID NO: 1 (DTC430 (SEQ ID NO: 30)). FIG. 7B is a line graph showing plasma C3/C2 (propionylcarnitine/acylcarnitine) concentration ratio in a hypomorphic PA mouse model, $Pcca^{-/-}$ (A138T), following treatment with rAAV comprising a transgene cassette encoding PCCA (SEQ ID NO: 2), comprising the IVS2 intron sequence of SEQ ID NO: 1 (DTC430 (SEQ ID NO: 30)). The term "Pre" in FIG. 7A and FIG. 7B indicates 2MC and C3/C2 values, respectively, 2 weeks before the injection of rAAV comprising a transgene cassette encoding PCCA (SEQ ID NO: 2), comprising the IVS2 intron sequence of SEQ ID NO: 1 (DTC430 (SEQ ID NO: 30)) or PBS ("CONT"). Error bars represent standard error. * denotes $P<0.05$ in comparison to PBS-treated group using Dunnett's test.

Mice treated with rAAV comprising a transgene cassette encoding PCCA (SEQ ID NO: 2), comprising the IVS2 intron sequence of SEQ ID NO: 1 (DTC430 (SEQ ID NO: 30)) demonstrated statistically significant reductions in plasma 2MC and C3/C2 levels compared with those of PBS-treatment ("CONT").

Figure 8A:
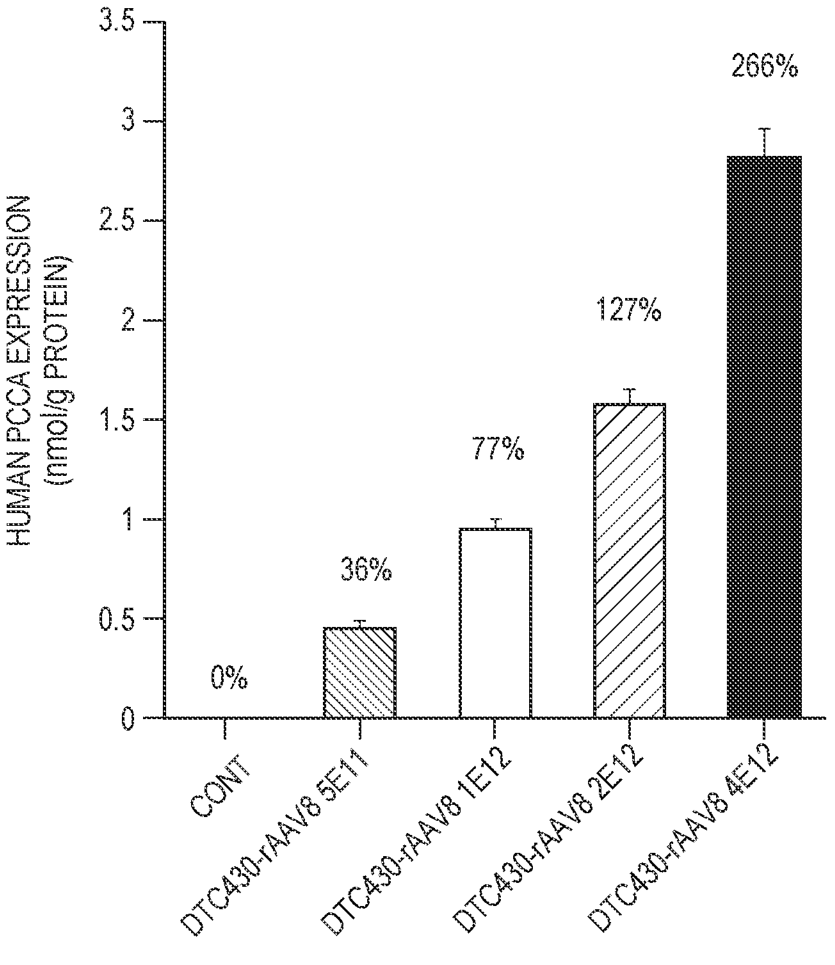
FIG. 8A is a bar graph showing the concentration (in nmol/g protein) of human PCCA protein expressed in a hypomorphic PA mouse model, $Pcca^{-/-}$ (A138T), following administration of PBS ("CONT") or varying doses of rAAV8-mediated delivery of a transgene cassette encoding PCCA, comprising the IVS2 intron sequence of SEQ ID NO: 1 (DTC430 (SEQ ID NO: 30)). The listed percentage number denotes human PCCA expression calculated as a percentage to that of human PCCA protein levels in a non-PA human liver. Error bars represent standard error.
Figure 8B:
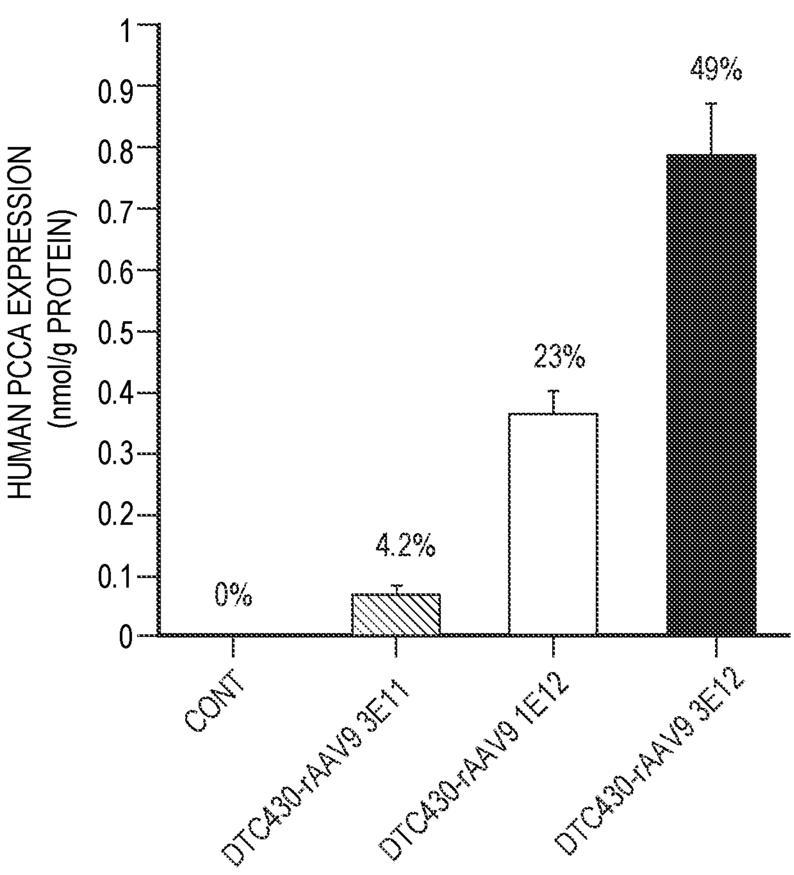
FIG. 8B is a bar graph showing the concentration (in nmol/g protein) of human PCCA protein expressed in a hypomorphic PA mouse model, $Pcca^{-/-}$ (A138T), following administration of PBS ("CONT") or varying doses of rAAV9-mediated delivery of a transgene cassette encoding PCCA, comprising the IVS2 intron sequence of SEQ ID NO: 1 (DTC430 (SEQ ID NO: 30)). The listed percentage number denotes human PCCA expression calculated as a percentage to that of human PCCA protein levels in a non-PA human liver. Error bars represent standard error.

Four weeks after injection, livers were homogenized, and human PCCA protein was measured by LC-MS. FIGS. 8A and 8B are bar graphs showing the concentration (in nmol/g protein) of human PCCA protein expressed in a hypomorphic PA mouse model, Pcca-(A138T), following treatment with rAAV comprising a transgene cassette encoding PCCA (SEQ ID NO: 2), comprising the IVS2 intron sequence of SEQ ID NO: 1 (DTC430 (SEQ ID NO: 30)). The listed percentage number denotes human PCCA expression calculated as a percentage to that of human PCCA protein levels in non-PA human liver (Human Liver Homogenate, H0610.H, XenoTech). Error bars represent standard error. As shown in FIG. 8A, mice injected with $5\times10^{11}$, $1\times10^{12}$, $2\times10^{12}$ or $4\times10^{12}$ VG/kg of rAAV8 encoding PCCA (SEQ ID NO: 2) (e.g., DTC430 (SEQ ID NO: 30) comprising the IVS2 intron sequence of SEQ ID NO: 1) expressed 36%, 77%, 127%, and 226% of human PCCA levels compared to human PCCA protein levels in non-PA human liver, respectively. As shown in FIG. 8B, mice injected with $3\times10^{11}$, $1\times10^{12}$ or $3\times10^{12}$ VG/kg (3E11, 1E12 or 3E12, respectively) of rAAV9 encoding PCCA (SEQ ID NO: 2) (e.g., DTC430 (SEQ ID NO: 30) comprising the IVS2 intron sequence of SEQ ID NO: 1) expressed 4.2%, 23%, or 49% of human PCCA levels compared to human PCCA protein levels in non-PA human liver, respectively. These data demonstrated that rAAV-mediated PCCA gene delivery resulted in substantially elevated levels of PCCA in a hypomorphic PA mouse model.

INCORPORATION BY REFERENCE

The entire disclosure of each of the patent documents and scientific articles referred to herein is incorporated by reference for all purposes.

EQUIVALENTS

The disclosure may be embodied in other specific forms without departing from the spirit or essential characteristics thereof. The foregoing embodiments are therefore to be considered in all respects illustrative rather than limiting the disclosure described herein. Various structural elements of the different embodiments and various disclosed method steps may be utilized in various combinations and permutations, and all such variants are to be considered forms of the disclosure. Scope of the disclosure is thus indicated by the appended claims rather than by the foregoing description, and all changes that come within the meaning and range of equivalency of the claims are intended to be embraced therein.

What is claimed is:

1. A polynucleotide which comprises a nucleic acid sequence at least 90% identical, at least 95% identical, at least 99% identical, or 100% identical to SEQ ID NO: 30 or SEQ ID NO: 31.

2. An isolated host cell comprising the polynucleotide of claim 1, wherein the isolated host cell is capable of producing an adeno-associated viral (AAV) vector.

3. The isolated host cell of claim 2, wherein the host cell is selected from a HeLa, Cos-7, HEK293, A549, BHK, Vero, RD, HT-1080, ARPE-19, and MRC-5 cell.

* * * * *